United States Patent
Wada et al.

(10) Patent No.: US 8,106,783 B2
(45) Date of Patent: Jan. 31, 2012

(54) INPUT APPARATUS, REMOTE CONTROLLER AND OPERATING DEVICE FOR VEHICLE

(75) Inventors: Hiromune Wada, Nagoya (JP); Takashi Aoki, Gifu (JP)

(73) Assignee: Denso Corporation, Kariya (JP)

( * ) Notice: Subject to any disclaimer, the term of this patent is extended or adjusted under 35 U.S.C. 154(b) by 298 days.

(21) Appl. No.: 12/401,881

(22) Filed: Mar. 11, 2009

(65) Prior Publication Data

US 2009/0231145 A1 Sep. 17, 2009

(30) Foreign Application Priority Data

| Mar. 12, 2008 | (JP) | 2008-62873 |
| Mar. 12, 2008 | (JP) | 2008-62874 |
| Mar. 25, 2008 | (JP) | 2008-78586 |
| Mar. 26, 2008 | (JP) | 2008-80924 |

(51) Int. Cl.
*G08B 23/00* (2006.01)

(52) U.S. Cl. ............. 340/575; 340/426.11; 340/426.22; 340/426.24; 340/426.15; 348/77; 348/78

(58) Field of Classification Search .................. 340/576, 340/575, 573.1, 426.11, 426.22, 426.24, 340/426.15; 345/3.1; 348/77, 78, 66
See application file for complete search history.

(56) References Cited

U.S. PATENT DOCUMENTS

| 5,729,619 | A | * | 3/1998 | Puma | 382/115 |
| 5,813,989 | A | * | 9/1998 | Saitoh et al. | 600/484 |
| 6,366,442 | B1 | | 4/2002 | Onodera | |
| 6,448,670 | B1 | | 9/2002 | Onodera et al. | |
| 6,591,175 | B2 | | 7/2003 | Numata et al. | |
| 2003/0214526 | A1 | | 11/2003 | Numata et al. | |
| 2005/0230175 | A1 | * | 10/2005 | Brown et al. | 180/272 |
| 2008/0231461 | A1 | * | 9/2008 | Sanchez et al. | 340/575 |
| 2009/0009478 | A1 | | 1/2009 | Badali et al. | |
| 2009/0160732 | A1 | | 6/2009 | Kimura | |

FOREIGN PATENT DOCUMENTS

| JP | 64-040793 | 2/1989 |
| JP | 04-038507 | 2/1992 |
| JP | H05-69498 | 9/1993 |
| JP | 07-144556 | 6/1995 |
| JP | 08-058302 | 3/1996 |
| JP | 09-118318 | 5/1997 |
| JP | 2000-006687 | 1/2000 |
| JP | 2000-106069 | 4/2000 |

(Continued)

OTHER PUBLICATIONS

Japanese Office Action dated Jan. 7, 2010, issued in corresponding Japanese Application No. 2008-062874, with English translation.

(Continued)

*Primary Examiner* — Jennifer Mehmood
*Assistant Examiner* — Hongmin Fan
(74) *Attorney, Agent, or Firm* — Nixon & Vanderhye P.C.

(57) ABSTRACT

An input apparatus for a vehicle includes: an operation element operable by an occupant of the vehicle; a biological information acquisition element acquiring biological information of the occupant; an unawakened state detection element detecting an unawakened state of the occupant based on the biological information, wherein the unawakened state is defined by a predetermined state different from an awakened state; and an operation disabling element disabling an operation input from the operation element when the unawakened state detection element detects the unawakened state.

15 Claims, 31 Drawing Sheets

FOREIGN PATENT DOCUMENTS

| | | |
|---|---|---|
| JP | 2000-149721 | 5/2000 |
| JP | 2001-222271 | 8/2001 |
| JP | 2002-157034 | 5/2002 |
| JP | 2003-280814 | 10/2003 |
| JP | 2004-128780 | 4/2004 |
| JP | 2004-314750 | 11/2004 |
| JP | 2005-259019 | 9/2005 |
| JP | 2006-205938 | 8/2006 |
| JP | 2007-015622 | 1/2007 |
| JP | 2007-022532 | 2/2007 |
| JP | 2007-030754 | 2/2007 |
| JP | 2007-094558 | 4/2007 |
| JP | 2007-198574 | 8/2007 |
| JP | 2007-201825 | 8/2007 |
| JP | 2007-249477 | 9/2007 |
| JP | 2007-276615 | 10/2007 |

OTHER PUBLICATIONS

Japanese Office Action dated Feb. 17, 2010, issued in corresponding Japanese Application No. 2008-080924, with English translation.

Japanese Office Action dated Jul. 30, 2010, issued in corresponding Japanese Application No. 2008-062874, with English translation.

Japanese Office Action Feb. 23, 2011, issued in corresponding Japanese Application No. 2008-62874, with English translation.

Office Action (7 pgs.) dated Sep. 16, 2011 issued in co-pending U.S. Appl. No. 13/099,553.

Japanese Office Action dated Dec. 7, 2009, issued in corresponding Japanese Application No. 2008-062873, with English translation.

Japanese Office Action dated Mar. 12, 2010, issued in corresponding Japanese Application No. 2008-078586, with English translation.

* cited by examiner

INPUT APPARATUS, REMOTE CONTROLLER AND OPERATING DEVICE FOR VEHICLE

CROSS REFERENCE TO RELATED APPLICATIONS

This application is based on Japanese Patent Applications No. 2008-62873 filed on Mar. 12, 2008, No. 2008-62874 filed on Mar. 12, 2008, No. 2008-78586 filed on Mar. 25, 2008, and No. 2008-80924 filed on Mar. 26, 2008, the disclosures of which are incorporated herein by reference.

FIELD OF THE INVENTION

The present invention relates to an input apparatus, a remote controller and an operating device for a vehicle.

BACKGROUND OF THE INVENTION

As described in Patent Document 1: JP-2000-6687 A, there has been developed an image overlaying input apparatus for remotely controlling devices. Such input apparatus is provided with a remote operation part within reach of an operator independently of a display apparatus for displaying an operation screen (main screen). The input apparatus captures and extracts a hand that operates the remote operation part. The input apparatus reflects a captured hand image and an acquired hand operation on the operation screen (main screen) of the display apparatus. The input apparatus controls the display as if the operator directly touches the operation screen. When the input apparatus is provided for a vehicle, the remote operation part is provided within reach of a user sitting on a seat for improved operability. In many cases, the remote operation part is configured as a touch-based operation part including a touch operation panel.

The above-mentioned input apparatus uses the remote operation part provided within reach of the user. The user unintentionally touches the remote operation part to cause an incorrect input operation. The driver's consciousness level lowers when he or she becomes drowsy. In such case, the user is particularly likely to incorrectly operate the operation part near himself or herself. Further, a slight touch on a touch-based operation part may easily cause an incorrect input operation.

To solve this problem, a conventional technology previously locks the operation part against a normal operation. When a specified unlock operation is performed, the operation part is unlocked to allow an input operation. Generally, there is provided a switch for locking or unlocking the operation part independently of the operation part. The user is forced to directly unlock the operation part.

The technology described in Patent Document 2: JP-2007-198574 A allows a hand to touch an existing switch for a specified time interval or longer or provides a specified pattern of operations on an existing switch. This technology eliminates the need for providing an additional switch and promotes space saving despite the recent tendency of using many switches. However, the technology requires a complicated operation to be performed by the user and causes inconvenience to the user in the unlock operation.

The technology described in Patent Document 3: JP-2000-106069 A uses an approach sensor to detect a hand approaching the operation part and activates an object to be controlled by the operation part for which the approaching hand is detected. However, this technology activates the operation object and makes it operable even when the user unintentionally moves his or her hand to the vicinity of the operation part. It may be difficult to effectively prevent an incorrect operation.

Further, in recent years, there is an increasing demand for a vehicle mounted with a display unit that displays various information on front part of a vehicle interior near a driver's view or a position far from the driver's seat toward the front so as to reduce movement of the driver's line of sight. In such vehicle, it is difficult for the driver to reach for the display unit or make a stable touch operation. As an alternative to the technique of directly touching switches displayed on the display unit, it is common to use a technique of mounting a remote control apparatus on a center console and indirectly operating switches displayed on a display unit via the remote control apparatus. In this case, the remote control apparatus is provided near the palm of a driver's hand so that the driver can easily operate the apparatus. When the remote control apparatus is provided near the palm, however, the driver may inadvertently touch or allow something to contact with an operational part of the remote control apparatus, causing an input to the operational part of the remote control apparatus. To solve this problem, for example, the remote control apparatus according to Patent Document 4: JP-2003-280814 A provides a palm detection sensor for part of the remote control apparatus where the driver's palm is placed. An input to the operational part of the remote control apparatus is enabled when the palm detection sensor detects the palm.

However, the remote control apparatus according to Patent Document 4 enables an input operation even when the driver inadvertently operates the operational part of the remote control apparatus.

Furthermore, an example of operating devices uses a pointing device such as a mouse or a trackball connected to an electronic device for controlling electronic device operations. The operating device may move a pointer or the like on a display device screen in accordance with the direction in which the pointing device is operated. The operating device is used as an input device and is operated by a user to output a coordinate corresponding to the operation direction to the electronic device. Such operating device is also used for onboard devices such as a navigation system, an air conditioner panel, and an audio system.

In a vehicle, a display unit is placed at a position distant from a driver's seat but near the driver's field of view so as to minimize movement of the driver's line of sight. It is difficult for the driver to reach out for a touch panel as a conventional operation means, making a stable operation difficult. To solve this problem, a pointing device such as a haptic device is attached to a center console the driver can reach for without excessively changing his or her posture. This makes it possible to remotely operate an intended onboard device.

A remote operating device according to Patent Document 5: JP-2007-094558 A detects three-dimensional movement in a space without necessitating a user to directly touch a device to be operated. The remote operating device enables remote operations without restriction on places or situations.

According to a conventional technology, the pointing device is placed where the user can easily operate it. However, the user may unintentionally touch the pointing device to cause an unexpected operation or display that may become a hindrance to driving.

The example in Patent Document 5 neither discloses nor suggests how to determine or avoid a user's unintentional operation. The vehicle behavior such as turn or vibration may move a mobile telephone. This may be incorrectly recognized as a user operation.

SUMMARY OF THE INVENTION

In view of the above-described problem, it is an object of the present disclosure to provide a vehicular input apparatus capable of effectively preventing an incorrect operation on an operation element near a vehicle occupant. It is another object of the present disclosure to provide a vehicular input apparatus capable of reliably preventing an incorrect operation on an operation part provided near a vehicle occupant and promptly enabling an input operation when a user indicates his or her intention to perform the operation. Further, it is another object of the present disclosure to provide an affordable and simple remote controller that can disable a driver's inadvertent input operation. Furthermore, it is another object of the present disclosure to provide a vehicular operating device capable of preventing an onboard device from being operated by a user's unintentional operation.

According to a first aspect of the present disclosure, an input apparatus for a vehicle includes: an operation element operable by an occupant of the vehicle; a biological information acquisition element acquiring biological information of the occupant; an unawakened state detection element detecting an unawakened state of the occupant based on the biological information, wherein the unawakened state is defined by a predetermined state different from an awakened state; and an operation disabling element disabling an operation input from the operation element when the unawakened state detection element detects the unawakened state.

According to the above-mentioned configuration, the vehicular input apparatus detects a lowered consciousness level as an unawakened state in which an occupant becomes drowsy. When the unawakened state is detected, the vehicular input apparatus disables any input operation, making it possible to prevent an incorrect operation. The detection of a predetermined unawakened state includes a case of comparing the acquired biological information with a predetermined unawakened state and a case of comparing the same with a predetermined normal awakened state.

According to a second aspect of the present disclosure, an input apparatus for a vehicle includes: an operation device operable by an operator in the vehicle; a visual line detection element detecting a visual line of the operator who operates the operation device; a releasing visual line determination element determining whether the visual line is disposed in a predetermined operation releasing visual line state; and an input operation mode setup element setting an input operation enable mode and an input operation disable mode. The input operation enable mode allows the operation device to input an operation from the operator. The input operation disable mode prohibits the operation device from inputting an operation from the operator. The input operation mode setup element switches the operation device from the input operation disable mode to the input operation enable mode when the releasing visual line determination element determines that the visual line is disposed in the predetermined operation releasing visual line state.

When the operation device is locked or inhibited against operations, the above-mentioned configuration can unlock the operation device in accordance with the visual line or movement of the user's eye. The operation device remains unlocked unless the user indicates his or her intention to perform an operation by setting his or her visual line to a specified state. It is possible to reliably prevent an incorrect operation on the operation device unlike a conventional mechanism that may unlock the operation element simply because a hand is detected near the operation element. Moving the visual line is more convenient for the user than moving the hand. It is possible to greatly improve the conventional inconvenient unlock operation.

According to a third aspect of the present disclosure, a remote controller includes: an operation device including an operation element remotely operating an in-vehicle device; a locking element switching the operation element between a lock mode and an unlock mode, wherein the operation element is operable when the locking element switches to the unlock mode, and the operation element is not operable when the locking element switches to the lock mode; a load detection element detecting a load applied to the operation element; and a control element controlling the locking element. The control element controls the locking element to switch to the lock mode when the load is smaller than a predetermined value, and the control element controls the locking element to switch to the unlock mode when the load is equal to or larger than the predetermined value.

The remote controller assumes the absence of a user intention to operate the operation part when a load detected by the load detection element is smaller than a predetermined value. The operation element remains locked under control of the locking element in accordance with the control element. On the other hand, the remote controller assumes the presence of a user intention to operate the operation element when a load detected by the load detection element is greater than or equal to the predetermined value. The operation element is unlocked under control of the locking element in accordance with the control element.

When the user inadvertently operates the operation element of the remote controller, a load detected by the load detection element is smaller than the predetermined value. The locking element keeps the operation element locked and nullifies an input operation on the operation element.

According to a fourth aspect of the present disclosure, an operating device for a vehicle includes: an operation element disposed within a reach of an operator; an operation determination element determining whether the operator operates the operation element; a display displaying an image on a screen of the display when the operation determination element determines that the operator operates the operation element, the image corresponding to an input operation of the operator; a visual line direction detection element detecting a direction of a visual line of the operator; and an operation mode control element switching the operation element from a normal mode to a restriction mode when the direction of the visual line is not directed to the screen of the display. The normal mode does not restrict the input operation of the operation element, and the restriction mode restricts the input operation of the operation element.

The above-mentioned configuration can detect a user's visual line direction to determine whether the user intentionally or unintentionally operates a tactilely operated device. It is possible to solve the problem of unintentionally touching the pointing device to cause an unexpected operation or display that may become a hindrance to driving.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

Figure 1:
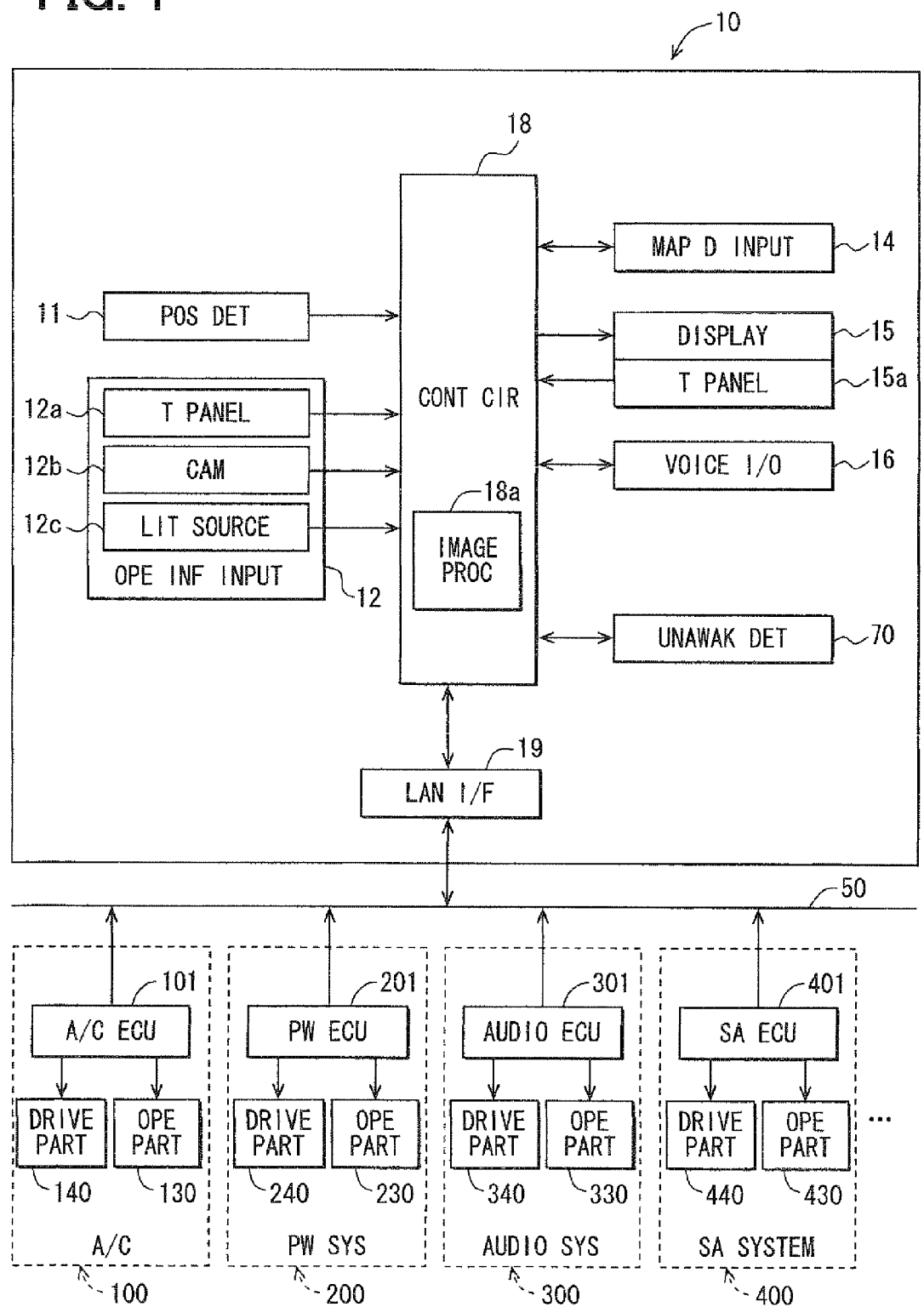
FIG. 1 is a block diagram showing a vehicular navigation system using a vehicular image overlaying input apparatus as an example of the tactile input apparatus according to a first embodiment.

FIG. 1 is a block diagram showing a configuration of a vehicular navigation system using the input apparatus according to a first embodiment. According to the embodiment, an input apparatus 1 complies with an image overlaying technology. The input apparatus 1 is provided with a display apparatus 15 and an operation panel 12 at different positions. The display apparatus 15 is capable of displaying a switch image (operation icon) for touch operation on a display screen. The operation panel 12 as an operation information input part is used for remotely controlling the touch operation on the display screen. The touch-type input apparatus according to the embodiment is targeted for controlling not only navigation functions but also the other onboard electronic device functions such as audio, air conditioner, power window, and seat adjusting functions. The functions are controlled by control parts such as an air conditioner ECU 101, a power window ECU 201, an audio ECU 301, and a seat adjusting ECU 401, and so on that are connected to a control circuit 18 through an interior LAN 50.

A navigation system 10 includes the following. A position detector 11 uses the GPS to detect the current position of the vehicle. An operation information input part 12 is used for entering various instructions from an operator such as a driver. A map data input device 14 is used for entering map data from an external recording medium that stores map data and various information. A display apparatus 15 provides various displays such as a map display screen and a television (TV) screen. A voice input/output device 16 outputs various guidance voices and inputs voice of an operator such as a driver. A vehicle interface (I/F) 19 interchanges vehicle information. The control circuit 18 connects with these components. The control circuit 18 also connects ECUs 101, 201, 301, 401, and so on for controlling the other onboard electronic devices with an unawakened state detection part 70 that detects a predetermined unawakened state. The unawakened state differs from a vehicle occupant's normal awakened state.

Figure 3:
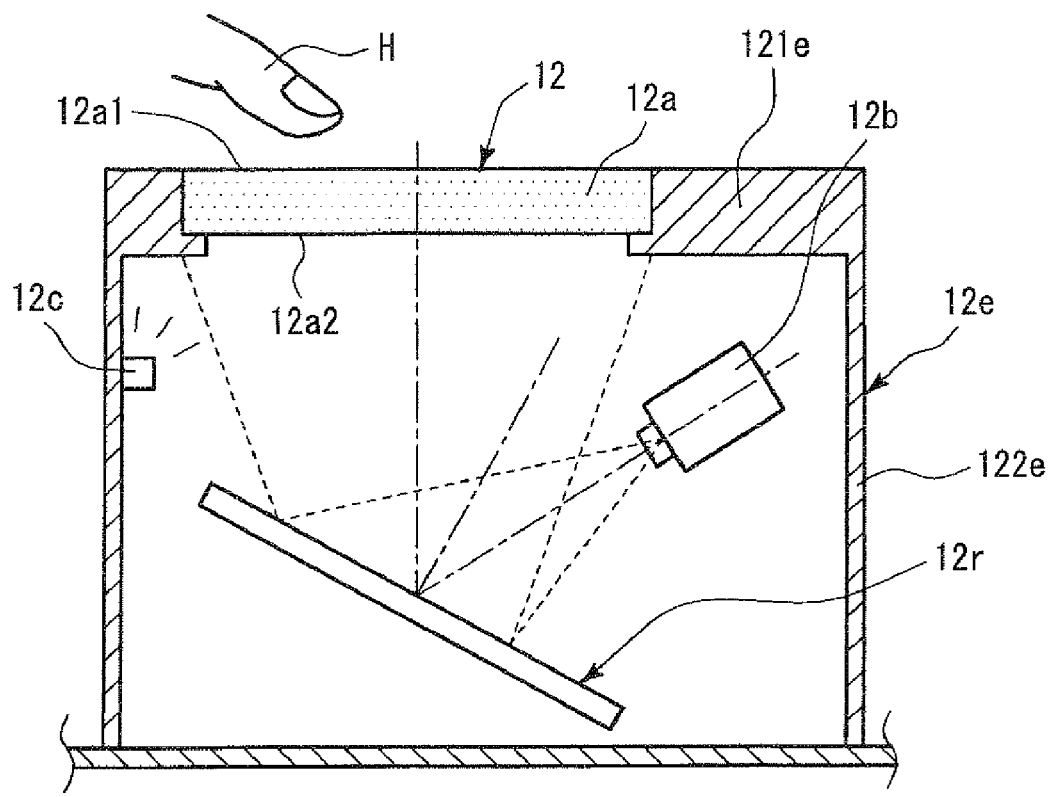
FIG. 3 is a sectional view showing an example configuration of an operation information input part.

As shown in FIG. 3, the operation information input part 12 includes the following. A light source 12c radiates light of a predetermined waveband. A translucent operation panel 12a as a touch panel is provided so that the light radiated from the light source 12c is transmitted from a second surface 12a2 to a first surface 12a1. A camera (approaching object capturing means) 12b captures an object including the operation panel 12a from the rear side 12a2 of the operation panel 12a.

The operation panel 12a is translucent so as to transmit at least the light radiated from the light source 12c. The operation panel 12a according to the embodiment is configured as a known resistive touch panel provided with vertical and horizontal transparent electrodes. An output from the operation panel 12a is input to the control circuit 18.

Figure 2:
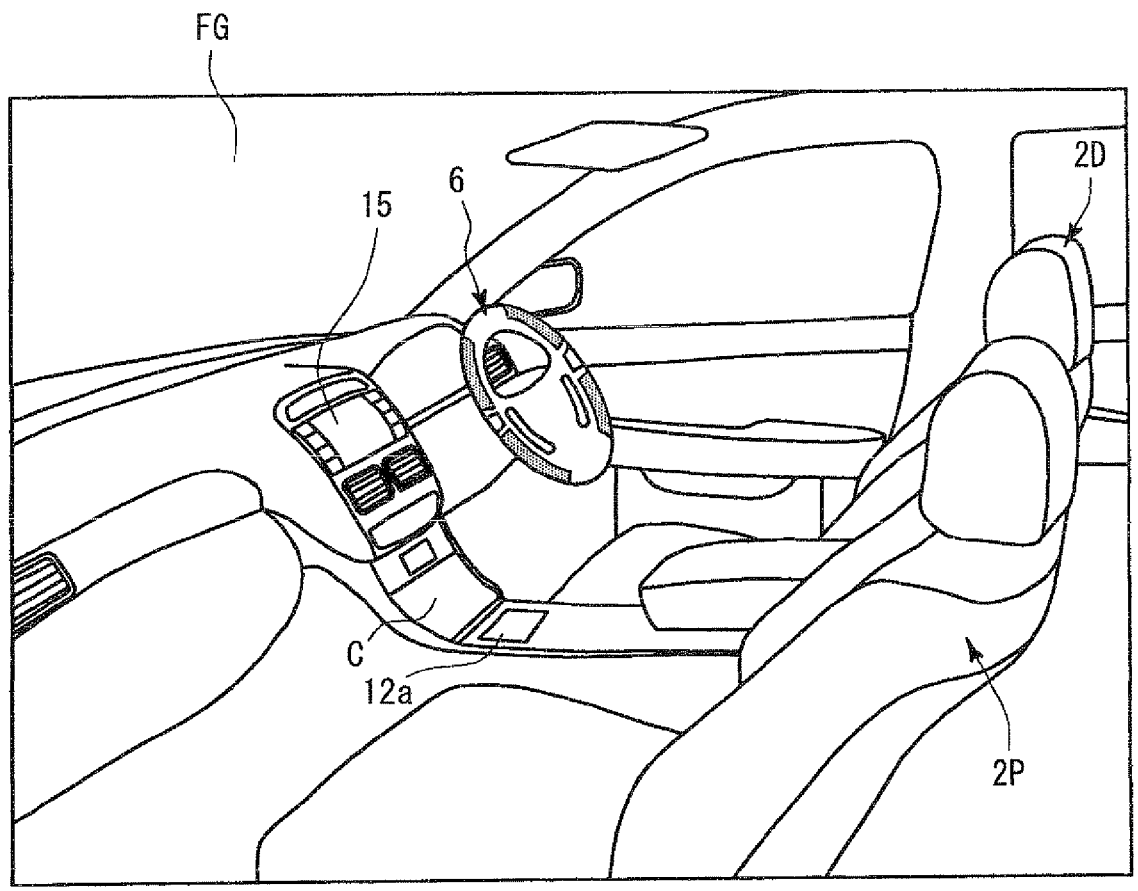
FIG. 2 is a perspective view showing a vehicle interior provided with the vehicular image overlaying input apparatus.

As shown in FIG. 2, the operation information input part 12 according to the embodiment is provided for a center console C of the vehicle or a position that is below a windshield FG of the vehicle and is operable from the adjacent left and right seats. Further, the operation information input part 12 is provided below the display apparatus 15 between both bottoms of the adjacent left and right seats toward the vehicle front.

Figure 7:
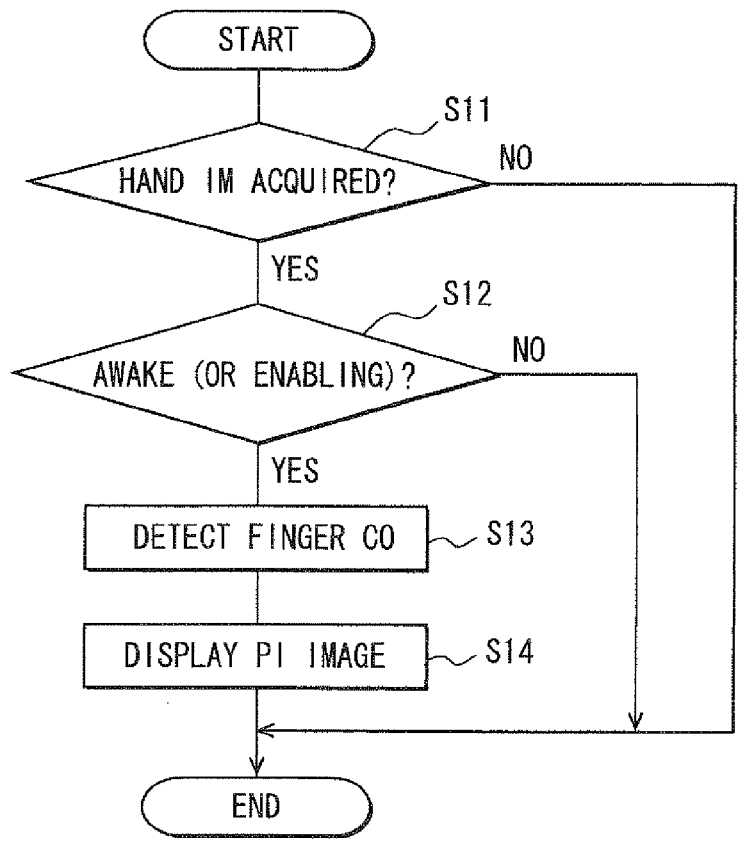
FIG. 7 is a flow chart showing a process of displaying a position indication image.

According to the embodiment, the adjacent left and right seats are equivalent to a driver's seat 2D and a passenger seat 2P in FIG. 7.

Now returning back to FIG. 1, the display apparatus 15 provides color capabilities and, as shown in FIG. 2, is positioned toward the vehicle front ahead of occupants sitting on the driver's seat 2D and the passenger seat 2P so that both occupants can view the screen of the display apparatus 15. The display apparatus 15 may use a liquid crystal display, a plasma display, or an organic EL display.

The display apparatus 15 includes a display surface for operating devices provided for the vehicle. The display surface according to the embodiment functions as a tactile operation part used for tactile operations. Specifically, the display surface is provided with a touch panel 15a so as to function as the tactile operation part. The touch panel 12a of the operation information input part 12 is provided as a remote operation part so as to remotely operate the touch panel 15a from a position nearer to the driver or the passenger on the passenger seat. A touch operation is performed on the touch operation panel (also referred to as a remote operation surface) 12a1. The control circuit 18 accepts input to the screen position on the display apparatus 15 corresponding to the position of the touch operation. Specifically, a two-dimensional coordinate system is defined on the display screen of the display apparatus 15, namely, on the touch operation panel of the touch panel 15a. Another two-dimensional coordinate system is defined on the touch operation panel 12a1 of the operation panel 12a. A unique correspondence relation is predetermined between both two-dimensional coordinate systems. The position in one coordinate system is uniquely specifiable in the other coordinate system. When a touch operation is performed on the touch operation panel 12a1, the input operation is accepted based on the correspondence relation. The position coordinate for the touch operation corresponds to the position coordinate on the display screen of the display apparatus 15. The display apparatus 15 can function as a driver awakening means and a disabled operation notification means.

The display apparatus 15 may be placed not only within the center console C as shown in FIG. 2 but also above the lower edge of the windshield FG, for example. Examples of the display apparatus 15 may include a head up display (HUD) for displaying the above-mentioned image or data on the windshield FG of the vehicle and a meter display apparatus positioned toward the bottom of a steering wheel 6.

Now returning back to FIG. 1, the voice input/output device 16 is capable of outputting voice data for facility guidance and various information supplied from the map data input device 14 and voice data for reading out information acquired through the interface 19. The voice input/output device 16 includes a microphone and a known voice recognition unit though not shown and is capable of supplying the control circuit 18 with a command equivalent to voice of an operator such as a driver. The voice input/output device 16 can function as the driver awakening means and the disabled operation notification means.

The LAN interface 19 provides an interface circuit for interchanging data with the other onboard electronic devices and sensors through the interior LAN 50. The LAN interface 19 may be used to incorporate data from the other ECUs 101, 201, 301, 401, and so on and the unawakened state detection part 70.

The control circuit 18 is mainly configured as a known microcomputer including a known but not-shown CPU, ROM, RAM, an input/output device, and a bus line connecting these components. The control circuit 18 provides various controls related to known navigation functions based on a program stored in a storage part such as the ROM.

The control circuit 18 includes the image processing part 18a. Based on a program stored in the storage part such as the ROM, the image processing part 18a displays the main image 160B such as the map manipulation image so as to be combined or overlaid with a sub-image The sub-image includes the switch image (operation icon) 160I and a position indication image 160H based on a hand image 150H acquired from the operation information input part 12. For example, let us suppose that the operator such as the driver moves his or her finger opposite to the touch operation panel 12a1 of the operation panel 12a. The display screen of the display apparatus 15 displays a position indication image 160H or a processed image reflecting the hand or finger shape so that the displayed image moves accordingly. The operator can operate the operation panel 12a as if it were placed on the display screen of the display apparatus 15.

The control circuit 18 functions as an operation disabling means, an input accept means, an operation position setup means, a position indication image display means, and a display mode setup means.

The above-mentioned navigation system 10 functions as a main control part for the input apparatus 1 as an image overlaying operation apparatus. The above-mentioned navigation system 10 can acquire a result of detecting the unawakened state from the unawakened state detection part 70.

Figure 4:
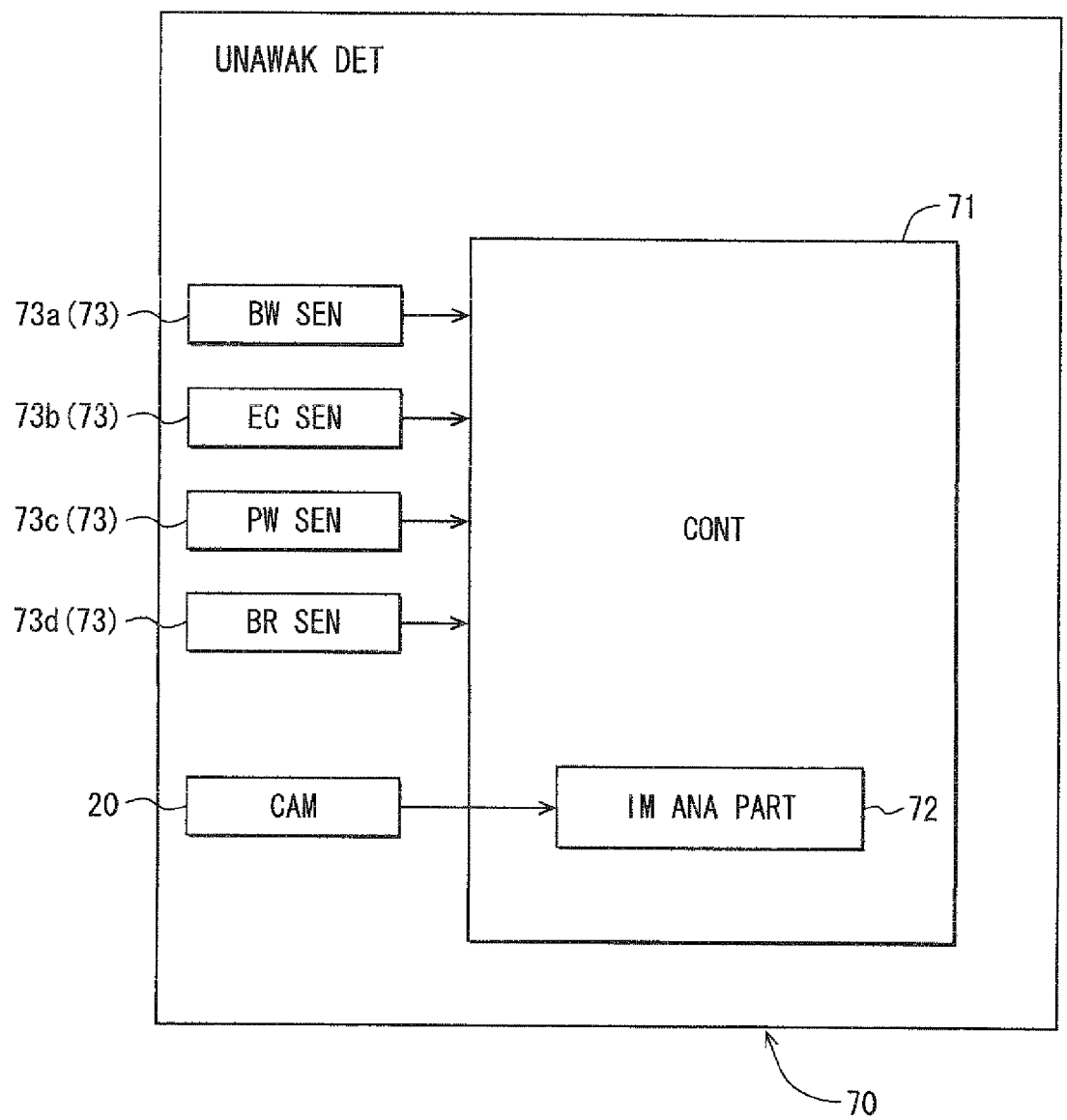
FIG. 4 is a block diagram showing a configuration of an unawakened state detection part.

As shown in FIG. 4, the unawakened state detection part 70 includes a control part 71, a sensor part 73, a camera 20, and an image analysis part 72. The unawakened state detection part 70 identifies an awakened or unawakened state of an occupant based on a detection result from the sensor part 73 and a result of analyzing an image captured by the camera 20.

Figure 5A:
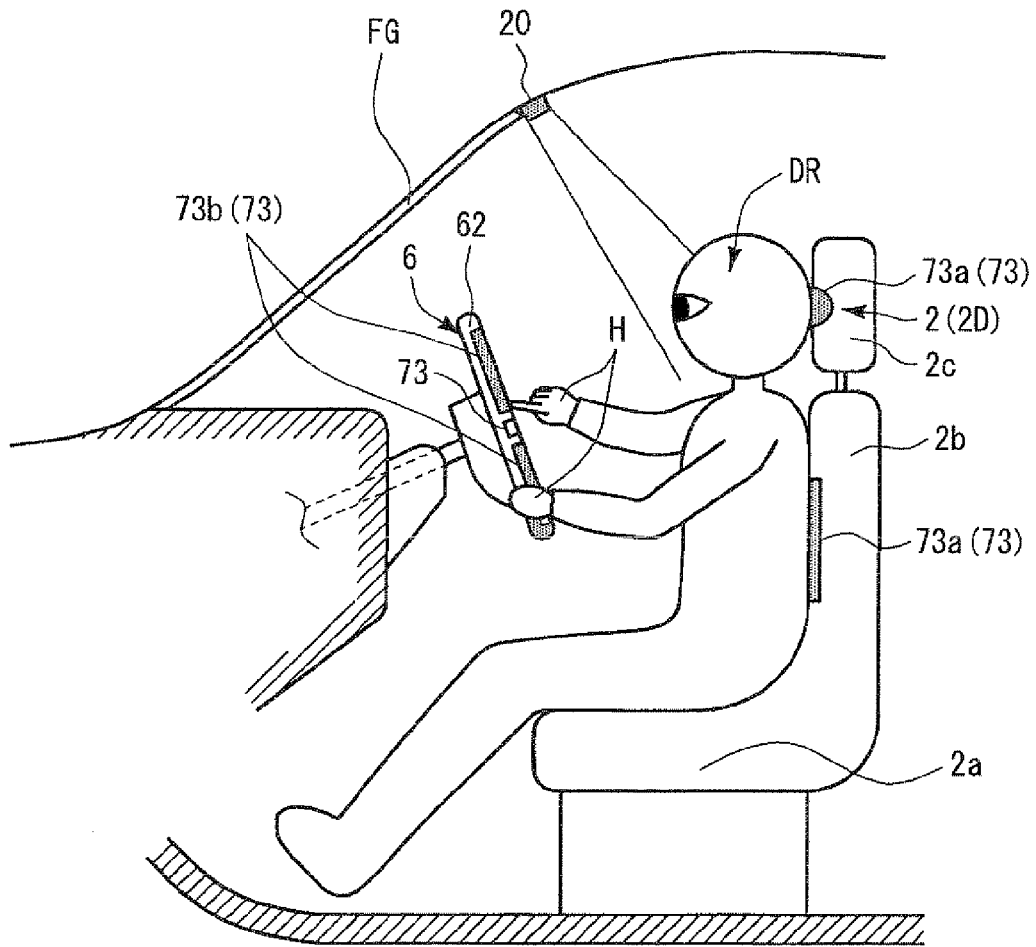
FIGS. 5A and 5B show arrangement of sensors in a vehicle interior.
Figure 5B:
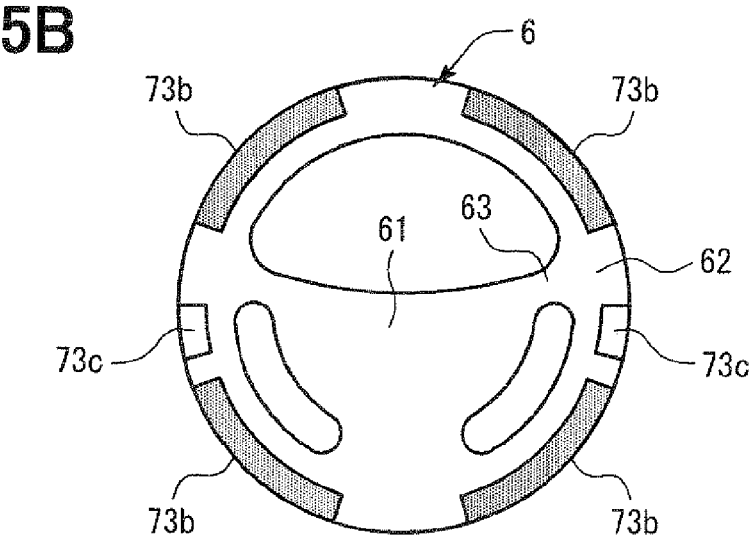

The sensor part functions as a biological information acquisition means. As shown in FIG. 5, the sensor part provides a biological waveform detection sensor (biological waveform detection means). Each of the sensors 73a through 73d acquires a biological waveform signal from a vehicle occupant sitting on a bottom 2a of a seat 2. The biological waveform signal is equivalent to any of a brain wave, a pulse wave, a breathing, and a heartbeat. The biological waveform detection sensors 73a through 73d are provided for vehicle parts capable of being in contact with a vehicle occupant sitting on the seat during driving. According to the embodiment, as shown in FIG. 5, a headrest 2c of the seat 2 is provided with an electrode (brain wave sensor) 73a for detecting a brain wave signal. A reclining backrest 2b of the seat 2 is provided with a piezoelectric film sensor (breathing sensor) 73d for detecting a biological back signal containing components of a pulse wave signal and a breathing signal. A ring 62 of the steering wheel 6 is provided with an electrode (electrocardiographic sensor and heartbeat sensor) 73b for detecting an electrocardiographic signal and a heartbeat signal. The ring 62 is also provided with a pulse wave sensor 73c for detecting a pulse wave signal. The sensors 73 provided for the steering wheel 6 are attached to the ring 62 held during driving, not to a boss 61 or a spoke 63, for effectively collecting biological waveform signals.

A control section 71 acquires detected signals (biological information) from the sensors 73a through 73d. Based on the signals, the control section 71 determines whether or not the occupant on the seat 2 corresponding to the sensors 73a through 73d shows a predetermined unawakened state that differs from a normal awakened state.

The vehicular input apparatus 1 according to the embodiment has the above-mentioned configuration and allows the unawakened state detection part 70 to acquire biological information about the vehicle occupant (biological information acquisition means). Based on the acquired biological information, the vehicular input apparatus 1 detects that the vehicle occupant shows the predetermined unawakened state different from the normal awakened state (unawakened state detection means). The detection result is transmitted to the control circuit 18 of the navigation system 10. Based on the detection result, the control circuit 18 determines the awakened state of the vehicle occupant. When the unawakened state is detected, the control circuit 18 disables operations on a specified operation part (operation disabling means), making it possible to prevent an incorrect operation on the operation part.

The embodiment aims at only a driver as an occupant whose awakened or unawakened state is to be detected. The sensors 73 of the unawakened state detection part 70 are attached only to the driver's seat 2D. The camera 20 only captures the driver. The prevention against incorrect operations is targeted for the operation part fixed to a position where at least a vehicle driver can access. More specifically, that prevention is targeted for a near-occupant operation part fixed to a position where the driver can access while sitting on the driver's seat 2D. According to the embodiment, the prevention against incorrect operations is targeted for the operation panel 12a configured as a remote operation part.

The operation panel 12a is prevented against incorrect operations and is used with an operation panel 15a as a main operation part that is independently provided for the display apparatus 15. The operation panel 12a functions as a remote operation part capable of remote operations on the main operation part 15a. More specifically, the operation panel 12a is capable of input operations on the other onboard electronic devices such as an air conditioner 100, a power window system 200, an audio system 300, and a seat adjusting system 400 having a seat adjusting function. The operation panel 12a is used with operation parts 140, 240, 340, and 440 there of as main operation parts. The operation panel 12a may be also defined as a remote operation part capable of remote operations on the main operation parts 140, 240, 340, and 440. The main operation parts 15a, 140, 240, 340, and 440 as a driving part are fixed to positions farther away from the driver as an operator than the operation panel 12a as the remote operation part. The main operation parts are less accessibly located than the remote operation part.

Figure 6:
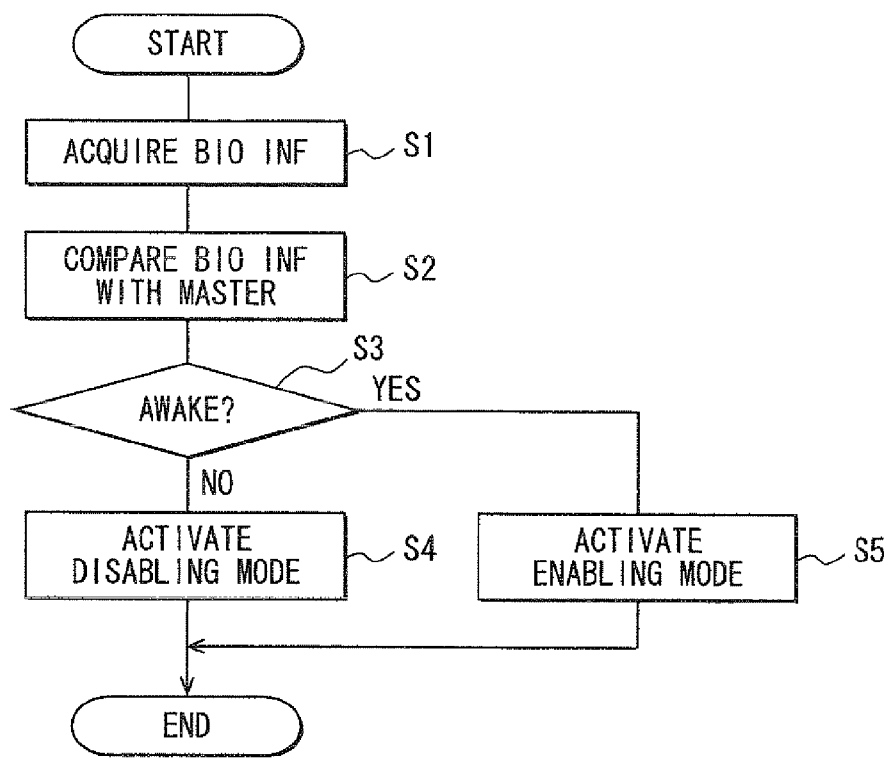
FIG. 6 is a flow chart showing an input operation restriction process.

With reference to FIG. 6, the following describes an input operation restriction process on the operation panel 12a as a remote operation part. The process is performed when the CPU executes a program stored in a specified storage of the control circuit 18.

At S1 and S2, the control circuit 18 allows the unawakened state detection part 70 to acquire detection results from the sensors 73 and a capture result (captured image) from the camera 20. Specifically; in S1, biological information of a driver during driving is acquired. In S2, the acquired biological information is compared with master information. Base on the detected result information, the control circuit 18 allows the unawakened state detection part 70 to detect the driver's current awakened or unawakened state. The unawakened state detection part 70 detects the awakened or unawakened state based on the result information in accordance with a detection method to be described later. At S3, the control circuit 18 acquires detection result information from the unawakened state detection part 70 whether the driver is in an awakened state. The process proceeds to S4 when the driver is assumed to indicate the unawakened state. The process proceeds to S5 when the driver is assumed not to indicate the unawakened state.

At S4, the control circuit 18 activates an operation disabling mode that disables input operations on the operation panel 12a as the remote operation part. Further, the control circuit 18 activates a display disabling mode that inhibits a position indication image from being displayed on the display screen (operation mode setup means and display mode setup means). Thus, in S4, the operation disabling mode and the display disabling mode are activated. At S5, the control circuit 18 activates an operation enabling mode that enables input operations on the operation panel 12a as the remote operation part. Further, the control circuit 18 activates a display enabling mode that permits a position indication image to be displayed on the display screen (operation mode setup means and display mode setup means). Thus, in S5, the operation enabling mode and the display enabling mode are activated. Once activated, the operation mode and the display mode are stored in an operation mode storage part and a display mode storage part, that is, specific storage areas in specific storage parts of the control circuit 18.

The process terminates upon completion of S4 or S5. After termination, the process is repeated at a specified cycle. The control circuit 18 changes the above-mentioned modes in accordance with the detected awakened or unawakened state.

The control circuit 18 functions as an operation mode setup means and the display mode setup means by performing the input operation restriction process.

With reference to FIG. 7, the following describes a process of displaying a position indication image on the display apparatus 15. The process is performed when the CPU executes a program stored in a specified storage of the control circuit 18.

At S11, the control circuit 18 acts on an image captured by the camera 12b and determines whether or not to capture an image of the operator's hand. The camera 12b always captures an approaching object H (e.g., a hand of the operator such as the driver) that approaches the touch operation panel 12a1. The captured image is always input to the image processing part 18a of the control circuit 18. The image processing part 18a uses a known image analysis technology to analyze the input captured image and extracts an approaching object image 150H based on a color difference or the like. The image processing part 18a recognizes the shape of the extracted approaching object image 150H and determines whether or not the image 150H represents a human hand image. Thus, in S11, the control circuit 18 determines whether the hand image is acquired. A determination result is output to the control circuit 18. The process proceeds to S12 when it is determined that the hand image is recognized. Otherwise, the process terminates.

At S12, the control circuit 18 determines whether or not the driver currently shows the awakened state. In other words, the control circuit 18 determines whether or not the display mode is currently set to the display enabling mode. The current display mode is stored in the specified storage area (display mode storage part) of the control circuit 18. The control circuit 18 reads the stored display mode for the determination. The process proceeds to S13 when the display enabling mode (awakened state) is active.

Figure 9A:
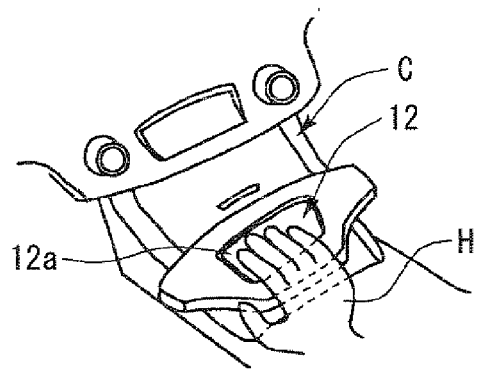
FIGS. 9A to 9C illustrate a first example of capturing a hand against an operation panel.
Figure 9B:
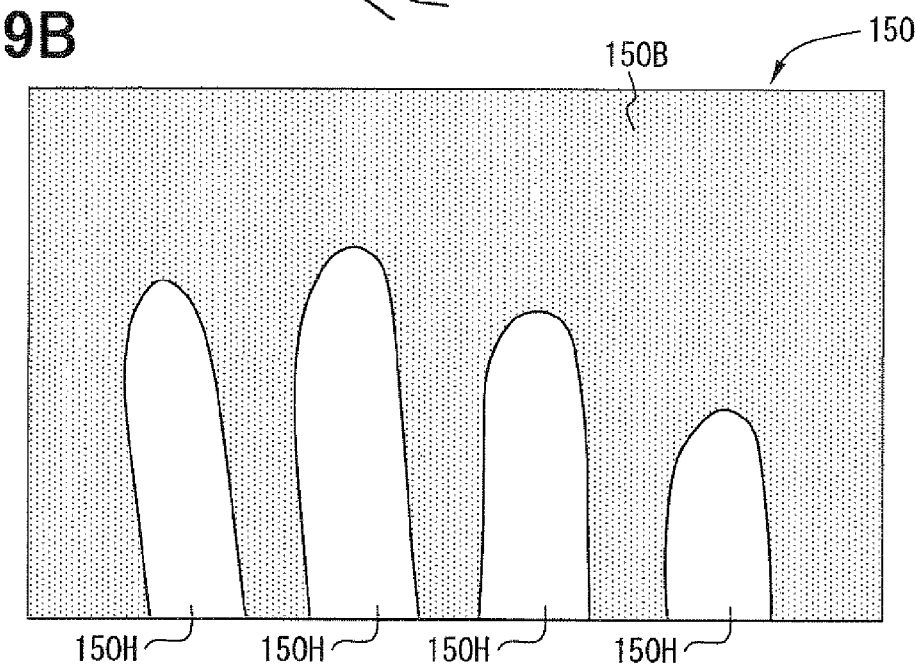
Figure 10A:
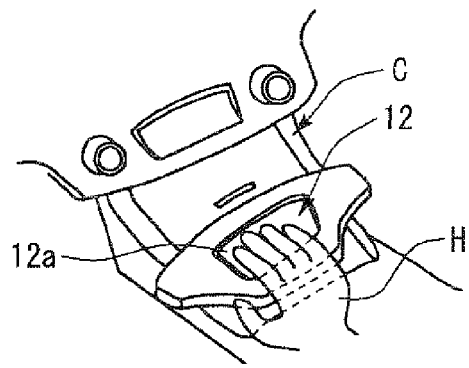
FIGS. 10A to 10C illustrate a second example of capturing a hand against an operation panel.
Figure 10B:
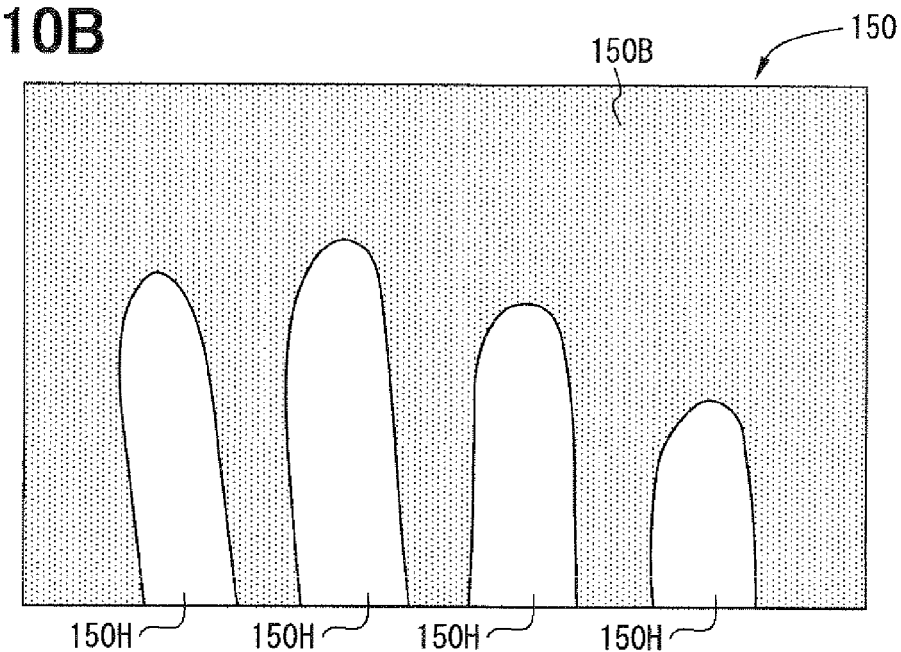
Figure 11A:
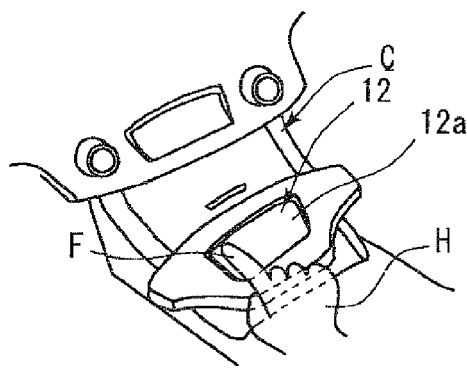
FIGS. 11A to 11C illustrate a third example of capturing a hand against an operation panel.
Figure 11B:
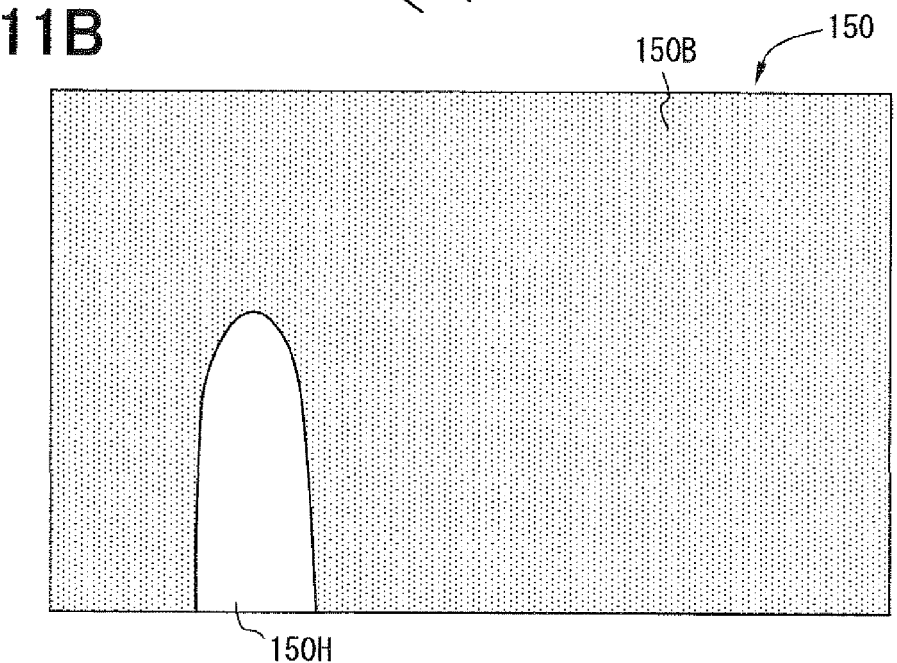

At S13, the control circuit 18 specifies an indicating position on the touch operation panel 12a1. More specifically, the image processing part 18a extracts the hand image at S11. From the entire shape of the hand image, the control circuit 18 locates a finger by identifying an approximately linear, rod-like image pattern having an axis line as long as a specified length or longer. The control circuit 18 further locates a fingertip position from the located finger. According to the embodiment, the touch operation panel 12a1 is positioned to an operation panel image area. The control circuit 18 specifies the operation panel image area on the captured image captured by the camera 12b. The control circuit 18 also settles an operation coordinate system for the touch operation panel 12a in the operation panel image area. The control circuit 18 then locates the fingertip position in the settled operation coordinate system. According to the embodiment, the captured image 150 (binarized image) in FIGS. 9B, 10B, and 11B is equivalent to the operation panel image area that capture the whole of the touch operation panel 12a1. Thus, in S13, a finger coordinate is detected.

Figure 9C:
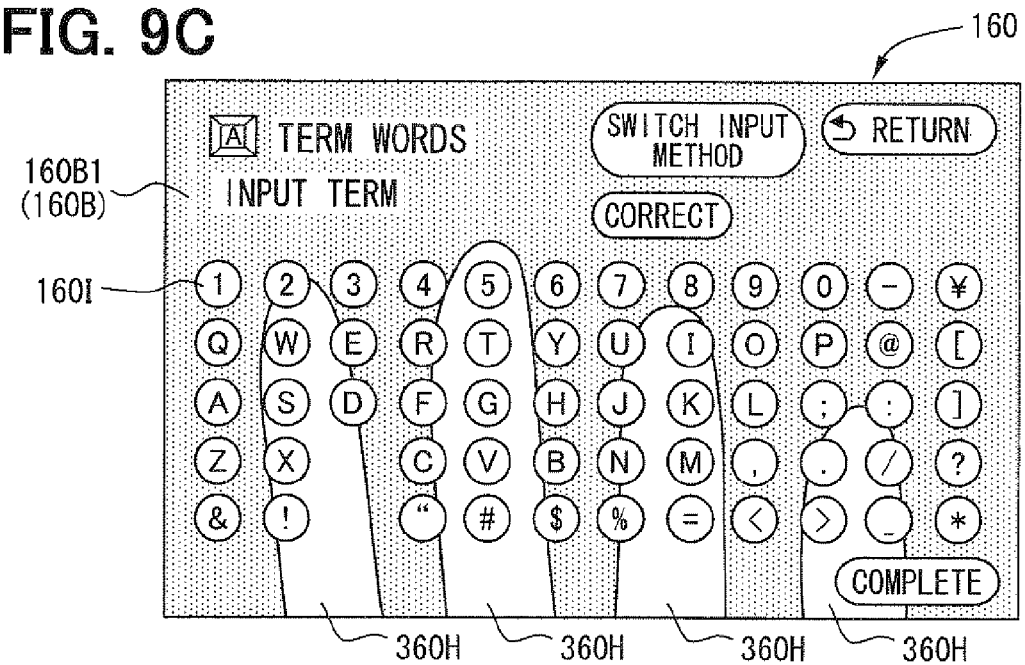
Figure 11C:
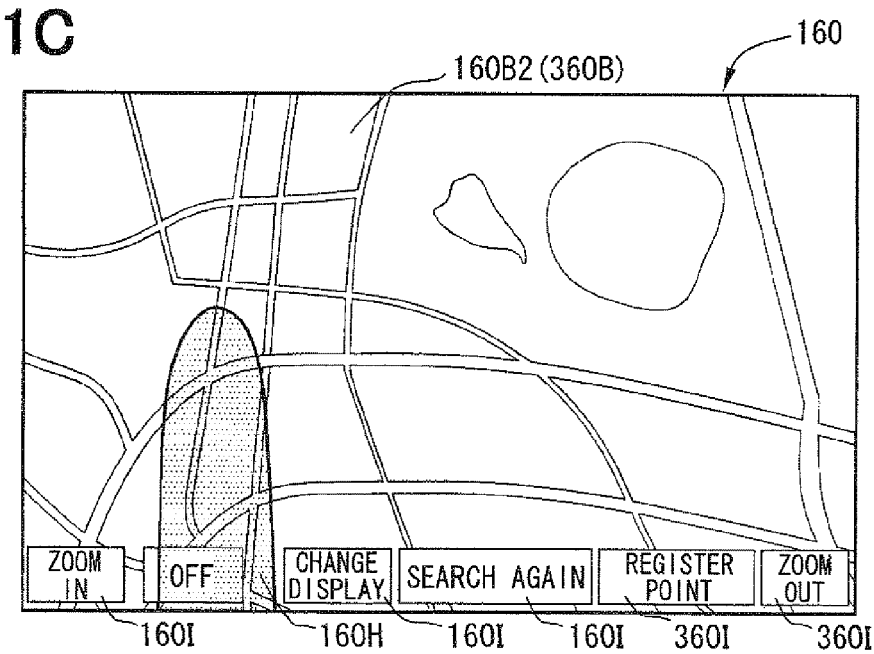

At S14, the control circuit 18 displays a position indication image 160H at the fingertip position on the display screen of the display apparatus 15 as shown in FIGS. 9C and 11C (position indication image display means). The fingertip position is specified on the operation panel image area. The control circuit 18 specifies a position on the display screen of the display apparatus 15 corresponding to the fingertip position specified at S13 in the operation coordinate system. The display screen is provided with a display coordinate system that corresponds to the operation coordinate system. The control circuit 18 displays the position indication image 160H on the display screen so as to specify a position coordinate in the display coordinate system corresponding to the fingertip coordinate position in the operation coordinate system and locate the position coordinate.

Figure 10C:
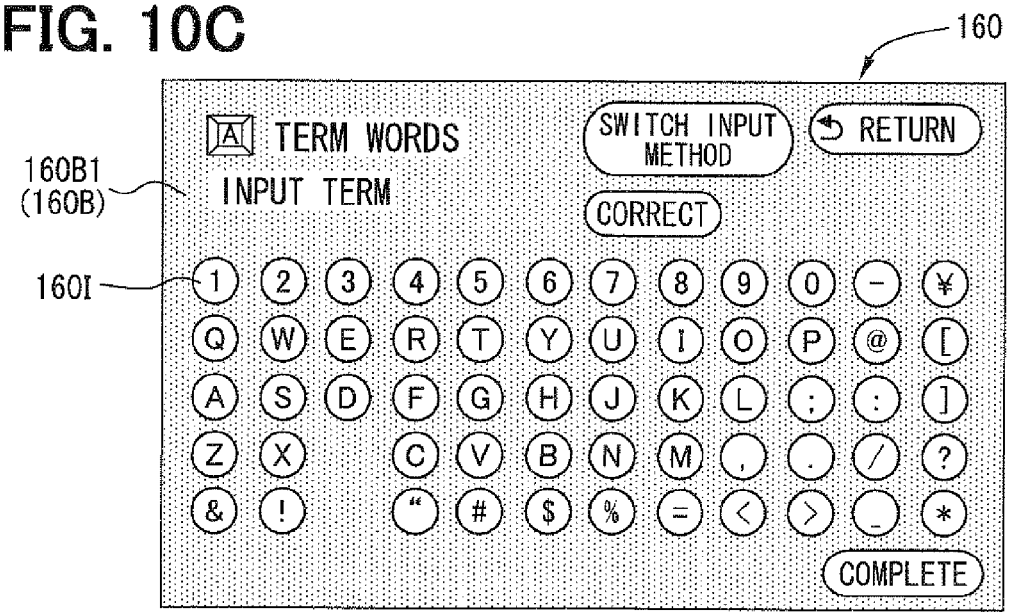

The process terminates when the display disabling mode (unawakened state) is assumed to be active at S12. In this case, the control circuit 18 does not display position indication image 160H at S13 and S14. The position indication image 160H is not displayed on the screen of the display apparatus 15 as shown in FIG. 10C.

The process terminates upon completion of S13 and S14. After termination, the process is repeated at a specified cycle. While the display enabling mode takes effect, moving the hand or finger opposite to the operation panel 12a accordingly moves the display position of the position indication image 160H (processed image) displayed on the display screen of the display apparatus 15.

The control circuit 18 functions as the position indication image display means by performing the process of displaying the position indication image.

Figure 8:
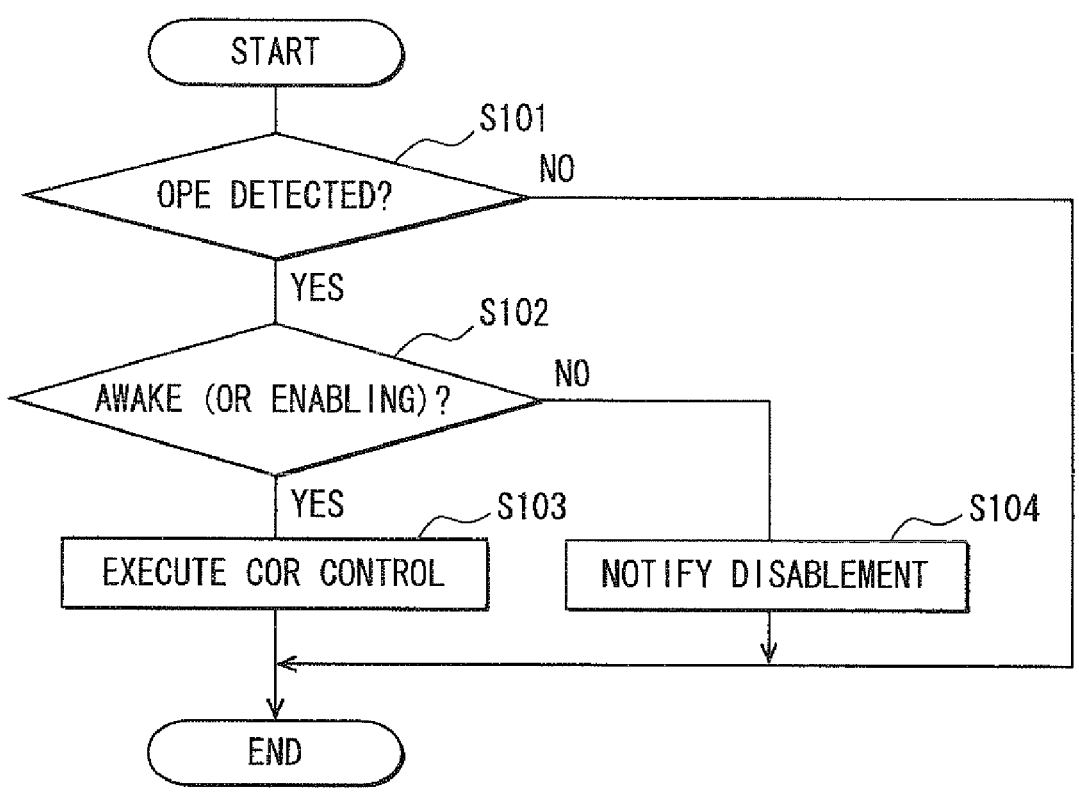
FIG. 8 is a flow chart showing an input operation process.

With reference to FIG. 8, the following describes an input operation process on the operation panel (remote operation part) 12a of the operation information input part 12.

At S101, the control circuit 18 determines whether or not a touch operation is performed on the operation panel 12a. The operation panel 12a is configured as a touch panel. A touch operation allows a corresponding operation signal to be supplied to the control circuit 18. The control circuit 18 determines the presence or absence of the input operation signal. The process proceeds to S102 when a touch operation is detected on the operation panel 12a. Otherwise, the process terminates.

At S102, the control circuit 18 determines whether or not the driver currently shows the awakened state. In other words, the control circuit 18 determines whether or not the operation mode is currently set to the operation enabling mode. The current operation mode is stored in the specified storage area (operation mode storage part) of the control circuit 18. The control circuit 18 reads the stored current input operation mode for the determination. The process proceeds to S103 when the operation enabling mode (awakened state) is active.

At S103, the control circuit 18 provides or executes control corresponding to the touch operation position on the operation panel 12a. Specifically, the control circuit 18 first specifies a touch operation position on the touch operation panel 12a1 of the operation panel 12a. The operation panel 12a is configured as a touch panel. A touch operation inputs an operation signal to the control circuit 18. The operation signal reflects touch operation position information, namely, coordinate information in an operation coordinate system predetermined for the operation surface 12a1. Based on the operation signal, the control circuit 18 specifies the coordinate position corresponding to the touch operation. The control circuit 18 then provides control corresponding to the touch operation position on the operation panel 12a. Positions on the touch operation panel 12a1 of the operation panel 12a correspond to those on the surface of a display screen 15. The control circuit 18 specifies a position on the display screen 15 corresponding to the position specified at S103 on the touch operation panel 12a1. The control circuit 18 performs a control content corresponding to the specified screen position. Specifically, the control circuit 18 outputs a control signal for performing the control content. For example, let us suppose that the position on the touch operation panel 12a1 specified at S103 corresponds to a position for a switch image 160I displayed on the display screen 15. The control circuit 18 outputs a control signal for performing the control content assigned to the switch image.

The process proceeds to S104 when the operation disabling mode (unawakened state) is assumed to be active at S102. At S104, unlike S103, the control circuit 18 does not perform the control content corresponding to the operation. Instead, the control circuit 18 notifies the operator that the operation is disabled and the control content is not performed (disabled operation notification means). The control circuit 18 notifies that the operation disabled the input.

Specifically, the control circuit 18 disables the input operation to modify part or all of the display state on the screen of the display apparatus 15. In this manner, the control circuit 18 notifies the driver of the disabled input operation. According to the embodiment, the notification content is literally displayed along with an audible alarm output from the voice input/output device 16. Another method of notification output may display a switch image 200H corresponding to the input operation position on the touch operation panel 12a1 by changing the display state before the input operation. For example, the control circuit 18 may display the operated switch image 200H by increasing the size and changing the color, the shape, or the blinking state so as to differ from the equivalents before the input operation. Display images for representing these changes are stored in a specified storage area of the control circuit 18. The stored images are read as needed and are used for the display. Thus, in S104, the size of the switch image is enlarged, the color is changed, the shape is changed, or the image is blinked so that the control circuit notifies the driver of the disablement of operation.

The process terminates upon completion of S103 or S104. After termination, the process is repeated at a specified cycle.

The control circuit 18 functions as the operation disabling means and the disabled operation notification means by performing the input operation process.

The following describes in detail the operation information input part 12.

As shown in FIG. 3, the operation panel 12a is embedded in a front end opening of a hollow frame 12f. The surface 12a1 is configured as a touch operation panel (remote touch operation panel). The front end opening is formed in a front end part 121e of the frame. An outer edge of the front end part 121e is provided with a cylindrical wall part 122e toward the rear. The rear end part is fixed to a circuit substrate 12f. The frame 12f is fixed to a specified position of the vehicle compartment. The frame 12f internally contains the camera 12b and the light source 12c.

As shown in FIG. 3, the light source 12c radiates light so as to illuminate the operation panel 12a from a second surface 12a2 to a first surface 12a1. The light (radiated light) from the light source 12c is transmitted from the touch operation panel 12a1 to the outside unless an approaching object such as a hand is positioned so as to cover the touch operation panel 12a1. When the approaching object H is positioned opposite to the touch operation panel 12a1, the light (radiated light) reflects on the approaching object H. Part of the light returns to the second surface 12a2 and is captured by the camera 12b.

The camera 12b captures the approaching object H from the second surface 12a2 of the operation panel 12a so as to detect the reflected light that is radiated from the light source 12c and is reflected on the approaching object H. The camera 12b is fixed to the vehicle so as to capture a predetermined capture range. Specifically, the camera 12b captures a reflecting surface of a reflective member 12r. The components are arranged so that the capture range is included in an image (reflected image) projected on the reflecting surface. The camera 12b may directly capture the capture range when the reflective member 12r is unavailable. In such case, the captured image needs to be horizontally flipped.

The light source 12c according to the embodiment represents an infrared light source. Specifically, the light source 12c is an LED positioned at the rear on the second surface of the operation panel 12a. The camera 12b according to the embodiment represents an infrared camera suitable for capturing in darkness. The camera 12b is provided with an unshown infrared filter that eliminates visible light and is used for capturing. During a capturing process, the infrared light source 12c radiates light (infrared ray). The light reflects on the approaching object H. The camera 12b captures the reflected light. The camera 12b is fixed to the substrate that is fixed to the vehicle. The capture range contains the touch operation panel 12a1. The operation panel 12a according to the embodiment is made of a material that transmits only the light from the light source 12c. The embodiment eliminates an infrared filter from the camera 12b. The inside of the frame 12f is invisible from outside.

The camera 12b according to the embodiment functions as an approaching object capturing means for capturing an approaching object that approaches the operation panel 12a. Considering that the approaching object contains a hand, the camera 12b may also function as a hand image capturing means for capturing an image of the hand.

FIGS. 9A to 9C through 11A to 11C illustrate capturing a hand H opposite to the operation panel 12a. FIGS. 9A and 10A show states of the hand (finger) opposite to the operation panel 12a and its surface 12a1. FIGS. 9B and 10B show a video 150 of the hand (finger) captured by the camera 12b while keeping the states as shown in FIGS. 9A and 10A. The video 150 covers the whole of the operation panel 12a as a capturing area. The embodiment provides to binarize a captured video to generate the video 150 as shown in FIGS. 9B and 10B. In FIGS. 9B and 10B, reference numeral 150H denotes an area where the approaching object H is captured. Reference numeral 150B denotes an area where nothing is captured. The area 150B may be considered to display the operation panel 12a. However, the area 150B displays nothing because the operation panel 12a transmits the light from the light source 12c. Nevertheless, the area 150B could display the background such as a vehicle ceiling according to the embodiment through the operation panel 12a. The amount of captured reflected infrared ray may be too small to generate a video. Alternatively, some amount of reflected infrared ray may be captured but assimilated into the background as a result of binarization. FIGS. 9C and 10C show example screen displays on the display apparatus 15 when the video 150 in FIGS. 9B and 10B is captured. According to the embodiment, however, the screen in FIG. 10C may be displayed instead of the screen in FIG. 9C when the video 150 in FIG. 9B is generated.

The following describes in detail the display of the position indication image 160H according to the embodiment.

According to the embodiment, the approaching object image 150H represents a hand. The processed image 160 is generated based on the captured image 150H of the hand. The processed image 160 is used as a position indication image so as to be overlaid on the position located by the hand (fingertip) on the display screen.

According to the embodiment, the processed image 160H based on the approaching object image 150H is processed and generated so as to reflect the external shape of the approaching object image 150H. The image 160H is overlaid on the main image 160B. Instead, the image 160H may be combined with the main image 160B.

The position indication image 160H may not necessarily reflect the outline of the captured hand or finger shape. The image just needs to indicate at least the position indicated by the captured finger. The image may be replaced by a symbolic image such as a pointer. The position indication image 160H may use an unprocessed version of the hand or finger image 150H captured by the camera 12b for overlaid or combined display. However, such unprocessed image may hide an overlapping part of the main image 160B. In consideration for this, it may be preferable to apply a process such as alpha blending to the captured image for improved operability.

The embodiment provides to use the light source 12c. The camera 12b receives reflected light from the light source 12c for capturing. Consequently, the reflected light intensity is associated with the color gradation in the captured video 150. A high reflected light intensity causes a high gradation level. The camera 12b according to the embodiment generates the multi-tone video 150 that is monochrome in the embodiment. The image processing part 18a uses a predetermined gradation threshold to binarize gradation levels of pixels as shown in FIGS. 9B, 10B, and 11B. When an area exceeds the gradation threshold, the image processing part 18a extracts that area as the approaching object image 150H. The image processing part 18a recognizes the hand or finger image from the extracted approaching object image 150H as follows. The image processing part 18a compares the shape of the approaching object image 150H with a hand shape pattern stored in the storage part of the control circuit 18. The image processing part 18a recognizes and identifies the approaching object image 150H matching the pattern as a hand image.

The following describes operations of the unawakened state detection part 70 according to the embodiment.

A brain wave sensor 73a detects a brain wave signal while an occupant sits on a specified seat 2 with his or her head contact with or close to the brain wave sensor 73a. The control section 71 receives the brain wave signal detected by the brain wave sensor 73a. The control section 71 then applies known signal and waveform processes to the brain wave signal. The control section 71 analyzes the brain wave as is well known to identify the unawakened state of the occupant sitting on the seat 2. To do this, the control section 71 extracts and amplifies an alpha wave and a theta wave contained in the brain wave signal. The control section 71 compares a signal reflecting these waves with a corresponding reference signal. The embodiment determines an unawakened state in which the alpha wave disappears and the theta wave appears. The alpha wave is assumed to disappear when an alpha wave amplitude continues to remain under a reference level for a specified period. The theta wave is assumed to disappear when a theta wave amplitude continues to exceed a reference level for a specified period. The embodiment defines the unawakened state in accordance with not only REM sleep and non-REM sleep but also a predicted drowsy state (expected drowsy state) to be detected during transition from the awakened state to the non-REM sleep. Reference signals equivalent to the above-mentioned reference levels are configured so that the unawakened state includes the predicted drowsy state.

An electrocardiographic sensor 73b includes multiple electrodes provided for the ring 62 of the steering wheel 6. The electrocardiographic sensor 73b detects an electrocardiographic signal when the driver holds two different electrodes. The electrocardiographic signal is input to the control section 71. The control section 71 applies known signal and waveform processes to the electrocardiographic signal to generate a rectangular pulse signal (heartbeat signal) synchronized with the heartbeat. The control section 71 stores a heartbeat interval based on the heartbeat signal and analyzes the interval. It is known that the number of heartbeats decreases during sleep. In the embodiment, the control section 71 extracts and amplifies a heartbeat signal reflecting the heartbeat contained in the electrocardiographic signal. The control section 71 counts the number of heartbeats based on the heartbeat signal. The number of heartbeats is counted within a specified reference time such as one minute. The control section 71 compares the counted number of heartbeats with a reference heartbeat count. The control section 71 detects an unawakened state when the counted number of heartbeats continues to be smaller than the reference heartbeat count during the specified period. The reference heartbeat count is settled so that the unawakened state is defined in accordance with not only REM sleep and non-REM sleep but also a predicted drowsy state (expected drowsy state) to be detected during transition from the awakened state to the non-REM sleep. In the embodiment, the reference heartbeat count is settled by adding an offset to the number of heartbeats that is measured in advance during a normal condition.

The pulse wave sensor 73c is provided for part of the steering wheel 6 or for the ring 62 according to the embodiment. The pulse wave sensor 73c according to the embodiment represents a known optical reflective sensor including a light emitting element such as a light emitting diode and a light receiving element such as photodiode. Let us suppose that the light emitting element radiates light to a human body such as a hand holding the steering wheel. The light is partly applied to small and smaller arteries (capillary arteries) flowing through the human body. The light is absorbed in hemoglobin in the blood flowing through small and smaller arteries. The remaining light is reflected on small and smaller arteries to scatter and partly enters the light receiving element. The pulsating blood pulsatingly varies the amount of hemoglobin in the small and smaller arteries. The light absorbed in the hemoglobin also varies pulsatingly. As a result, a change is made to the light that is reflected on the small and smaller arteries and is detected by the light receiving element 13. The pulse wave sensor 73c outputs a pulse wave signal (e.g., voltage signal) that represents the change in the amount of light received. The control section 71 receives the supplied pulse wave signal. The control section 71 applies known signal and waveform processes to the pulse wave signal to generate a rectangular pulse signal (pulse signal) synchronized with the pulse. The control section 71 stores a pulse interval based on the pulse signal and analyzes the interval. It is known that the pulse rate decreases during sleep. In the embodiment, the control section 71 extracts and amplifies a pulse signal capable of counting pulses from the pulse wave signal. The control section 71 counts the pulse rate based on the pulse signal. The pulse rate is equivalent to the number of heartbeats and is counted within a specified reference time such as one minute. The control section 71 compares the counted pulse rate with a reference pulse rate. The control section 71 detects an unawakened state when the counted pulse rate continues to be smaller than the reference pulse rate during the specified period. The reference pulse rate is settled so that the unawakened state is defined in accordance with not only REM sleep and non-REM sleep but also a predicted drowsy state expected drowsy state) to be detected during transition from the awakened state to the non-REM sleep. In the embodiment, the reference pulse rate is settled by adding an offset to the pulse rate that is measured in advance during a normal condition.

The pulse wave sensor 73c as a breathing sensor represents a piezoelectric film sensor that is provided for the reclining backrest 2b of the seat 2. The control section 71 receives a biological back signal that is detected and supplied from the pulse wave sensor 73c as a breathing sensor. The control section 71 applies known signal and waveform processes to the biological back signal to generate a breathing signal capable of counting the number of breaths. The control section 71 stores a breathing interval based on the breathing signal and analyzes the interval. It is known that the number of breaths decreases during sleep. In the embodiment, the control section 71 extracts and amplifies a breathing signal capable of counting the number of breaths from the biological back signal. The control section 71 counts the number of breaths based on the breathing signal. The number of breaths is related to the number of heartbeats and is counted within a specified reference time such as one minute. The control section 71 compares the counted number of heartbeats with a reference breathing count. The control section 71 detects an unawakened state when the counted number of breaths continues to be smaller than the reference breathing count during the specified period. The reference breathing count is settled so that the unawakened state is defined in accordance with not only REM sleep and non-REM sleep but also a predicted drowsy state (expected drowsy state) to be detected during transition from the awakened state to the non-REM sleep. In the embodiment, the reference breathing count is settled by adding an offset to the number of breaths that is measured in advance during a normal condition.

A heartbeat signal or a pulse signal can be extracted from a biological back signal detected by the pulse wave sensor 73c as a piezoelectric film sensor. The pulse wave sensor 73c may be used to decrease the number of sensors. No steering sensor is available when the awakened or unawakened state needs to be detected from an occupant other than the driver. In such case, it may be preferable to use the pulse wave sensor 73c as a piezoelectric film sensor. All of the above-mentioned sensors need not to be provided. At least one of the sensors is needed. The sensors 73 may be eliminated when the unawakened state can be detected from an eye image to be described later. Nevertheless, many sensors are preferable for the purpose of accurately and reliably detecting an undetected state. It may be preferable to determine the occupant's awakened or unawakened state based on detection results from the sensors.

The camera 20 captures an eye of an occupant sitting on a specified seat and functions as an eye image capturing means. According to the embodiment, the camera 20 is attached to a vehicle ceiling ahead of a passenger. The camera 20 is oriented so as to cover the entire face of the occupant sitting in a capturing range. For example, the vehicle compartment is provided with an infrared light source for radiating light to the occupant's eye. The camera 20 captures the reflected light so as to be capable of detecting an unawakened state at night or under the condition of a small quantity of light.

The image analysis part 72 receives a captured image supplied from the camera 20 and performs the following two processes in this embodiment. The first process acts on an eye image captured by the camera 20 and detects a chronological change in the pupil size of a vehicle occupant sitting on the corresponding seat. The second process detects a blink based on the captured eye image. Specifically, the image analysis part 72 extracts a pupil area in an eyeball from the image captured by the camera 20. The first process then determines whether or not the size of the detected pupil causes a variation greater than or equal to a predetermined level. The process outputs a result to the control section 71. The control section 71 detects an unawakened state when the detected pupil size continues to be under a specified level for a specified time or longer (mitotic state). On the other hand, the second process detects a state in which no pupil is detected, namely, eyes are closed. The process outputs the result to the control section 71. The control section 71 counts the detected number of blinks. The control section 71 detects an unawakened state when the number of blinks exceeds a specified range within a predetermined time or eyes are closed continuously for a specified time or longer. The states detected by the first and second processes are stored as awakening information in a specified storage area of the control section 71.

An unawakened state may be detected otherwise than the above-mentioned methods using the eye image. For example, an unawakened state may be detected when a specified eyeball movement is detected in the predicted drowsy state.

The following concisely describes the onboard electronic devices 100 through 400.

The air conditioner 100 includes an air conditioner ECU 101 connected to an unshown sensor part, a drive part 130, and the operation part 140. The sensor part includes known air-conditioning control sensors such as an in-vehicle temperature sensor, an ambient temperature sensor, an evaporator sensor, and a solar sensor. The drive part 130 includes a motor and its drive circuit. The motor opens and closes various dampers such as an air mix damper, an air inlet mode selector damper, and a mode selector damper. The operation part 140 functions as a main operation part of the air conditioner 100. The operation part 140 is provided for the operation panel at the front center of the center console C. The operation part 140 is operable from users sitting on the driver's seat 2D and the passenger seat 2P. Specifically, the operation part 140 includes known air-conditioning operation parts such as AUTO switch, OFF switch, mode selector switch (MODE switch), air inlet mode selector switch, air flow rate switch/temperature switch, defroster switch, A/C switch, and control mode selector switch (DUAL switch).

The power window system 200 includes a power window ECU 201 connected with a drive part 230 and an operation part 240. The drive part 230 includes a motor and its drive circuit for opening and closing a window glass for the corresponding seat. The operation part 240 is provided for each seat 2 and opens and closes a window glass for the corresponding seat. Specifically, the operation part 240 is provided at a position where the user sitting on the seat 2 can operate the operation part 240 with his or her back against a backrest 2b of the seat. The operation part 240 is provided for a door corresponding to the seat 2.

The audio system 300 includes an audio ECU 301, a drive part 330, and an operation part 340. The audio ECU 301 includes known components such as a CPU, ROM, and RAM. The audio ECU 301 connects with a music data input device and a music database. The music data input device acquires music source data from a storage medium. The music database provides an external storage device for storing music source data. The operation part 340 according to the embodiment is provided for the center console C of the vehicle. The operation part 340 is operable from users sitting on the driver's seat 2D and the passenger seat 2P. The operation part 340 includes known audio operation parts such as a volume control part, a media selection part, and a song selection part. When these operation parts are used to specify a song to be output, the audio ECU 301 reads music source data for the specified song from the medium or the music database and outputs the music source data to the drive part 330. The drive part 330 decodes the music source data into digital music waveform data. The digital music waveform data is converted into analog data. The analog data passes through a preamplifier and a power amplifier, and is output from a speaker at specified volume.

The seat adjusting system 400 includes a seat adjustment ECU 401 connected with a drive part 430 and an operation part 440. The drive part 430 includes a motor and a drive circuit for electrically moving the seat 2 and tilting the backrest. The seat 2 can be moved in the front-back direction and vertically at the front and rear ends. The operation part 440 allows the user to adjust seat positions. The operation part 440 is provided at a position where the user sitting on the seat can operate the operation part 440 with his or her back against the backrest 2b. According to the embodiment, the operation part 440 is provided at each side of the seat 2.

Figure 13:
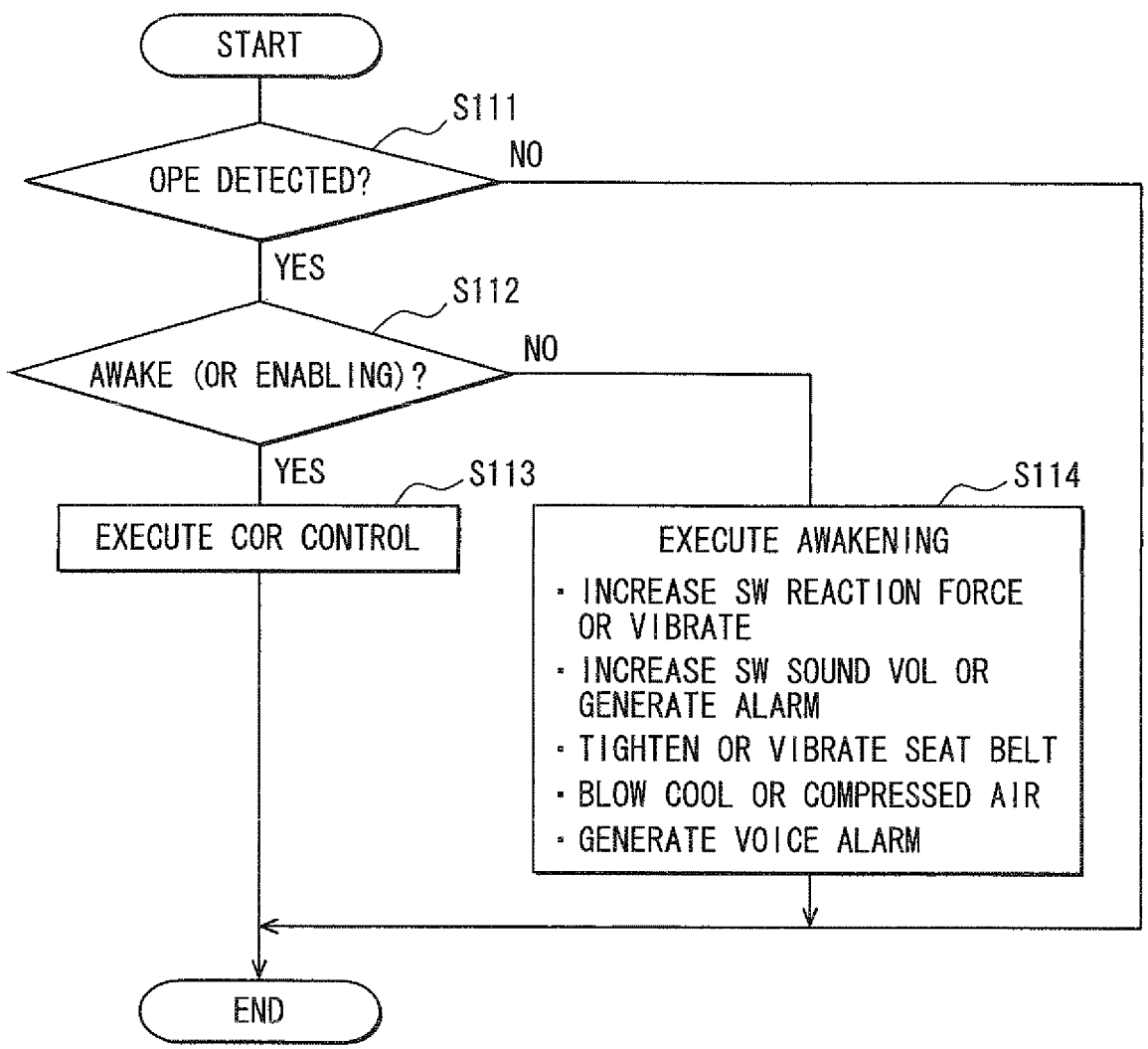
FIG. 13 is a flow chart showing an input operation process different from that in FIG. 8.

When an input operation is performed in the unawakened state (operation disabling mode), the above-mentioned embodiment disables the input operation and notifies that the input operation is disabled. When the driver as an operator performed the disabled operation, the embodiment can notify the disablement and can also provide awakening output so as to prompt the driver into the normal awakened state (awakening means). The awakening output may be provided as disablement notification output or along with the disablement notification. FIG. 13 is a flow chart showing an input operation process including awakening output (S114) instead of the notification of the disabled operation (S104) in FIG. 8. Performing this process can provide awakening output in the unawakened state.

Awakening output or awakening action examples include increasing an operation reaction force against the touch operation panel 12a1, vibrating the touch operation panel 12a1, increasing an operation sound volume for the touch operation panel 12a1, changing an operation sound for the touch operation panel 12a1, generating an awakening sound, generating an alarm sound, increasing a force for tightening a seat belt, vibrating the seat belt, and supplying air from the air conditioner 100.

Figure 12:
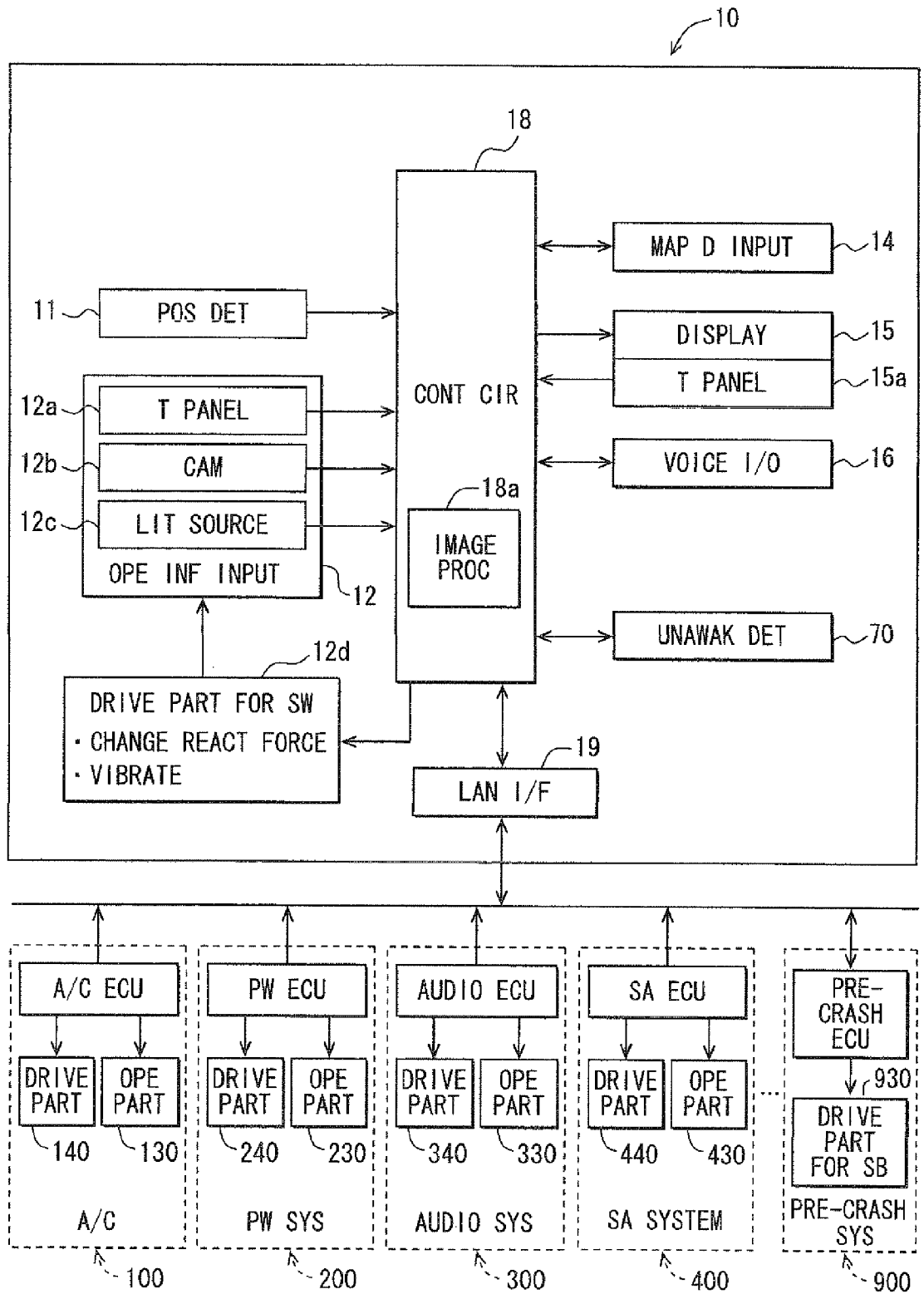
FIG. 12 is a block diagram showing another configuration of the vehicular navigation system in FIG. 1.

For example, a configuration in FIG. 12 may be used to provide the awakening output for increasing an operation reaction force. An additional operation part is provided to apply a suppress strength in place of the touch panel 12a. An operation part drive part (switch drive part) 12d is provided as a reaction force generating part. The operation part drive part (reaction force generating part) 12d is driven to increase an operation reaction force against the pressing operation on the operation part 12a. When a haptic device is used for the operation part 12a, for example, the operation part drive part 12d increases a reaction force value for a motor that generates the operation reaction force. When the operation part 12a uses a push switch or a rocker switch to which a spring applies force, there may be provided a mechanism that selects another spring to apply a different force. Increasing the operation reaction force can stimulate awakening by stimulating a sense of discomfort during input operation.

When an awakening output is generated to vibrate the operation part 12a1, the operation part drive part 12d is configured as a vibration generating part as shown in FIG. 12 to vibrate the operation part 12a1. When the operation part vibrates, the operator can clearly sense a difference from the normal operation at the instant of the operation, making it possible to effectively stimulate the awakening.

The awakening output may be provided by increasing the volume of an operation sound or changing the operation sound that is generated in synchronization with the operation on the operation part 12a1. In this case, the configuration in FIG. 1 or FIG. 12 is used to change an operation sound output setting to an awakening output setting and generate the operation sound in accordance with the setting. The operation sound data is available for normal and awakening output uses. Both types of data are stored in a specified storage of the control circuit 18 and are read as needed. When the awakening output is audibly provided to stimulate awakening on the operation part 12, sound data is stored in a specified storage of the control circuit 18 and is read as needed. The operator can clearly sense a sound difference from the normal operation, making it possible to effectively stimulate the awakening.

The configuration in FIG. 12 may provide the awakening output so as to increase a force for tightening a seat belt or vibrate the seat belt attached to the operator who operated the operation part 12a1. In this case, a pre-crash safety system 900 is mounted on a vehicle. The control circuit 18 supplies an ECU 901 with a drive command for increasing the tightening force of the corresponding seat belt so that a seat belt drive part 930 is driven to increase the tightening force. Alternatively, the control circuit 18 supplies the ECU 901 with a drive command for repeatedly increasing and decreasing the tightening force of the corresponding seat belt so that the seat belt drive part 930 vibrates the seat belt. It is possible to reliably stimulate awakening.

According to the configuration in FIG. 1 or 12, the ECU 101 of the air conditioner 100 controls an air conditioning output parameter so as to lower the temperature and increase an air capacity. When no wind is generated, sending air at a given air capacity level or higher provides a sufficient awakening effect.

All the above-mentioned embodiments describe the operation part that is capable of enabling or disabling input operations so as to prevent incorrect operations. The operation part may be provided elsewhere when it is operable from a specified seat. From the viewpoint of prevention against incorrect operations, the operation part may be configured as a near-occupant operation part fixed to a position where the occupant sitting on the seat can operate the operation part with his or her back against the backrest. In the above-mentioned embodiment, for example, the operation part 440 of the seat adjusting system 400 corresponds to the driver's seat 2D and functions as a main operation part for the remote operation part 12a. The operation part 440 is configured to be incapable of enabling or disabling input operations. The operation part 440 may be configured to be capable of enabling or disabling input operations similarly to the remote operation part 12a in the above-mentioned embodiment.

All the above-mentioned embodiments describe the operation part that is capable of enabling or disabling input operations so as to prevent incorrect operations. The operation part is provided as the remote operation part capable of remote operations in place of the main operation part. The operation part may not be necessarily provided as the remote operation part or may be provided with no main operation part. The operation part may be replaced by the main operation part or may include both the main operation part and the remote operation part. The remote operation part need not be operated while displaying hand operations on the screen of the display apparatus as described in the above-mentioned embodiment.

All the above-mentioned embodiments describe the operation part that is capable of enabling or disabling input operations so as to prevent incorrect operations. The operation part is provided as the touch panel 12a operable from a specified seat. The operation part need not be provided as a tactile operation part having the touch operation panel 12a1 such as a touch panel so long as the operation part is operable from the seat. For example, the operation part may include a push switch, a rocker switch, or any switch that is operated by pressing.

All the above-mentioned embodiments describe the operation part that is capable of enabling or disabling input operations so as to prevent incorrect operations. The operation part uses the resistive touch panel 12a and may use the other technologies for the touch panel.

Instead of the touch panel, the operation panel 12a may detect a touch operation position by processing an image captured by a capturing means such as a camera.

All the above-mentioned embodiments describe the operation part that is capable of enabling or disabling input operations so as to prevent incorrect operations. The operation part may be operable from not only the driver's seat but also the other seats.

Second Embodiment

Figure 14:
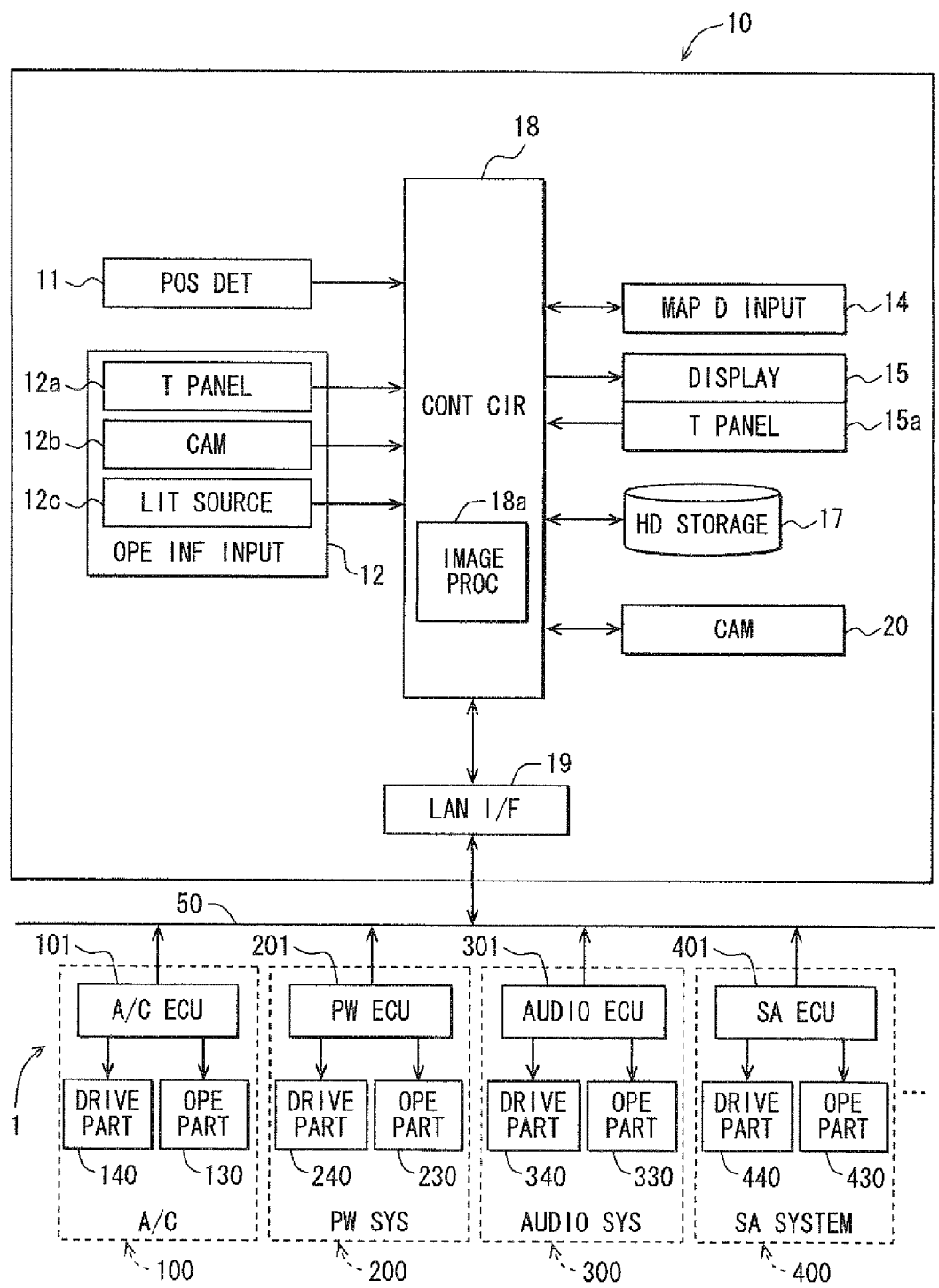
FIG. 14 is a block diagram showing a configuration of a vehicular navigation system using a prompter-based vehicular input apparatus as an example of a touch input apparatus according to a second embodiment.

FIG. 14 is a block diagram showing a configuration of a vehicular navigation system using the input apparatus according to a second embodiment. According to the embodiment, an input apparatus 1 complies with a prompter technology. The input apparatus 1 is provided with a display apparatus 15 and an operation panel 12 at different positions. The display apparatus 15 is capable of displaying a switch image (operation icon) for touch operation on a display screen. The operation panel 12 is used for remotely controlling the touch operation on the display screen. The touch-type input apparatus according to the embodiment is targeted for controlling not only navigation functions but also the other onboard electronic devices and functions such as an air conditioner 100, a power window system 200, an audio system 300, and a seat adjusting system 400. The other onboard devices and functions are controlled by control parts such as ECUs 101, 201, 301, and 401 that are connected to a control circuit 18 through an interior LAN 50.

A navigation system 10 includes the following. A position detector 11 uses a global positioning system (GPS) to detect the current position of the vehicle. An operation information input part 12 is used for entering various instructions from an operator such as a driver. A map data input device 14 is used for entering map data from an external recording medium that stores map data and various information. A display apparatus 15 provides various displays such as a map display screen and a television (TV) screen. A hard disk storage 17 stores various data such as vehicle information. A vehicle interface (I/F) 19 interchanges vehicle information. The control circuit 18 connects with these components. The control circuit 18 also connects with a camera 20 as a capturing means for capturing an operator's face image.

Figure 20:
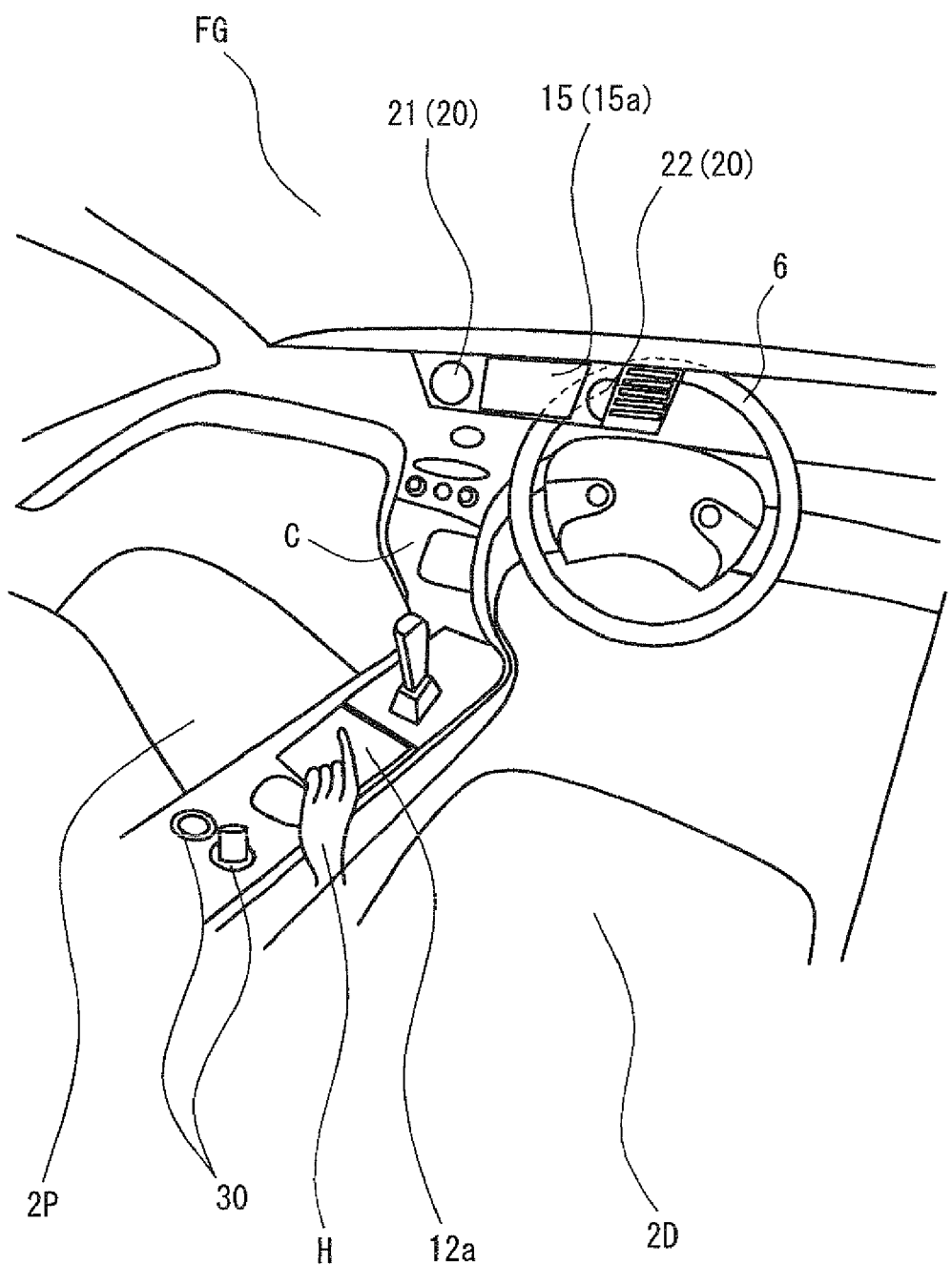
FIG. 20 is a perspective view of a vehicle compartment provided with a prompter-based vehicular input apparatus.

As shown in FIG. 20, the operation information input part 12 according to the embodiment is provided for a center console C of the vehicle or a position that is below a windshield FG of the vehicle and is operable from the adjacent left and right seats. Further, the operation information input part 12 is provided below the display apparatus 15 between both bottoms of the adjacent left and right seats toward the vehicle front so that the user can operate the operation information input part 12 with his or her back against the backrest. According to the embodiment, the adjacent left and right seats are equivalent to a driver's seat 2D and a passenger seat 2P in FIG. 20.

The operation panel 12a is translucent so as to transmit at least the light radiated from the light source 12c. The operation panel 12a according to the embodiment is configured as a known resistive touch panel provided with vertical and horizontal transparent electrodes. An output from the operation panel 12a is input to the control circuit 18. In the embodiment, the operation panel 12a is predetermined as a lock object operation part for an object to be locked.

Now returning back to FIG. 14, the display apparatus 15 provides color capabilities and, as shown in FIG. 20, is positioned toward the vehicle front ahead of occupants sitting on the driver's seat 2D and the passenger seat 2P so that both occupants can view the screen of the display apparatus 15. The display apparatus 15 may be placed not only within the center console C as shown in FIG. 20 but also above the lower edge of the windshield FG, for example. Examples of the display apparatus 15 may include a head up display (HUD) for displaying the above-mentioned image or data on the windshield FG of the vehicle and a meter display apparatus positioned toward the bottom of a steering wheel 6.

The control circuit 18 is mainly configured as a known microcomputer including a known but unshown CPU, ROM, RAM, an input/output device, and a bus line connecting these components. The control circuit 18 provides various controls related to known navigation functions based on a program stored in a storage part such as the ROM. The control circuit 18 acquires data from the outside such as the other ECUs 101, 201, 301, and 401 through the LAN interface 19 and the interior LAN 50.

Figure 18:
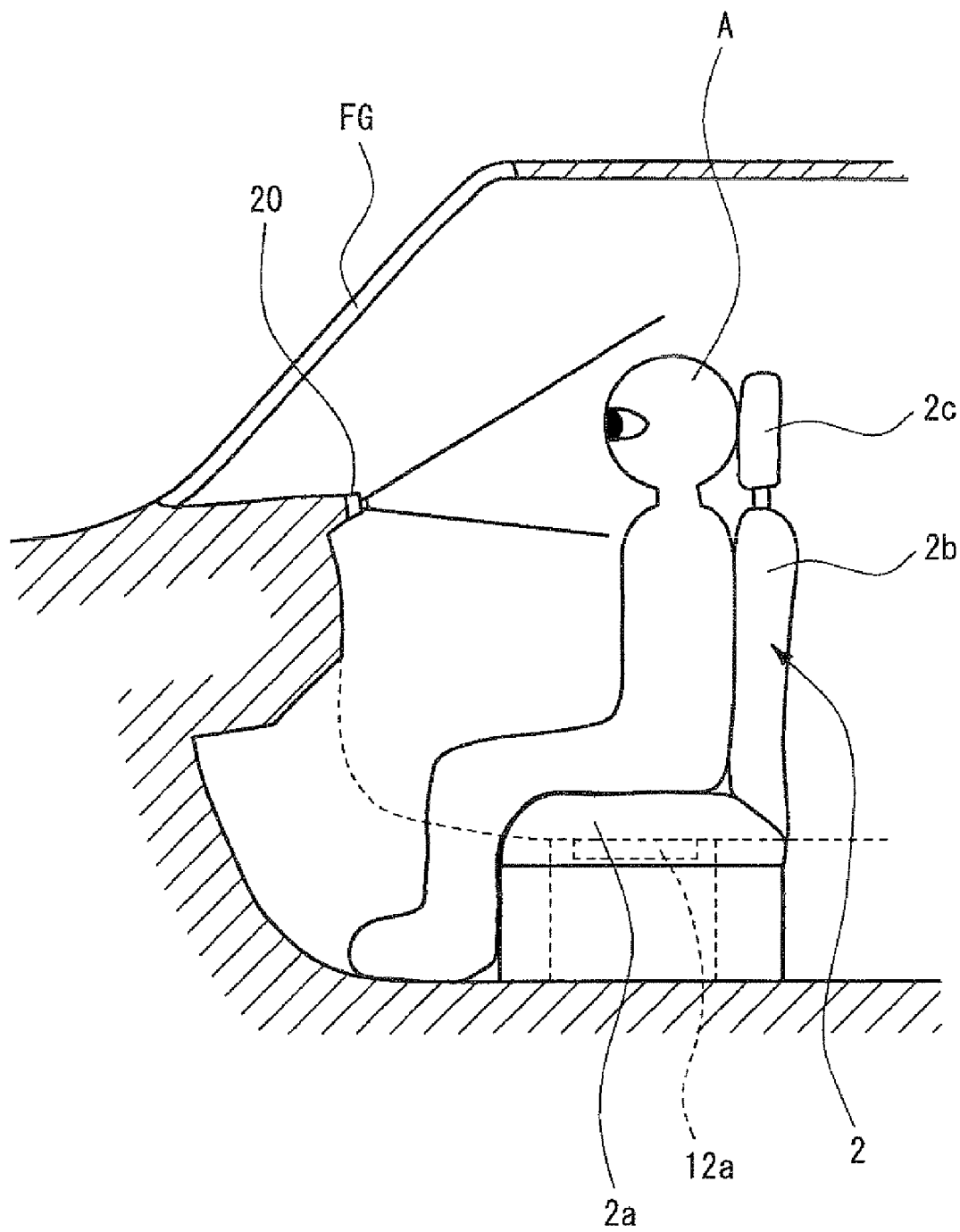
FIG. 18 illustrates how an operator is captured.

The control circuit 18 is connected to the camera 20. The camera 20 captures the face of an occupant sitting on a specified seat and functions as a face image capturing means. As shown in FIG. 18, the camera 20 according to the embodiment is fixed below the eye position of an operator A operating the operation part 12a and above the operation part 12a. In the horizontal direction of the vehicle, the camera 20 is fixed near the operation part 12a or to the left because the operator A is a driver in this example. In the longitudinal direction of the vehicle, the camera 20 is fixed to the vehicle front ahead of the operator A. The position of the camera 20 makes it possible to easily detect a visual line of the operator A who views the operation part 12a positioned below. The camera 20 is attached adjacently to the display apparatus 15. The camera 20 is oriented so as to cover the entire face of the occupant sitting in a capturing range. For example, the vehicle compartment is provided with an infrared light source for radiating light to the operator's eye. This is because the infrared light is invisible to the operator to be captured and is free from a noise in the natural light. The camera 20 captures the light reflected on the surface of the eye so as to be capable of capturing at night or under the condition of a small quantity of light.

Figure 19A:
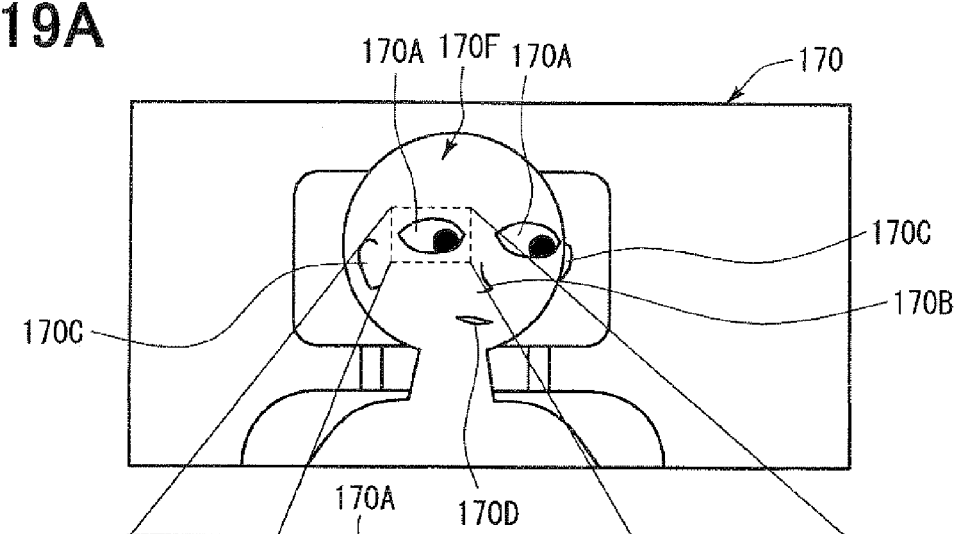
FIGS. 19A to 19C illustrate an example of detecting a visual line.
Figure 19B:
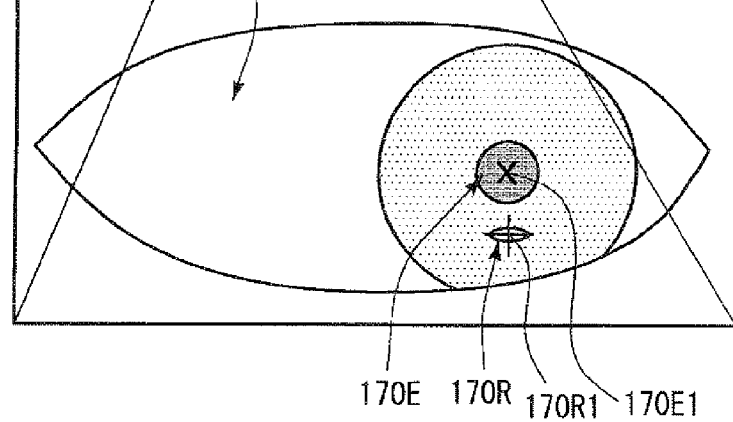
Figure 19C:
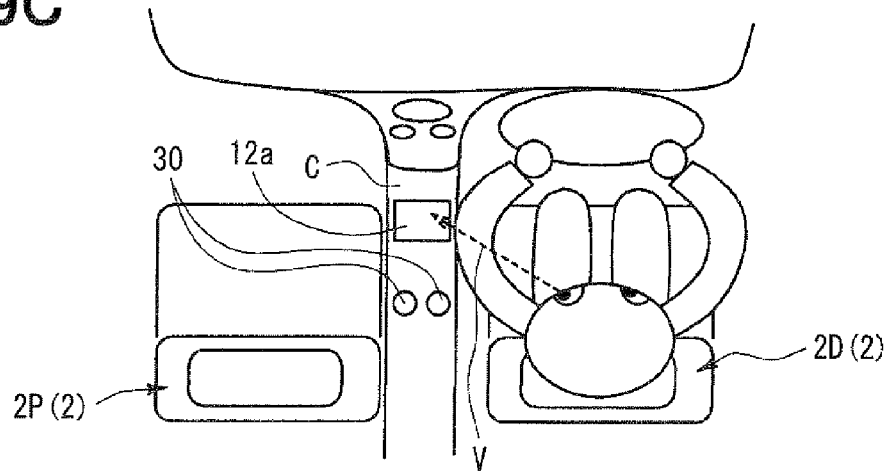

A captured image 170 captured by the camera is input to an image analysis part 18b. The image analysis part 18b analyzes a visual line (visual line vector) V. A known corneal reflex method or the other methods may be used to detect a visual line. As shown in FIGS. 19A to 19C, the image analysis part 18b first extracts a face image 170F. The face image 170F contains reference part images such as an eye 170A, a nose 170B, an ear 170C, and a mouth 170D. Based on the positional relation between the reference part images, the image analysis part 18b detects the face direction toward the vehicle front, namely, the face orientation in a three-dimensional coordinate system defined in the vehicle. The coordinate system is hereafter referred to as a vehicle compartment coordinate system and contains an X direction corresponding to the front-back direction of the vehicle, a Y direction corresponding to the left-right direction thereof, and a Z direction corresponding to the vertical direction thereof. The image analysis part 18b then extracts an eye image 170E from the face image 170F. From the eye image 170A, the image analysis part 18b detects a reflected image 170R of the point light source (center 170R1 of a reflected point light source image) on the cornea surface of the eye. The image analysis part 18b also detects a pupil 170E (pupil center 170E1). Based on these images and the face orientation, the image analysis part 18b calculates an iris position (iris center position) and a visual line vector V in the vehicle compartment coordinate system.

The control circuit 18 previously stores a layout area for a given operation part as coordinate information in the vehicle compartment coordinate system. The control circuit 18 determines whether or not the operation part 12a included in the lock object operation part exists along the visual line in the visual line direction from the iris position. The embodiment temporarily releases an input operation disable mode (operation lock) assigned to the operation part 12a when the operation part 12a included in the lock object operation part exists along the visual line. An input operation enable mode turns on to allow an input operation.

The vehicular input apparatus 1 according to the embodiment is configured as mentioned above. The vehicular input apparatus 1 allows the control circuit 18 to detect the visual line of an operator who operates the operation part 12a included in the lock object operation part. In addition, the control circuit 18 determines whether or not the detected visual line activates an operation releasing visual line state to release the state of inhibiting an input operation on the operation part. Normally, the operation part 12a is assigned the input operation disable mode as an input operation mode so as to inhibit input operation on the operation part 12a. Detecting the operation releasing visual line state activates the input operation enable mode to permit an input operation on the operation part 12a. According to the configuration, the visual line or the user's eye movement unlocks the operation part 12a on which operations are locked or inhibited. The configuration can greatly improve a conventional inconvenient unlock operation. It is also possible to reliably prevent an incorrect operation on the operation part 12a. A conventional technology enables an unlock operation even when the hand is just placed near the operation part. In FIG. 20, for example, let us suppose that the operator's hand H is originally placed on the steering wheel 6. When the hand H moves to a can holder 30, just letting the hand H pass over the operation part 12a may unlock the operation part 12a. The same applies to a case of moving the hand H from the can holder 30 to the steering wheel 6. The configuration can prevent such incorrect unlock operation.

In the operation releasing visual line state according to the embodiment, the visual line detected by a visual line detection means is directed to at least a predetermined operation releasing visual line area. Specifically, the operation releasing visual line state is defined as a state in which the visual line detected by the visual line detection means is continuously directed to the operation releasing visual line area for a predetermined viewing time (1.5 seconds or shorter). The operation releasing visual line area according to the embodiment is defined as a layout area for the operation part for which the input operation mode is assigned.

According to the embodiment, the camera 20 is provided for both sides of the display apparatus 15. Each of both cameras captures a driver or a passenger sitting on the passenger seat, In the embodiment, a camera 21 (20) captures the driver. A camera 22 (20) captures the passenger sitting on the passenger seat. The operation part to be assigned the input operation mode is assumed to be fixed to a position that allows the passenger on the specified seat to be capable of operations. Further, such operation part is assumed to be a near-occupant operation part fixed to a position where a sitting vehicle occupant is capable of operations. The embodiment assigns the input operation mode to the operation panel 12a configured as the remote operation part that is fixed to a position capable of operations from both the driver's seat and the passenger seat.

According to the embodiment, an operation part 15a is separately provided for the display apparatus 15 and functions as a main operation part for the operation panel 12a to be assigned the input operation mode. The operation part 12a is a remote operation part capable of remote input operation on the main operation part 15a. Further, the operation panel 12a to be assigned the input operation mode is capable of input operations on the other onboard devices such as the air conditioner 100, the power window system 200, the audio system 300, and the seat adjusting system 400. The operation panel 12a may be considered to be a remote operation part that is used for the operation parts 140, 240, 340, and 440 as main operation parts and enables remote input operations on the main operation parts. The main operation parts 15a, 140, 240, 340, and 440 are fixed to positions farther from an operator (or the driver in the embodiment) than the operation panel 12a configured as the remote operation part. The main operation parts are less easily operable than the remote operation part 12a to be assigned the input operation mode.

Figure 15:
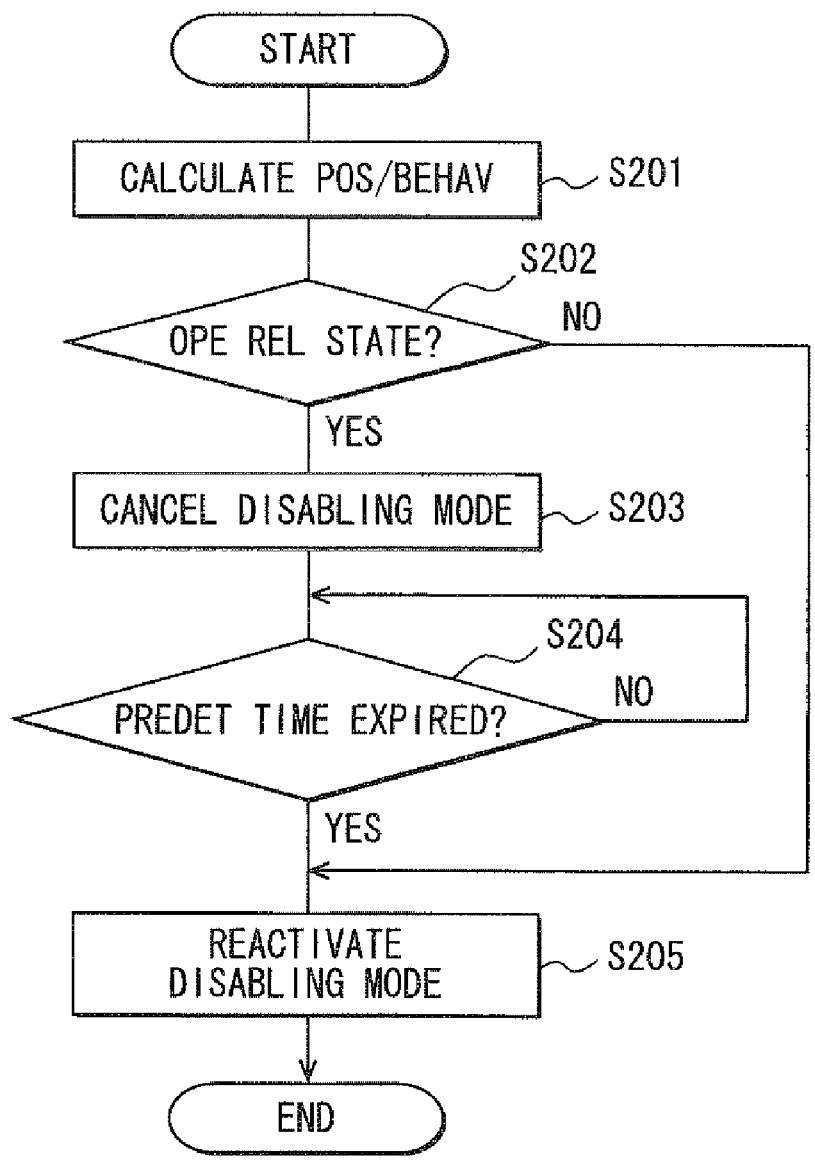
FIG. 15 is a flow chart showing an input operation restriction process.

With reference to FIG. 15, the following describes an input operation restriction process for the operation panel 12a configured as the remote operation part. The process is performed when the CPU executes a program stored in a specified storage of the control circuit 18. To start the input operation restriction process, the operation panel 12a to be assigned the input operation mode is assigned the input operation disable mode as the input operation mode.

At S201, the control circuit 18 acts on a captured image captured by the camera 20 and calculates a pupil position and a visual line vector in the specified vehicle compartment coordinate system. Thus, in S201, the position and the behavior of a visual line of the operator is calculated.

At S202, the control circuit 18 determines whether or not the visual line state detected at S201 is assumed to be the predetermined operation releasing visual line state. According to the embodiment, the operation releasing visual line state is defined so that the detected visual line is directed to the operation panel 12a as an operation releasing visual line area for the predetermined viewing time to (one second in the embodiment). The process proceeds to S203 when the operation releasing visual line state is detected. Otherwise, the process proceeds to S205.

At S203, the control circuit 18 inactivates the input operation disable mode assigned to the operation panel 12a to be assigned the input operation mode and activates the input operation enable mode. Thus, in S203, the operation disable mode of the operation panel 12a is cancelled. The input operation enable mode is active during a predetermined input operation enable time (one minute in the embodiment). When the time t1 (i.e., a predetermined time) expires at S204, the process proceeds to S205 to resume the input operation disable mode. Thus, in S205, the operation disabling mode is reactivated. The current state of the input operation mode is stored in a specified storage area (input operation mode storage part) of the control circuit 18. After S203, the storage area stores the input operation enable mode. After S205, the storage area stores the input operation disable mode.

The process terminates upon completion of S205. After termination, the process is repeated at a specified cycle. The control circuit 18 changes the input operation mode in accordance with the detected operation releasing visual line state.

The control circuit 18 performs the input operation restriction process to function as the visual line detection means, a releasing visual line specification means, and an input operation mode setup means.

Figure 16:
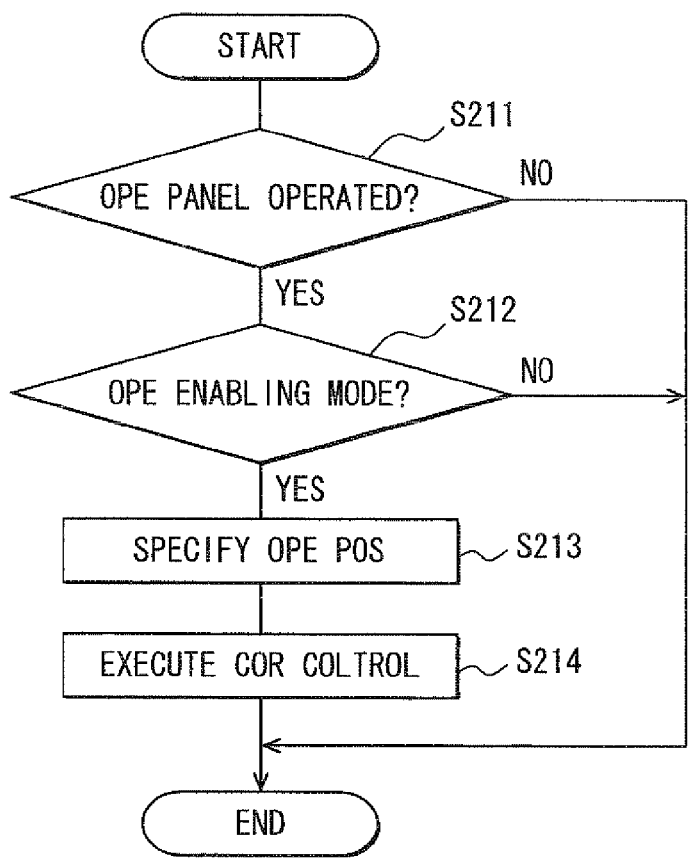
FIG. 16 is a flow chart showing an input operation process.

With reference to FIG. 16, the following describes an input operation process for the operation panel 12a to be assigned the input operation mode.

At S211, the control circuit 18 determines whether or not the operation panel 12a is operated. The operation panel 12a is configured as a touch panel. A touch operation allows a corresponding operation signal to be supplied to the control circuit 18. The control circuit 18 determines the presence or absence of the input operation signal. The process proceeds to S212 when a touch operation is detected on the operation panel 12a. Otherwise, the process terminates.

At S212, the control circuit 18 determines whether or not the current input operation mode is the input operation enable mode. The current input operation mode is stored in the specified storage area (input operation mode storage part) of the control circuit 18. The control circuit 18 reads the stored current input operation mode for the determination. The process proceeds to S213 when the input operation enable mode is active.

At S213, the control circuit 18 specifies a touch operation position on the touch operation panel 12a1. The operation panel 12a is configured as a touch panel. A touch operation inputs an operation signal to the control circuit 18. The operation signal reflects touch operation position information, namely, coordinate information in an operation coordinate system predetermined for the operation surface 12a1. Based on the operation signal, the control circuit 18 specifies the coordinate position corresponding to the touch operation.

At S214, the control circuit 18 provides control corresponding to the touch operation position on the operation panel 12a. Positions on the touch operation panel 12a1 of the operation panel 12a correspond to those on the surface of a display screen 15. The control circuit 18 specifies a position on the display screen 15 corresponding to the position specified at S213 on the touch operation panel 12a1. The control circuit 18 performs a control content corresponding to the specified screen position. Specifically, the control circuit 18 outputs a control signal for performing the control content. For example, let us suppose that the position on the touch operation panel 12a1 specified at S213 corresponds to a position for a switch image 160I displayed on the display screen 15. The control circuit 18 outputs a control signal for performing the control content assigned to the switch image. Thus, in S214, control corresponding to the touch operation position is executed.

When the input operation disable mode is detected at S212, the control circuit 18 terminates the process without performing the control contents at S213 and S214 corresponding to the operation. That is, the input operation is assumed to be incorrect and is nullified.

The process terminates upon completion of S214. After termination, the process is repeated at a specified cycle.

The control circuit 18 functions as an input operation acceptance means when detecting an operation on the operation part to be assigned the input operation mode. When the input operation enable mode is activated as the input operation mode, the control circuit 18 performs the control content corresponding to the operation. When the input operation disable mode is activated, the control circuit 18 nullifies the operation and does not perform the control content corresponding to the operation.

Figure 17:
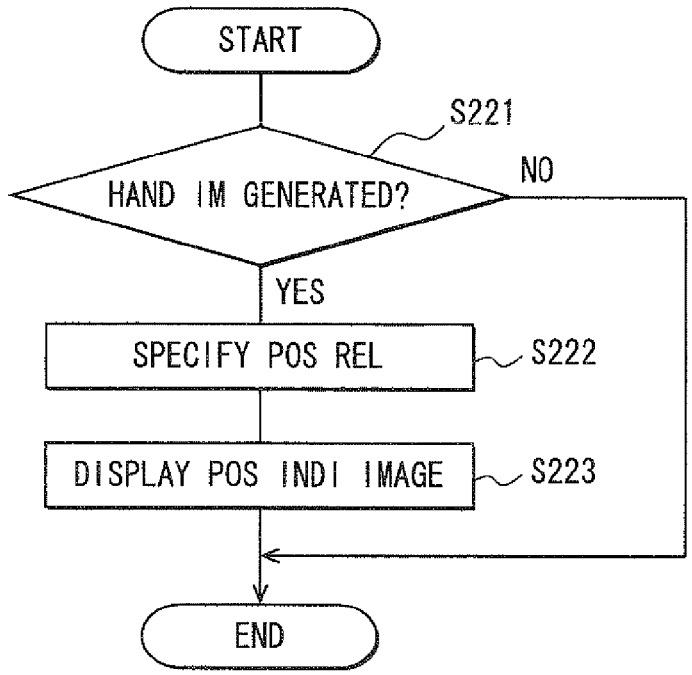
FIG. 17 is a flow chart showing a process of displaying a position indication image.

With reference to FIG. 17, the following describes a process of displaying a position indication image on the display apparatus 15. The process is performed when the CPU executes a program stored in a specified storage of the control circuit 18.

At S221, the control circuit 18 acts on a captured image captured by a camera 12b and determines whether or not an operator's hand image is generated. The camera 12b always captures an approaching object H (e.g., a hand of the operator such as the driver) from a second surface 12a2 of the operation panel 12a through the operation panel 12a. The approaching object H is assumed to approach the touch operation panel (first surface) 12a1. The captured image is always input to an image processing part 18a of the control circuit 18. When the approaching object H enters a position opposite to the touch operation panel 12a1, the image processing part 18a is supplied with a captured image 150 including the approaching object H. The image processing part 18a uses a known image analysis technology to analyze the input captured image and extracts an approaching object image 150H based on a color difference or the like. The image processing part 18a recognizes the shape of the extracted approaching object image 150H and determines whether or not the image 150H represents a human hand image. A determination result is output to the control circuit 18. The process proceeds to S222 when it is determined that the hand image is recognized. Otherwise, the process terminates.

At S222, the control circuit 18 specifies a position on the touch operation panel 12a1. More specifically, the image processing part 18a extracts the hand image at S221. From the entire shape of the hand image, the control circuit 18 locates a finger by identifying an approximately linear, rod-like image pattern having an axis line as long as a specified length or longer. The control circuit 18 further locates a fingertip position from the located finger. According to the embodiment, the touch operation panel 12a1 is positioned to an operation panel image area. The control circuit 18 specifies the operation panel image area on the captured image captured by the camera 12b. The control circuit 18 also settles an operation coordinate system for the touch operation panel 12a in the operation panel image area. The control circuit 18 then locates the fingertip position in the settled operation coordinate system. According to the embodiment, the captured image 150 (binarized image) in FIGS. 9B and 10B is equivalent to the operation panel image area that capture the whole of the touch operation panel 12a1. Thus, in S222, a positional relationship between the hand and the image on the display apparatus 15 is determined.

At S223, the control circuit 18 displays a position indication image 160H at the fingertip position on the display screen of the display apparatus 15 as shown in FIGS. 9C and 10C (position indication image display means). The fingertip position is specified on the operation panel image area. At S215, the control circuit 18 specifies a position on the display screen of the display apparatus 15 corresponding to the fingertip position specified in the operation coordinate system. The display screen is provided with a display coordinate system that corresponds to the operation coordinate system. The control circuit 18 displays the position indication image 160H on the display screen so as to specify a position coordinate in the display coordinate system corresponding to the fingertip coordinate position in the operation coordinate system and locate the position coordinate. The position indication image 160H according to the embodiment is processed so as to clearly display an outline (external shape) of the hand image 150H and make the outline inside semi-transmissive. A main image 160B is overlaid with the position indication image 160H at the coordinate position specified on the screen of the display apparatus 15. Thus, in S223, the position indication image is superimposed on the corresponding position on the display apparatus 15.

The process terminates upon completion of S223. After termination, the process is repeated at a specified cycle. Moving the hand or finger opposite to the operation panel 12a accordingly moves the display position of the position indication image 160H (processed image) displayed on the display screen of the display apparatus 15.

The control circuit 18 functions as the position indication image display means by performing the process of displaying the position indication image.

The following describes in detail the display apparatus 15 according to the embodiment.

The display apparatus 15 according to the embodiment includes a display surface for operating devices provided for the vehicle. The display surface according to the embodiment functions as a tactile operation part used for tactile operations. Specifically, the display surface is provided with a touch panel 15a so as to function as the tactile operation part. The touch panel 12a of the operation information input part 12 is provided as a remote operation part so as to remotely operate the touch panel 15a from a position nearer to the driver or the passenger on the passenger seat. A touch operation is performed on the touch operation panel (also referred to as a remote operation surface) 12a1. The control circuit 18 accepts input to the screen position on the display apparatus 15 corresponding to the position of the touch operation. Specifically, a two-dimensional coordinate system is defined on the display screen of the display apparatus 15, namely, on the touch operation panel of the touch panel 15a. Another two-dimensional coordinate system is defined on the touch operation panel 12a1 of the operation panel 12a. A unique correspondence relation is predetermined between both two-dimensional coordinate systems. The position in one coordinate system is uniquely specifiable in the other coordinate system. When a touch operation is performed on the touch operation panel 12a1, the input operation is accepted based on the correspondence relation. The position coordinate for the touch operation corresponds to the position coordinate on the display screen of the display apparatus 15.

When a touch operation is performed on the touch operation panel 12a1 having the remote operation surface, the control circuit 18 locates the position coordinate on the touch operation panel 12a1 where the touch operation is performed. The control circuit 18 locates the position coordinate on the display screen of the display apparatus 15 corresponding to the located position coordinate on the touch operation panel 12a1. The control circuit 18 then outputs a control signal for performing a control content corresponding to the position coordinate. For example, let us suppose that the display screen of the display apparatus 15 displays the switch image 160I such as an operation icon. A touch operation is supposed to be performed on the touch operation panel 12a1 at a position corresponding to the switch image 160I. The control circuit 18 recognizes the touch operation on the switch image 160I and functions as an input acceptance means to accept the input. The control circuit 18 also performs a control content corresponding to the switch image 160I. Let us suppose that the display screen of the display apparatus 15 displays a scrollable map screen (map manipulation image). When a touch operation is performed on the touch operation panel 12a1 at the position on the map, the control circuit 18 accepts the input at the touched position. The scroll control is accordingly performed to display the map around the touched position as a new screen center.

The storage part such as ROM of the control circuit 18 stores switch image data for displaying the switch image 160I. The switch image data is used to display the switch image 160I in an overlaid or composed fashion. The storage part such as ROM of the control circuit 18 also stores a control content corresponding to the switch image 160I. The control content is performed in accordance with an input operation at the corresponding area on the touch operation panel 12a1. Let us suppose that the control circuit 18 displays an image 160 including the switch image 160I overlaid on the main image 160B displayed on the display screen. Both touch operation panels of the touch panels 12a and 15a are assigned an input operation acceptance range (input operation position) at an area corresponding to the display position of the switch image 160I so as to function as an input operation positioning means. Let us suppose that the display screen displays a scrollable map screen (map manipulation image) as the main image 160B. The whole of the displayed map area is assigned an input operation acceptance range (input operation position) so as to function as an input operation positioning means.

The following describes in detail the display of the position indication image 160H according to the embodiment.

The control circuit 18 according to the embodiment includes the image processing part 18a. Based on a program stored in the storage part such as the ROM, the image processing part 18a displays the main image 160B such as the map manipulation image so as to be combined or overlaid with a sub-image. The sub-image includes the switch image (operation icon) 160I and the processed image 160H based on the approaching object image 150H acquired from the operation information input part 12. According to the embodiment, the approaching object image 150H represents a hand. The processed image 160 is generated based on the captured image 150H of the hand. The processed image 160 is used as a position indication image so as to be overlaid on the position located by the hand (fingertip) on the display screen.

According to the embodiment, the processed image 160H based on the approaching object image 150H is processed and generated so as to reflect the external shape of the approaching object image 150H. The image 160H is overlaid on the main image 160B. Instead, the image 160H may be combined with the main image 160B. For example, let us suppose that the operator such as the driver moves his or her finger opposite to the touch operation panel 12a1 of the operation panel 12a. The display screen of the display apparatus 15 displays the processed image 160H reflecting the hand or finger shape so that the displayed image moves accordingly. The operator can operate the operation panel 12a as if it were placed on the display screen of the display apparatus 15.

The position indication image 160H may not necessarily reflect the outline of the captured hand or finger shaper. The image just needs to indicate at least the position indicated by the captured finger. The image may be replaced by a symbolic image such as a pointer. The position indication image 160H may use an unprocessed version of the hand or finger image 150H captured by the camera 12b for overlaid or combined display. However, such unprocessed image may hide an overlapping part of the main image 160B. In consideration for this, it may be preferable to apply a process such as alpha blending to the captured image for improved operability.

The above-mentioned embodiment defines the operation releasing visual line state that allows the visual line to be continuously directed to the operation releasing visual line area for the predetermined viewing time t0. Further, the operation releasing visual line state may be defined otherwise. For example, the input operation disable mode may be inactivated (unlocked) when the visual line is moved in accordance with a specified pattern and this movement pattern is detected.

The operation releasing visual line state may be defined as decreasing the movement speed of the visual line to a predetermined speed level or lower when the visual line enters the operation releasing visual line area. This makes it possible to more easily inactivate or unlock the input operation disable mode. During driving, for example, the driver is highly likely to often view such an area as a windshield ahead of the driver, a rearview mirror, a side mirror, or the display apparatus screen. The operation releasing visual line area requires viewing in the operation releasing visual line state and may not be assigned to such frequently viewed area during driving but to a different area where no visual line passes during normal operations. The visual line is unlikely to be directed to the area. In such area, the input operation disable mode is unlikely to be inactivated unexpectedly. The area may be configured to more easily inactivate the input operation disable mode.

According to the above-mentioned embodiment, the input operation mode is assigned to only one operation part, that is, the operation panel 12a. The input operation mode may be assigned to multiple operation parts. For example, the input operation mode may be assigned to various push switches, rocker switches, and dial switches included in the air conditioner operation part 140, the power window operation part 240, the audio operation part 340, and the seat adjusting operation part 440 that are configured as the main operation parts according to the above-mentioned embodiment.

It may be preferable to predetermine an operation part group of operation parts out of the above-mentioned operation parts. The operation releasing visual line area may be individually assigned to the operation part group. The input operation mode may be provided for each operation part group. The operation part group associated with the operation releasing visual line area may be predetermined so as to include operation parts for operating the same device or device function. The operation part group associated with the operation releasing visual line area may also be defined so as to include operation parts in a predetermined layout area.

In these configurations, the process at S203 in FIG. 15 is modified as follows. The control circuit 18 determines which operation part group corresponds to the operation releasing visual line area indicated by the visual line specified at S201. The control circuit 18 collectively activates the input operation enable mode as the input operation mode only for the operation parts belonging to the specified operation part group. The control circuit 18 maintains the input operation disable mode as the input operation mode for the remaining operation parts.

According to the above-mentioned embodiment, the input operation mode is assigned to the tactile operation part having the touch operation panel that allows tactile input operations. Alternatively, the input operation mode may be assigned to the other push switches, dial switches, and so on. On the other hand, the apparatus is particularly effective for the tactile operation part having the touch operation panel because such tactile operation part allows easier operations and is often susceptive to incorrect operations.

According to the above-mentioned embodiment, the input operation mode is assigned to the remote operation part paired with the main operation part. The apparatus may allow the input operation mode to be assigned to a normal operation part having no main operation part. From the viewpoint of prevention against incorrect operations, it is recommended to assign the input operation mode to the operation part fixed near an occupant sitting on the seat. Particularly, it is recommended to assign the input operation mode to the near-occupant operation part fixed to a position where an occupant sitting on the vehicle seat can operate the operation part with his or her back against the backrest.

The above-mentioned embodiment allows the screen of the display apparatus to display an operation state of the operation part assigned the input operation mode. The apparatus may assign the input operation mode to an operation part independent of the display apparatus.

The above-mentioned embodiment assigns the input operation mode to the resistive touch panel 12a as an operation part. The other types of touch panels may be used.

Instead of the touch panel, the operation panel 12a may detect a touch position by processing an image captured by the capturing means such as a camera. Specifically, the operation panel 12a is configured to be translucent and includes the surface 12a1 functioning as a touch operation panel. The operation panel 12a is provided with the light source 12c. When an approaching object approaches the touch operation panel 12a1, the light source 12c radiates light of a predetermined waveband to the approaching object through the operation panel 12a. The camera 12b functioning as the hand image capturing means is used as a capturing means. The light is radiated from the light source 12c and is reflected on the approaching object. The camera 12b detects at least the reflected light to capture the approaching object from the second surface 12a2 of the operation panel 12a1. The control circuit 18 functions as a reflecting area specification means for specifying a reflecting area that is contained in the image captured by the camera 12b and allows the reflected light to exceed a predetermined threshold intensity. The control circuit 18 also functions as an input acceptance means for accepting touch input to the reflecting area based on the specified reflecting area.

According to this configuration, an image captured by the camera 12b may contain the reflecting area detected to exceed the predetermined threshold intensity. In this case, the control circuit 18 assumes a touch input to the detected reflecting area and accepts the input. The image captured by the camera 12b is used for not only displaying the position indication image but also detecting the reflecting area. The control circuit 18 may also be configured to accept a touch input to the reflecting area when the detected reflecting area exceeds a predetermined threshold size.

According to all the above-mentioned embodiments, the input operation mode is assigned the operation part operable from the driver's seat and the passenger seat. The input operation mode may be assigned to an operation part operable from the other seats or only from one of the driver's seat and the passenger seat.

Third Embodiment

Figure 21:
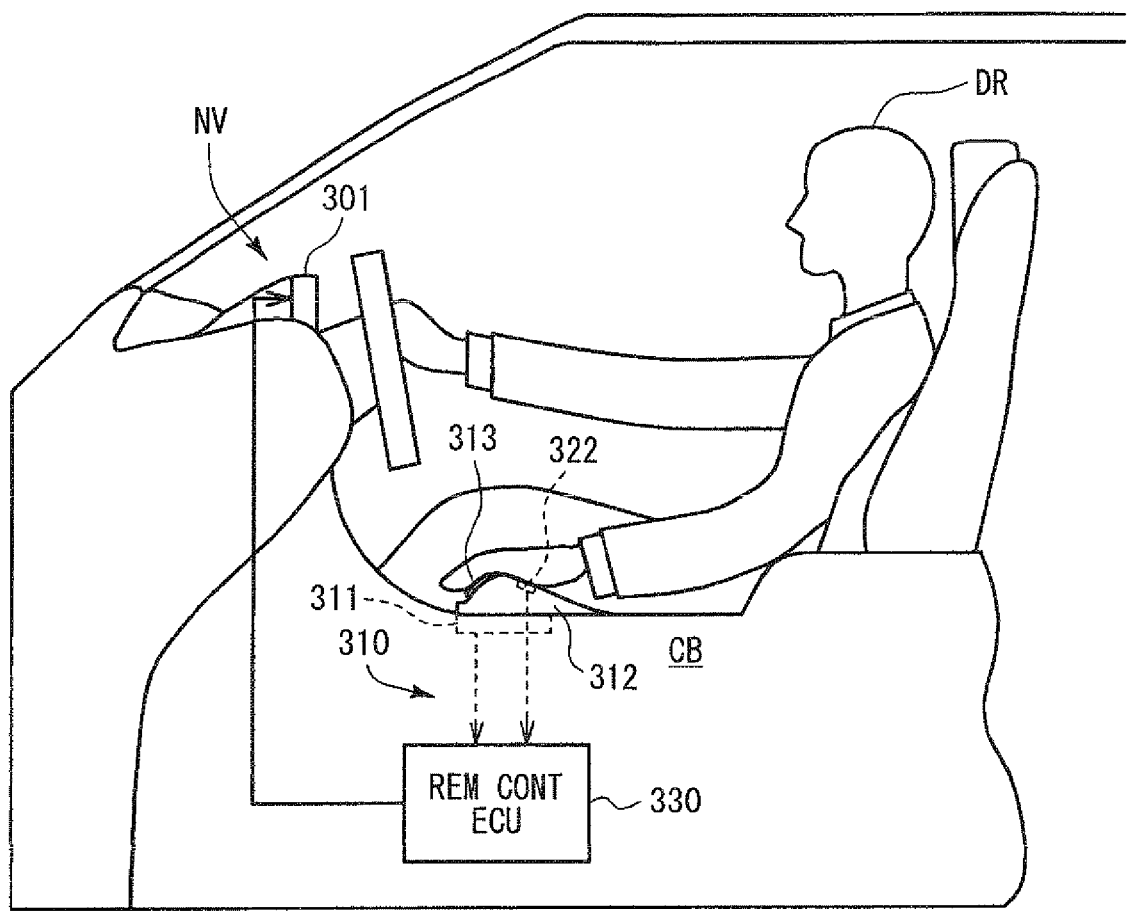
FIG. 21 schematically shows a car navigation system equipped with a remote control apparatus according to a third embodiment.

The third embodiment will be described in further detail with reference to the accompanying drawings. FIG. 21 schematically shows a car navigation system NV (onboard device) equipped with a remote control apparatus 310. A display unit 301 of the car navigation system NV is provided for front part of a vehicle interior near the view of a driver DR or a position far from the driver's seat toward the front. The display unit 301 displays a vehicle symbol on a map for navigation and notifies the driver DR of various information such as traffic information.

Figure 22A:
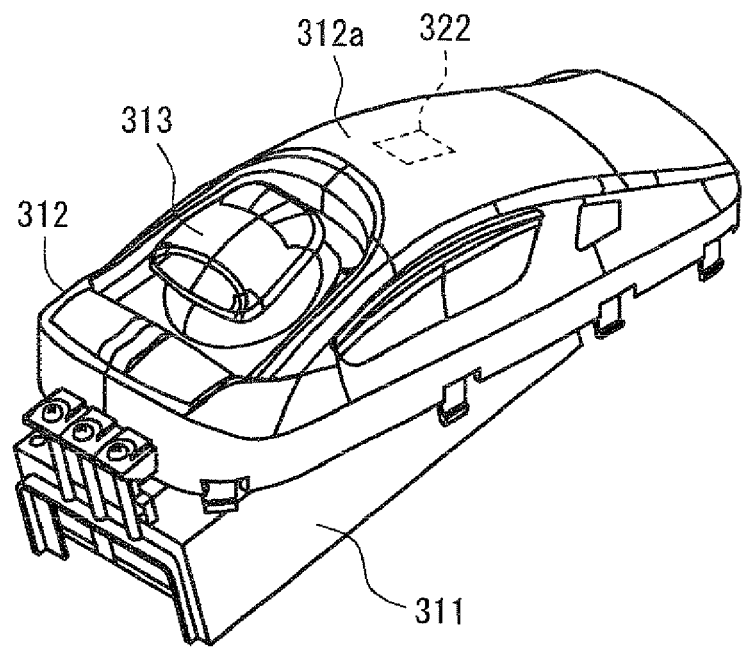
FIGS. 22A and 22B are perspective views of a device, a case, and a knob included in the remote control apparatus in FIG. 21.
Figure 22B:
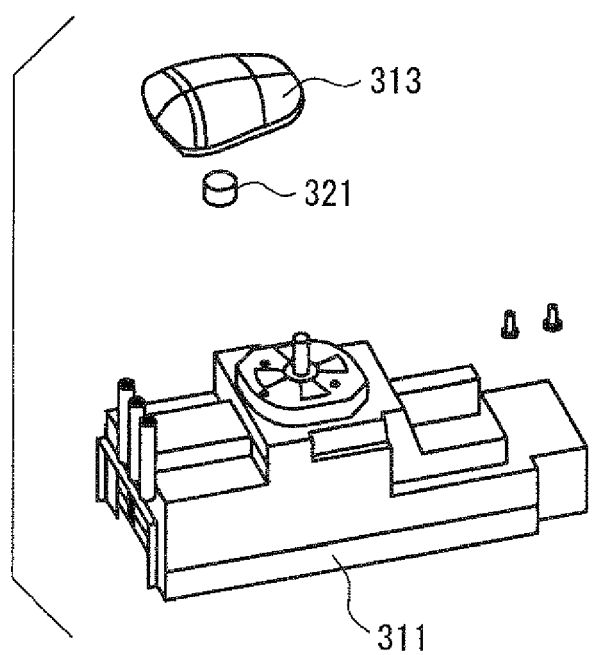

The remote control apparatus 310 is used to indirectly operate switches displayed on the display unit 301. The remote control apparatus 310 is assembled in a console box CB near a palm of the driver's left hand (or right hand in a left hand drive car) so that the driver can easily operate the apparatus. As shown in FIGS. 22A and 22B, the remote control apparatus 310 includes a device 311, a case 312 covering the top of the device 311, and a knob 313. The knob 313 is arranged so that a specified portion of the same protrudes from an opening of the case 312.

The device 311 (operation means) is connected to a remote control ECU 330 and transmits an operation signal to the remote control ECU 330. The operation signal corresponds to an operation of the knob 313 or to a rocking amount of the same as will be described later. The case 312 is approximately streamlined and forms a palm rest 312a between the center to the rear for placing a palm.

Figure 23:
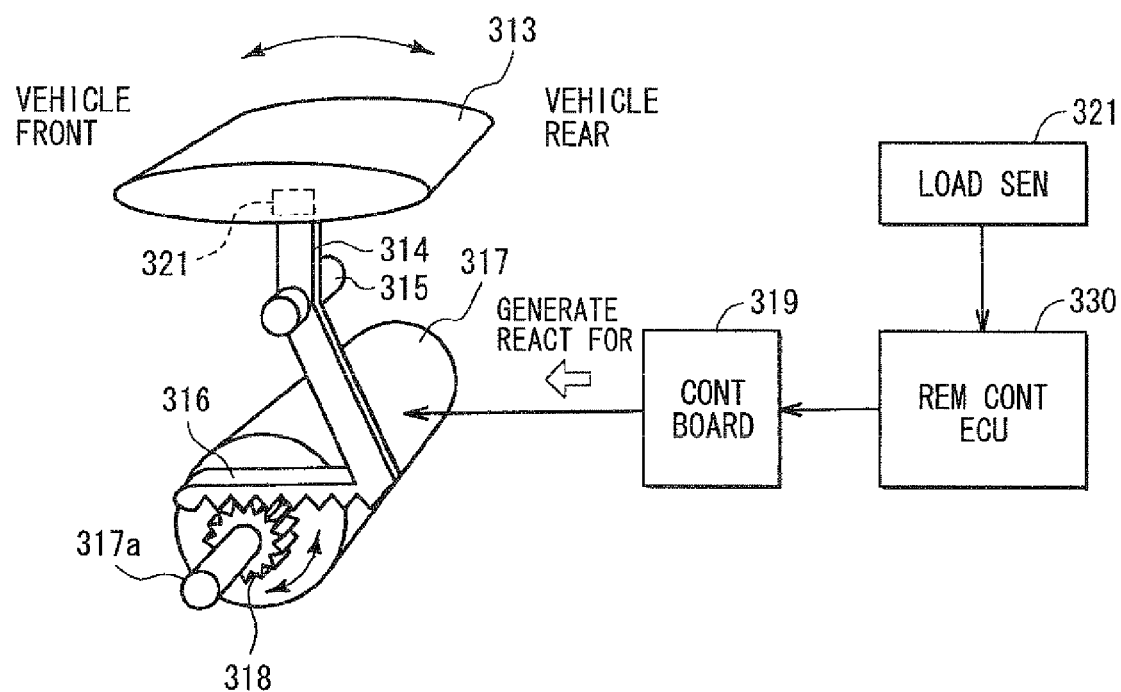
FIG. 23 is a perspective view schematically showing a mechanism of locking the knob in FIGS. 22A and 22B.

As shown in FIG. 23, the knob 313 (operation part) is coupled to the device 311 via a shaft part 314 and a rocking shaft 315. The knob 313 is capable of rocking in the front-back direction of the vehicle around the rocking shaft 315. The shaft part 314 extends approximately perpendicularly to the rear of the knob 313 as a rear anchor. The rocking shaft 315 extends along the left-right direction (width direction) of the vehicle at the middle of the shaft part 314. The knob 313 is coupled to a pinion gear 318 via the shaft part 314 and a rack gear 316 so as to be able to transmit motive energy. The rack gear 316 extends along the front-back direction of the vehicle below the shaft part 314. The pinion gear 318 is fixed to a drive shaft 317a of a motor 317.

The motor 317 is contained in the device 311 and is connected to a control board 319 (drive circuit) attached to the device 311. When the control board 319 supplies a drive current to the motor 317, a drive force (reactive force) of the motor 317 is transmitted to the knob 313 to prevent the knob 313 from operating around the rocking shaft 315. That is, the knob 313 is locked. When the control board 319 stops supplying the drive current to the motor 317, the drive force (reactive force) of the motor 317 is not transmitted to the knob 313 to allow the knob 313 to operate freely around the rocking shaft 315. That is, the knob 313 is unlocked. The motor 317 and the control board 319 function as a locking means.

A load detection means 321 is provided between the knob 313 and the rear anchor of the shaft part 314. The load sensor 321 (load detection means) includes a load cell or a pressure type sensor, for example. The load sensor 321 detects a pressure load applied to the knob 313 and transmits a corresponding sensor signal to the remote control ECU 330. The load sensor 321 can be provided in a narrow space between the knob 313 and the rear anchor of the shaft part 314.

Figure 24:
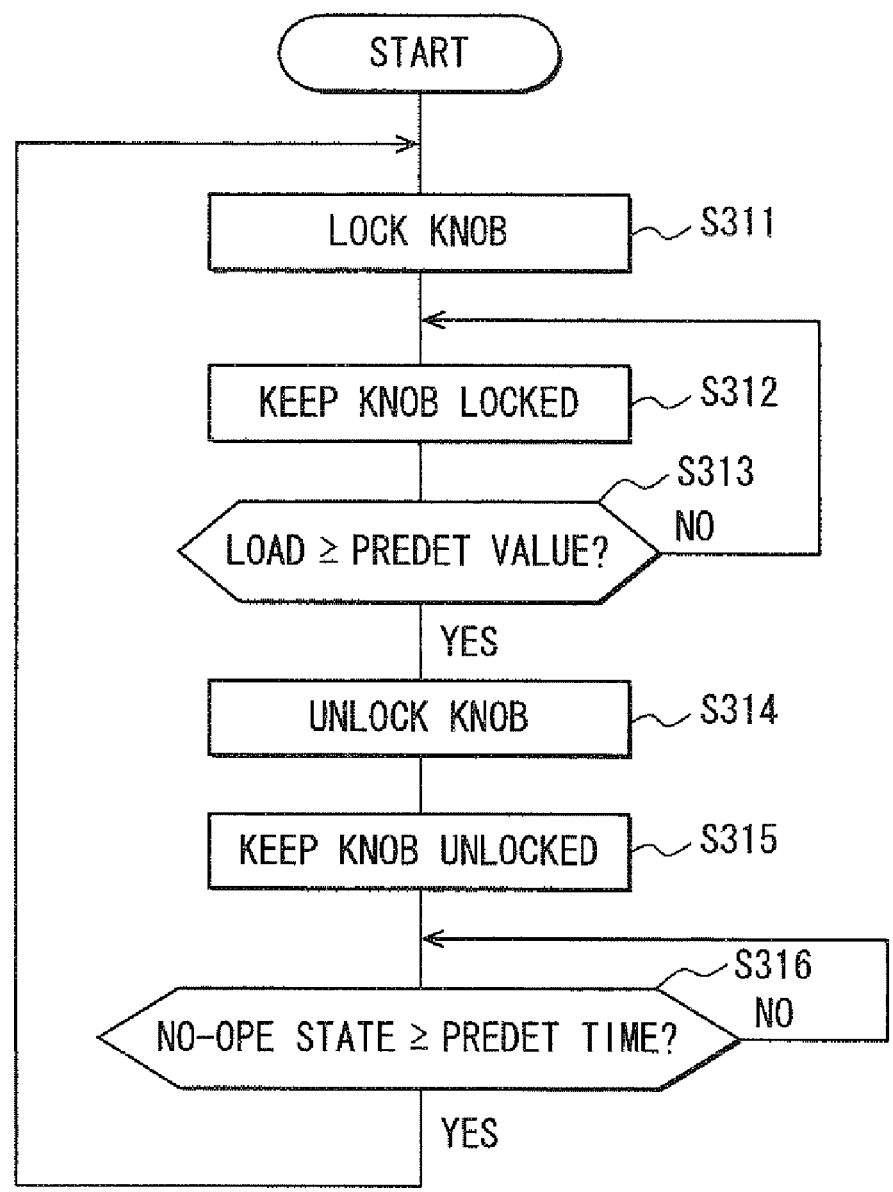
FIG. 24 is a flow chart showing a knob lock control program according to the first embodiment performed by the remote control ECU in FIG. 21.

The remote control ECU 330 (control means) mainly includes an unshown microcomputer containing a CPU, ROM, RAM, and input/output device. For example, the remote control ECU 330 turns on or off a switch displayed on the display unit 301 based on an operation signal from the device 311. In addition, the remote control ECU 330 repeatedly executes a knob lock (device lock) control program stored in ROM, for example. The knob lock control program is shown in FIG. 24.

The following describes operations of the first embodiment configured as mentioned above. When an ignition switch is turned on, the remote control ECU 330 repeatedly executes the knob lock control program in FIG. 24 at a specified short time interval.

Initially, the control board 319 is configured to supply a drive current to the motor 317. When the motor 317 generates a drive force (reactive force), the knob 313 is locked (S311) and remains locked (S312). The knob 313 remains locked unless a user touches the knob 313 (No at S313).

The control board 319 stops supplying the drive current to the motor 317 when the user presses the knob 313 with a more load than specified (Yes at S313). Since the motor 317 also stops generating the drive force (reactive force), the knob 313 is unlocked (S314) and remains unlocked (S315). For example, the specified load is designed to be 1 to 5 kgf that is not applied to the knob 3L3 during a normal rocking operation.

While the knob 313 is unlocked, the knob 313 can be freely rocked to enable an input operation on the knob 313. The knob 313 remains unlocked while the knob 313 is continuously used for the input operation (No at S316).

There may be a case where the knob 313 is not used for input operation and a no-input-operation state continues for a predetermined time such as 30 seconds or longer (Yes at S316). In this case, the control board 319 supplies a drive current to the motor 317 to lock the knob 313 (S311).

As is clear from the above-mentioned description, the first embodiment assumes the absence of a user intention to operate the knob 313 when a load detected by the load sensor 321 is smaller than the predetermined value (No at S313). The knob 313 remains locked under control of the motor 317 and the control board 319 in accordance with the remote control ECU 330 (S312). On the other hand, the first embodiment assumes the presence of a user intention to operate the knob 313 when a load detected by the load sensor 321 is greater than or equal to the predetermined value (Yes at S313). The knob 313 is unlocked under control of the motor 317 and the control board 319 in accordance with the remote control ECU 330 (S314).

When the user inadvertently operates the knob 313 of the remote control apparatus 310, a load detected by the load sensor 321 is smaller than the predetermined value. The motor 317 and the control board 319 keep the knob 313 locked and nullify an input operation on the knob 313.

In the first embodiment, there is a case where the knob 313 is unlocked under control of the motor 317 and the control board 319 in accordance with the remote control ECU 330 (S314) and no input operation is performed on the knob 313 afterwards for a predetermined time period (Yes at S316). In this case, the knob 313 is locked under control of the motor 317 and the control board 319 in accordance with the remote control ECU 330 (S311).

In short, the knob 313 is locked when it can be assumed that the user does not intend to operate the knob 313. This makes it possible to effectively prevent the user from inadvertently operating the knob 313.

Fourth Embodiment

According to the third embodiment, the knob 313 is locked when it remains unlocked and the no-input-operation state continues for the predetermined time period or longer. For example, it may be also preferable to provide a palm detection sensor 322 as indicated by a broken line in FIGS. 21 and 22A. The remote control ECU 330 may execute a knob lock control program as shown in FIG. 25 based on a detection result from the palm detection sensor 322.

The palm detection sensor 322 (palm detection means) includes an infrared sensor, a micro switch, and a pressure-sensitive sheet, for example. The palm detection sensor 322 is attached to the palm rest 312a. When the palm of the driver DR is placed on the palm rest 312a, the palm detection sensor 322 transmits an on-signal to the remote control ECU 330.

Figure 25:
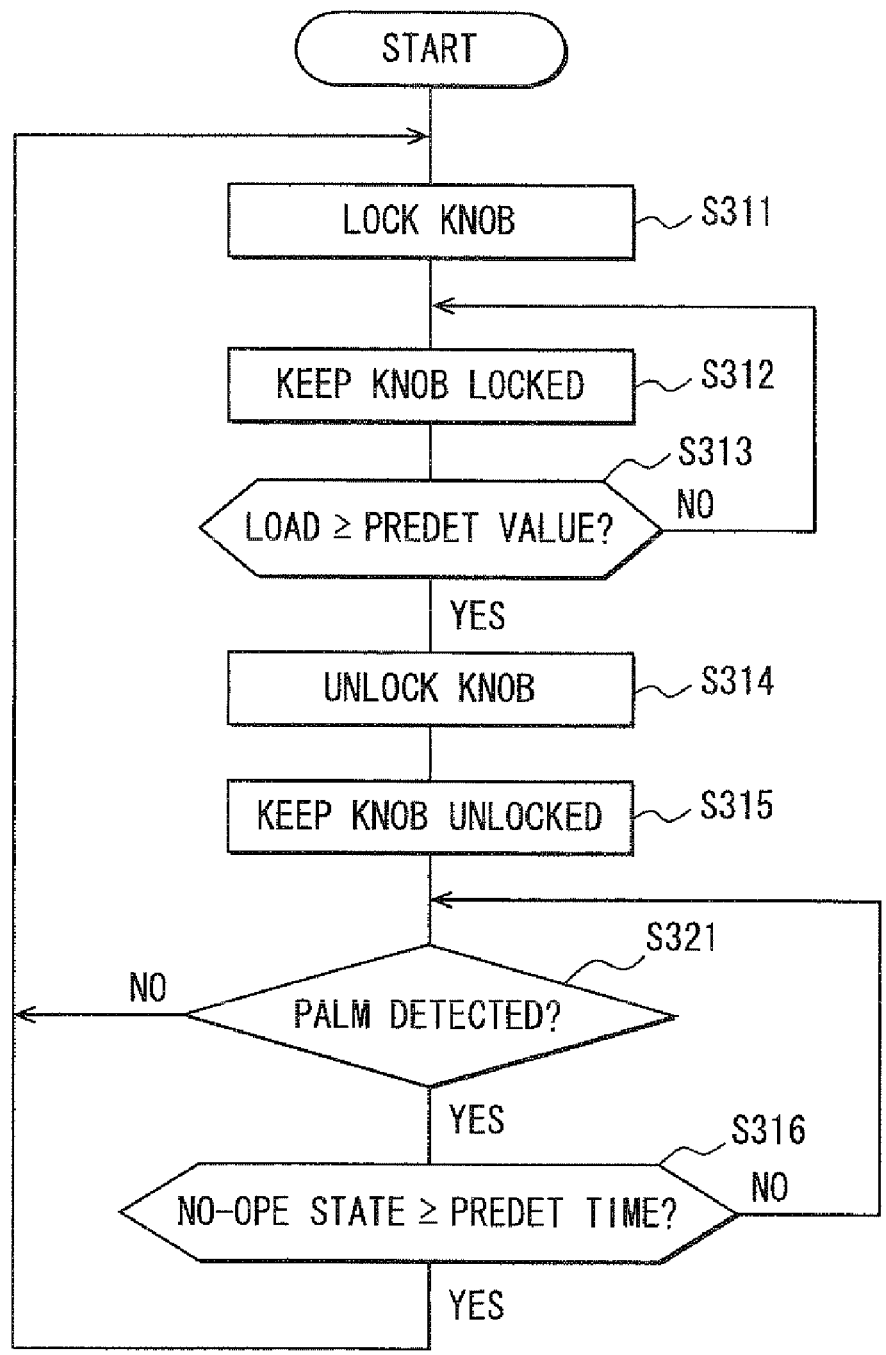
FIG. 25 is a flow chart showing a knob lock control program according to a fourth embodiment performed by the remote control ECU in FIG. 21.

The knob lock control program in FIG. 25 includes S321 in addition to the knob lock control program in FIG. 24. According to the knob lock control program in FIG. 25, the knob 313 remains unlocked (S315). Even before the no-input-operation state exceeds the predetermined time period (No at S316), the palm detection sensor 322 may not detect a palm or may transmit no on-signal (No at S321). In this case, the knob 313 is locked under control of the motor 317 and the control board 319 in accordance with the remote control ECU 330 (S311).

When the user releases his or her palm from the palm rest 312a, he or she may be assumed to indicate no intention to operate the knob 313. In this case, the knob 313 is locked even when the load sensor 321 detects a load greater than or equal to the predetermined value (Yes at S313). This makes it possible to more reliably prevent the user's inadvertent operation.

In the first and second embodiments, the load sensor 321 detects a pressure load on the knob 313. Instead, for example, a strain gauge may detect a pull-up load of the knob 313. A torque sensor may detect a rocking load (torque) of the knob 313.

Fifth Embodiment

Figure 26:
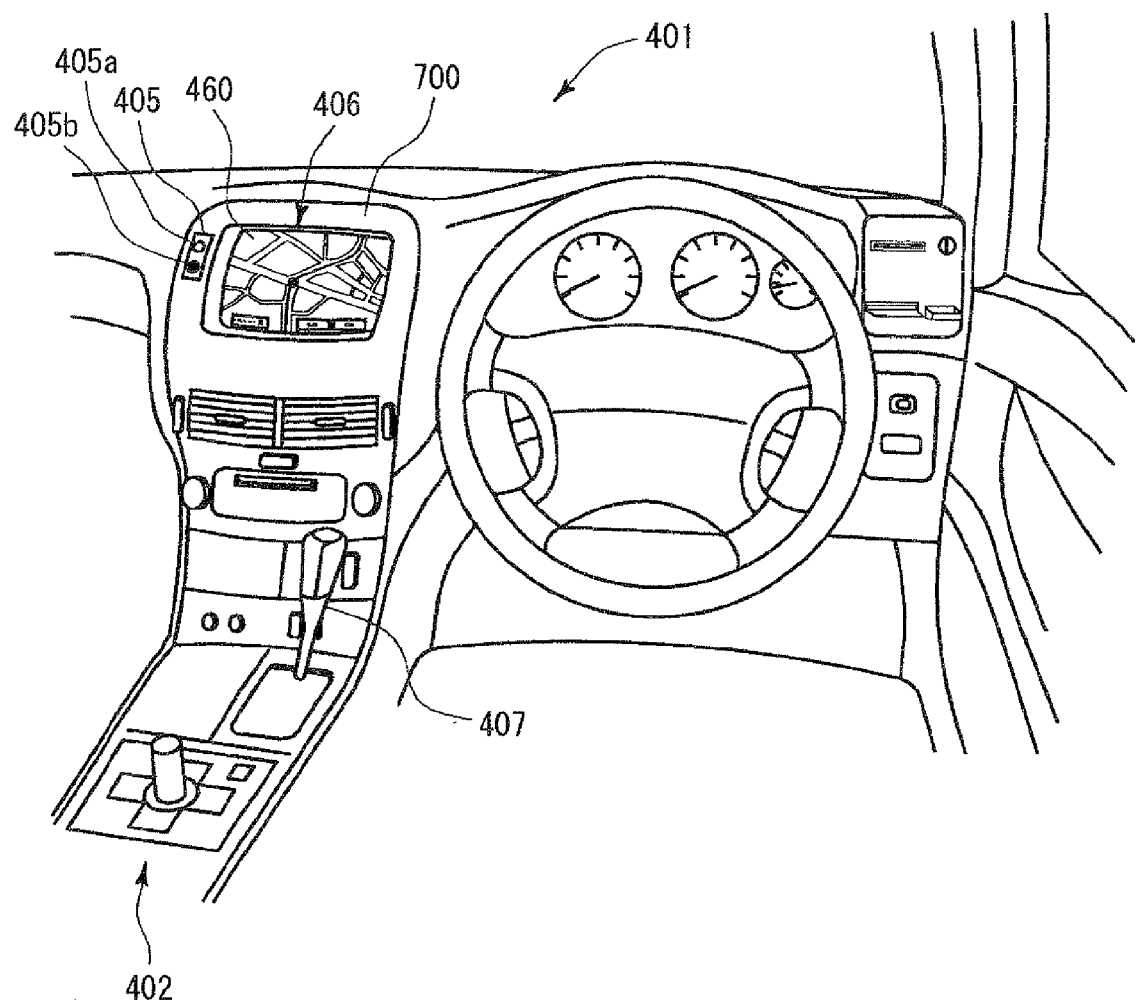
FIG. 26 shows an overall configuration of a vehicular operating device according to a fifth embodiment.
Figure 27:
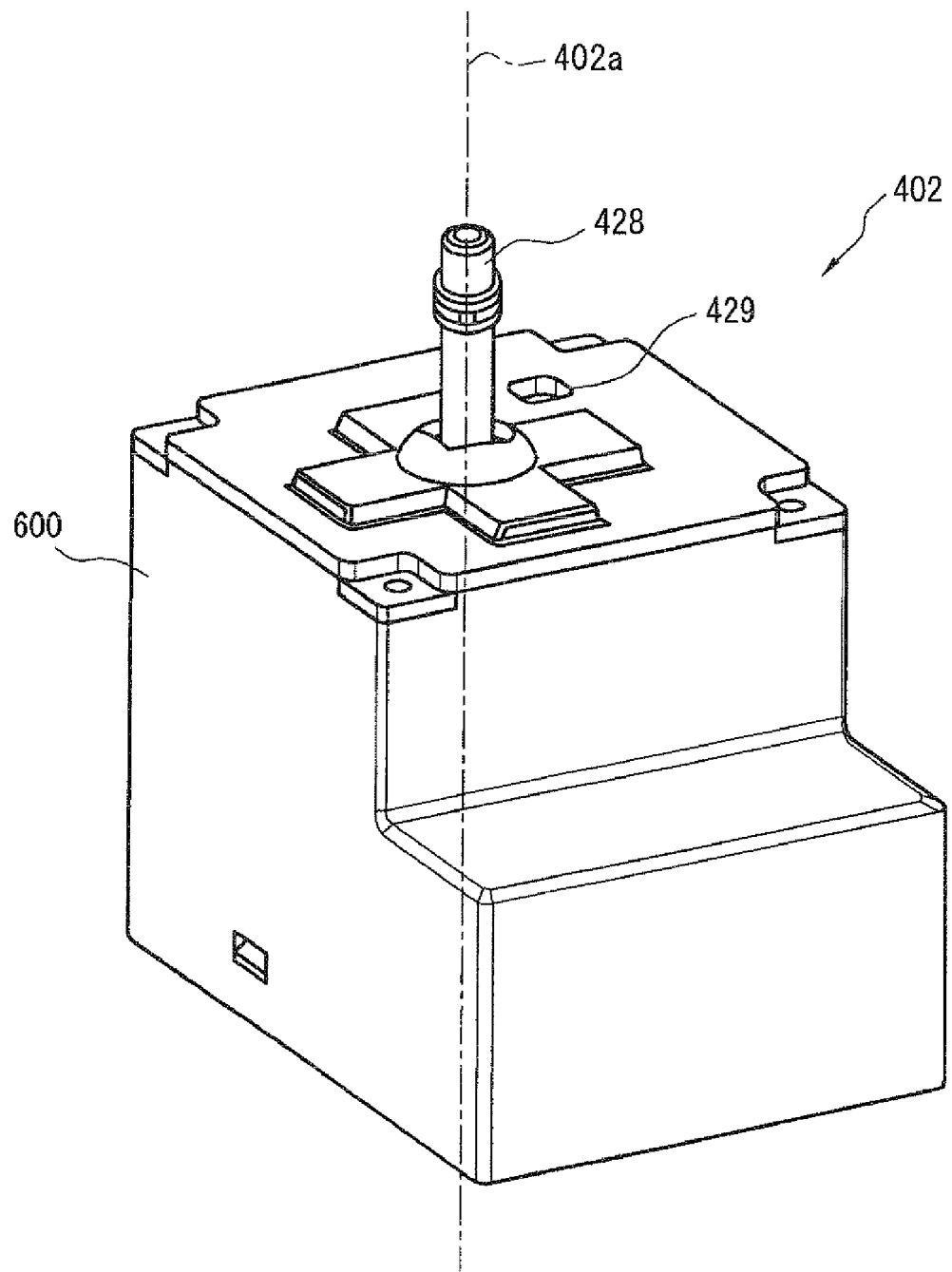
FIG. 27 is a perspective view of a pointer operation part.
Figure 28:
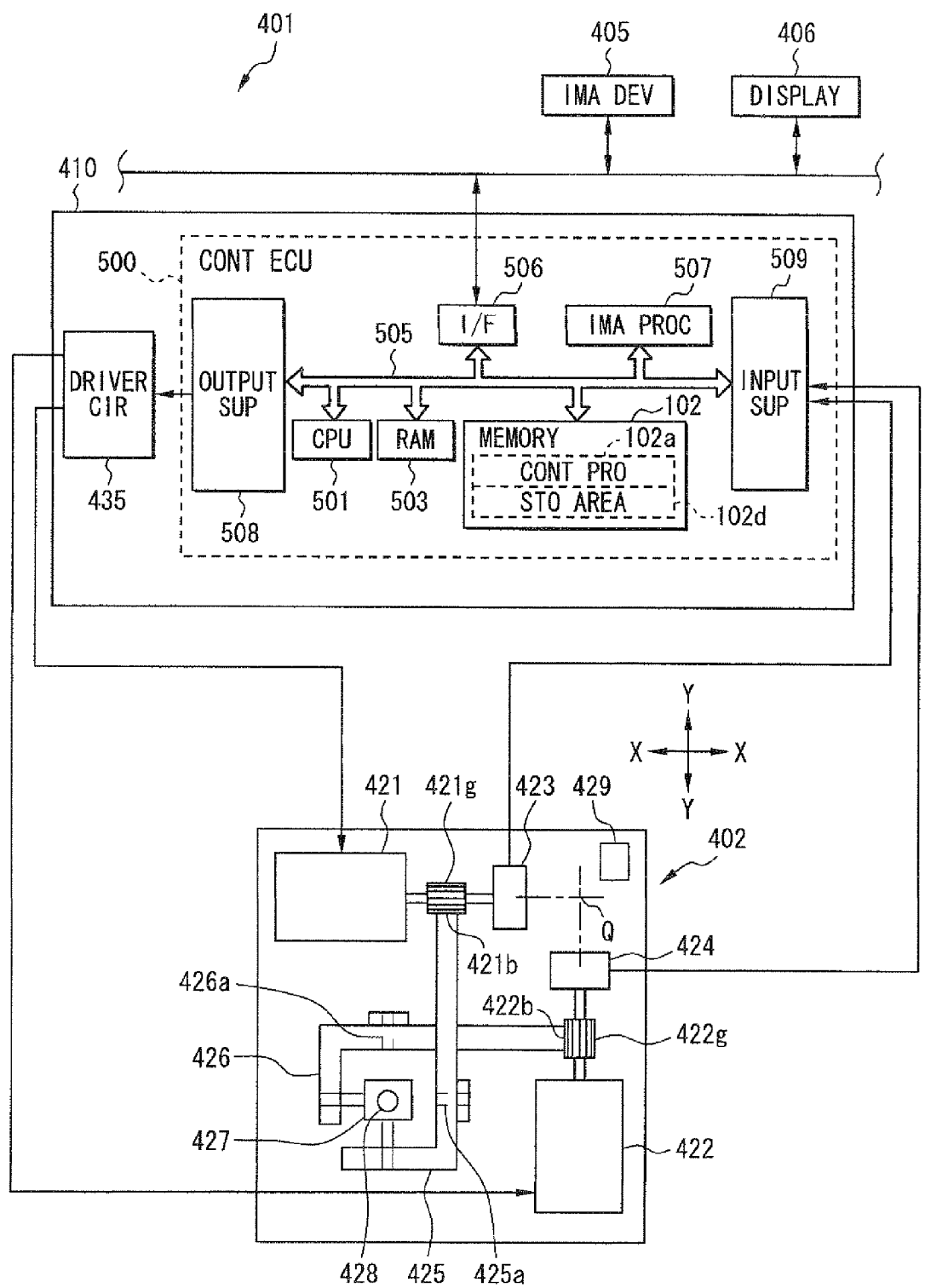
FIG. 28 contains a plan view showing an internal structure of the pointer operation part and a block diagram of a controller connected with the pointer operation part.

FIG. 26 shows an overall configuration of a vehicular operating device 401 according to a fifth embodiment. FIG. 27 is a perspective view of a haptic device 402 or a tactile device hereafter referred to as a pointer operation part. FIG. 28 contains a plan view showing an internal structure of the pointer operation part 402 and a block diagram of a controller 410 connected with the pointer operation part.

As shown in FIG. 26, the vehicular operating device 401 includes the pointer operation part 402, an imaging device 405, a display device 406, and a controller 410. The imaging device 405 is capable of capturing at least a driver's head. The display device 406 is attached to an instrument panel center 700 of the vehicle along a direction different from the driving direction. The controller 410 controls these components (see FIG. 28).

The pointer operation part 402 is attached to the rear of a gear shift lever 407 at the center console, for example, within the reach of the driver as a user. The pointer operation part 402 functions as a pointing device and is used to specify or select a position on a display screen 460 of the display device 406.

The pointer operation part 402 moves pointer P (see FIG. 29) on the display screen 460 of the display device 406. As shown in FIG. 27, a joystick-like operation lever 428 protrudes upward from inside a case 600. A user can use the operation lever 428 to select an onboard device or adjust the function. The pointer operation part 402 is equivalent to a tactilely operated device.

As shown in FIG. 28, a base 420 forms a bottom of the case 600 in FIG. 27. First and second rotary motors 421 and 422 and first and second rotary encoders 423 and 424 are mounted on the base 420. The first and second rotary encoders 423 and 424 are coupled to rotary shafts of the rotary motors 421 and 422. The rotary shaft of the first rotary motor 421 is orthogonal to that of the second rotary motor 422. The first and second rotary encoders 423 and 424 are placed near intersection point Q where the rotary shafts of the rotary motors 421 and 422 intersect with each other.

The base 420 rotatably supports first and second drive levers 425 and 426. The operation lever 428 is coupled to the driver levers 425 and 426 through a driving body 427. The first driver lever 425 is rotatable around a shaft 425a parallel to the rotary shaft of the first rotary motor 421. The first drive lever 425 is tipped with a tooth part 21b that engages with a gear 421g fixed to the rotary shaft of the first rotary motor 421. The second driver lever 426 is rotatable around a shaft 26a parallel to the rotary shaft of the second rotary motor 422. The second drive lever 426 is tipped with a tooth part 22b that engages with a gear 422g fixed to the rotary shaft of the second rotary motor 422.

The first and second rotary motors 421 and 422 and the first and second rotary encoders 423 and 424 are connected to the controller 410. The controller 410 is supplied with signals output from the first and second rotary encoders 423 and 424 and outputs specified control signals to the first and second rotary motors 421 and 422.

An approach sensor 429 is attached near the operation lever 428 on the top of the case 600. The approach sensor 429 uses at least one of the following to detect whether or not a user's hand approaches.

Infrared sensor: Detects heat from the user's hand.

Ultrasonic sensor: Generates an ultrasonic wave to detect an object or the user's hand that approaches the pointer operation part 402.

Radar: Generates an electric wave to detect an object or the user's hand that approaches the pointer operation part 402.

Electrostatic sensor: Checks for a change in electrostatic capacitance to detect an object or the user's hand.

When imaging is available in a visible light region, for example, the imaging device 405 uses a camera 405a (see FIG. 26) to capture visible light reflected on an occupant's face or eyeball. When imaging is available in an infrared ray region, the imaging device 405 uses the camera 405a to capture an infrared ray reflected on an occupant's eyeball. The infrared ray is radiated from an appropriate infrared ray projector 405b (see FIG. 26) to the occupants eyeball. The captured data is transmitted to a controller ECU 500.

Figure 29:
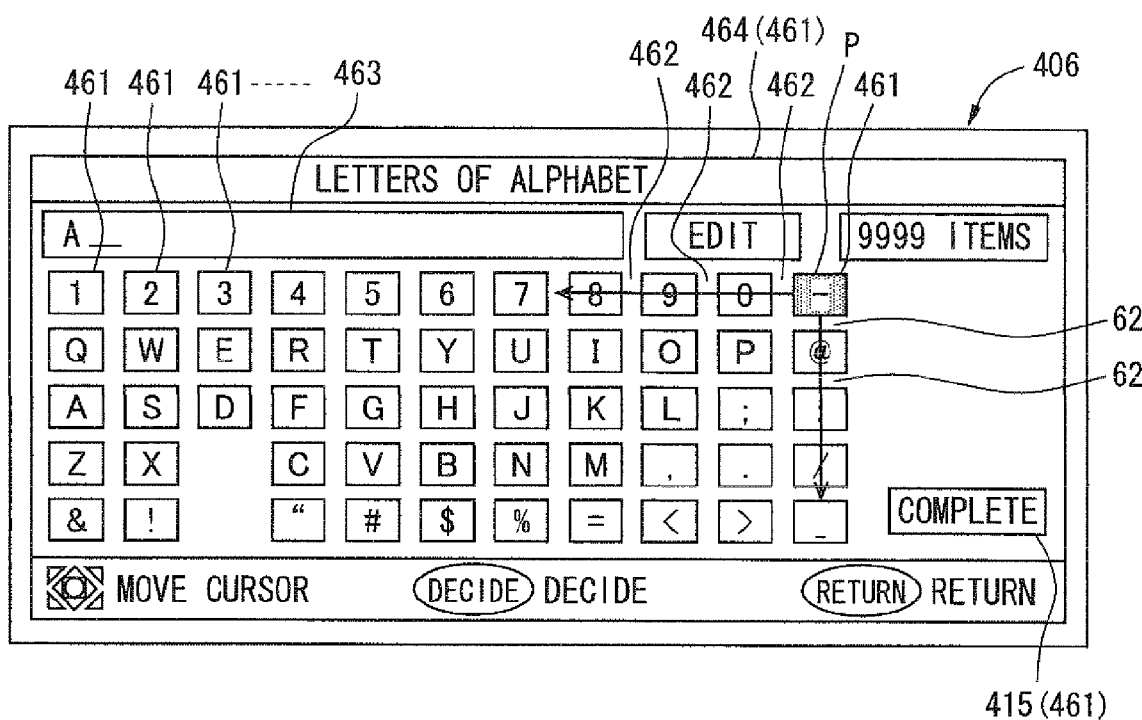
FIG. 29 shows an example display screen on a display device.

The display device 406 is configured as an LCD display device, for example. The display device 406 displays a pointer-selected display screen (hereafter also referred to as a display screen for short) 460 as shown in FIG. 29. Part of the display screen 460 is segmented to provide multiple input selection areas 461 adjacent to each other. Pointer P can be used to select any one of the input selection areas 461. The display screen 460 identifiably displays the input selection area 461 selected by pointer P. On the pointer-selected display screen 460, the input selection area 461 functions as an icon image area that displays an icon image. A non-selectable area 462 is provided between adjacent icon image areas. The non-selectable area 462 is not selected by pointer P. The display device 406 is equivalent to a display means.

The pointer-selected display screen 460 in FIG. 29 exemplifies a character input screen. A display color of the character icon image 461 is inverted when pointer P selects a character icon image 463 (461). While the character icon image 463 is selected, operating an unshown submit switch sequentially displays a character corresponding to the selected character icon image 463 (461) in a character display area 463. The user repeats this operation until the character input is complete. Upon completion, the user selects a complete icon image 465 (461) and then selects a submit button on the screen or operates the submit switch provided elsewhere.

To change an input character, the user selects an edit icon image 464 (461) and then operates the submit switch. This operation deletes the most recently input character one by one. The submit switch may be provided as a push switch (not shown) at the top end of the operation lever 428 of the pointer operation part 402. Using only the operation lever 428, the user can easily move pointer P, input characters, and complete the input operation.

The pointer-selected display screen 460 in FIG. 29 represents a character input screen, but the screen for the display means is not limited thereto. The pointer-selected display screen may be as the character input screen that densely includes many input selection areas 461.

Now returning back to FIG. 28, the controller 410 includes a controller ECU (Electronic Control Unit) 500 that controls the pointer operation part 402. The controller ECU 500 represents a microcomputer including a CPU 501, nonvolatile memory 502, RAM 503, an image processing part 507, an output support 508, and an input support 509 that are connected to each other through a bus 505. A serial communication interface (I/F) 506 connects the bus 505 inside the controller ECU 500 with a serial communication bus 409 for in-vehicle network. The nonvolatile memory 502 stores a control program 502a executed by the CPU 501 and data needed for the program. The RAM 503 is used as a work area when the CPU 501 executes the control program 502a. The CPU 501 is equivalent to an operation determination means.

The controller 410 receives a position detection signal (output pulse) fed back from the first and second rotary encoders 423 and 424 through the input support 509. The controller 410 acts on the position detection signal fed back from the first and second rotary encoders 423 and 424 and determines in which directions the rotary motors 421 and 422 rotate at which angles. The controller 410 supplies a drive control signal for the rotary motors 421 and 422 based on a determination result to a driver circuit 435 for the rotary motors 421 and 422 through the output support 508. The driver circuit 435 drives the rotary motors 421 and 422 based on the supplied drive control signal.

The controller 410 detects a direction in which the pointer operation part 402 is operated using the position detection signal fed back from the first and second rotary encoders 423 and 424. The controller 410 drives the motors 421 and 422 so as to apply a reactive force against the operation direction for return to a neutral position or an auxiliary pulling force along the operation direction.

The serial communication bus 409 is connected to the display device 406 provided for an instrument panel 700 of the vehicle. The controller 410 transmits a position detection signal from the first and second rotary encoders 423 and 424 or a press detection signal for the submit switch to the display device 406. When receiving the position detection signal or the press detection signal, the display device 406 performs a process for operations corresponding to the direction of operating the operation lever 428. The operations are displayed on the screen.

The nonvolatile memory 502 is provided with a pointer position storage area 102d that stores a position (operation axis state) of the pointer operation part 402. The operation axis state is calculated based on the position detection signal fed back from the first and second rotary encoders 423 and 424. The nonvolatile memory 502 is equivalent to an operation axis state storage means.

The image processing part 507 processes a visible light image or an infrared ray image generated by the imaging device 405. The image process includes filtering or digitization, for example. In this manner, the image processing part 507 generates image data that contains two-dimensional array pixels. The image processing part 507 recognizes a driver's eyeball. Based on a recognition result, the image processing part 507 detects the driver's eyeball position, the driver's visual line vector (visual line direction), and the position of an object to which the visual line is directed. Specifically, the image processing part 507 specifies an eyeball area from a face image and finds an eyeball center coordinate from the eyeball curvature. Further, the image processing part 507 specifies an iris area from the eyeball area to find an iris center coordinate. The image processing part 507 determines a visual line direction by finding a direction from the eyeball center coordinate to the iris center coordinate. In addition, detection of the visual line direction may also be done by the corneal reflex method or the limbus tracking method that uses infrared light. The image processing part 507 is equivalent to a visual line direction detection means.

Figure 30:
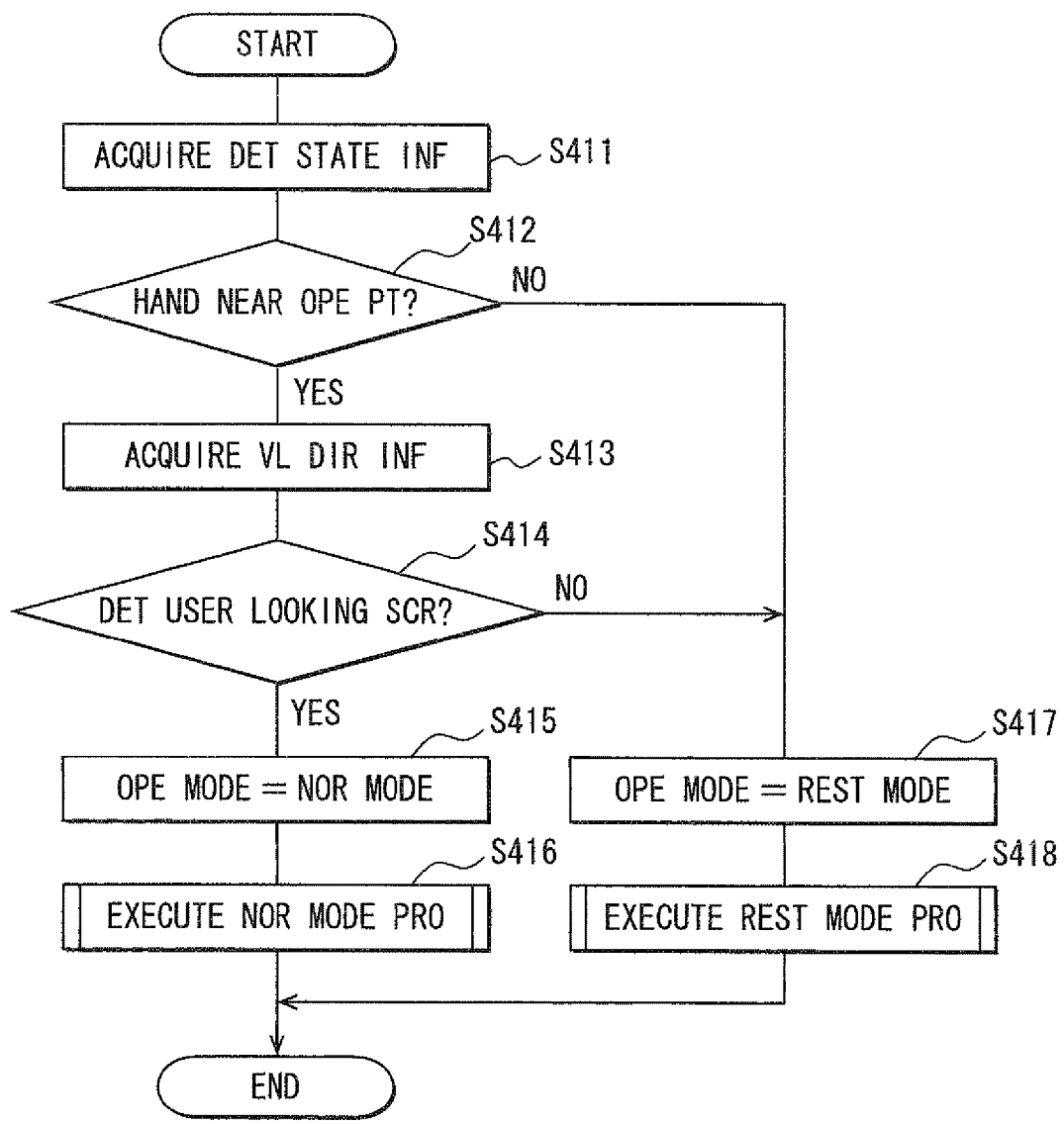
FIG. 30 is a flow chart showing an operation mode control process.

With reference to FIG. 30, the following describes an operation mode control process included in the control program 502a. The CPU 501 repeatedly executes the operation mode control process along with the other processes of the control program 502a. The operation mode control process acquires information about a detection state from the approach sensor 429 (S411). Based on the approach sensor information, the process determines whether or not user's hand exists near the pointer operation part 402.

The process may determine that the user's hand does not exist near the pointer operation part 402 (No at S412). In this case, the process selects restriction mode as the operation mode (S417). To do this, for example, the process sets an operation mode flag to 1. The operation mode flag is stored in the RAM 503. The process then passes control to a process in the restriction mode (S418) to be described later.

The process may determine that the user's hand exists near the pointer operation part 402 (Yes at S412). In this case, the process acts on an image captured by the imaging device 405 and acquires information about the driver's visual line direction detected by the image processing part 507 (S413). Based on the information about the visual line direction, the process determines whether or not the user looks at the display screen 460 of the display device 406.

The process may determine that the user does not look at the display screen 460 of the display device 406 (No at S414). In this case, the process selects restriction mode as the operation mode (S417). The process sets the operation mode flag to 1 and performs a process in the restriction mode (S418) to be described later.

The process may determine that the user looks at the display screen 460 of the display device 406 (Yes at S414). In this case, the process selects normal mode as the operation mode (S415). To do this, for example, the process sets the operation mode flag to 0. The operation mode flag is stored in the RAM 503. The process then passes control to a process in the normal mode (S416) to be described later.

Figure 31:
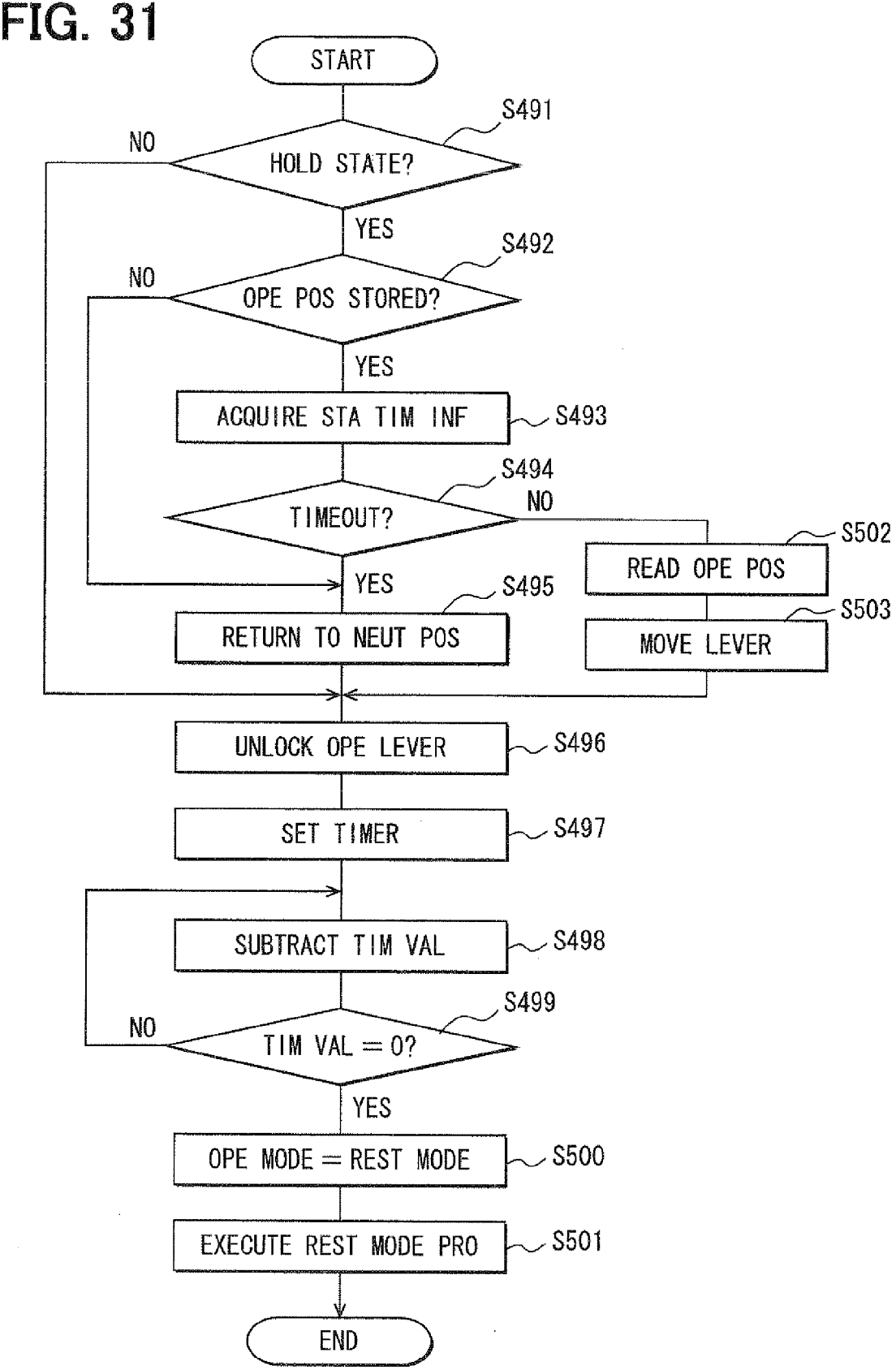
FIG. 31 is a flow chart showing a process in normal mode.

With reference to FIG. 31, the following describes the process in the normal mode corresponding to S416 in FIG. 30. The process references a hold flag in the RAM 503 and determines whether or not the pointer operation part 402 is held. The hold flag will be described in detail later on. The hold flag may be set to 1 to enable the hold state (Yes at S491). In this case, the process proceeds to S496 (to be described).

The hold flag may be set to 0 to disable the hold state (No at S491). In this case, the process determines whether or not the position (return point) of the pointer operation part 402 is stored. The position of the pointer operation part 402 may not be stored (No at S492) when the pointer position storage area 102d is empty. In this case, the process proceeds to S495 (to be described).

The position of the pointer operation part 402 may be stored (Yes at S492) when the pointer position storage area 502d is not empty. In this case, the process acquires information about a status timer (to be described) in the RAM 503. The status timer is decremented by another process such as an interrupt process. The process determines whether or not the timer is set to value 0 (timeout).

In S493, information about status timer is acquired. The status timer may not time out (No at S494). In this case, the process reads the content of the pointer position storage area 502d (S502). The content is equivalent to the position information about the pointer operation part 402. Thus, in S502, the position of the pointer operation part 402 is read out. The rotary motors 421 and 422 rotate to move the operation lever 428 to the corresponding position (S503).

The status timer may time out (Yes at S494). In this case, the rotary motors 421 and 422 rotate to return the operation lever 428 to the neutral position (S495).

The operation lever 428 may be locked or held. The process releases the state of the operation lever 428 (S496). The process resets the hold flag in the nonvolatile memory to 0. The process clears the content of the pointer position storage area 102d.

The process sets a timer that keeps track of the time period for allowing the user to operate the operation lever 428 (S497). The process decrements the timer value (S498). When the timer value becomes zero (Yes at S499), the process enables the restriction mode as the operation mode (S500). The process passes control to a process in the restriction mode (S501) to be described later. The process stops decrementing the timer value when detecting a user operation on the operation lever 428.

Figure 32:
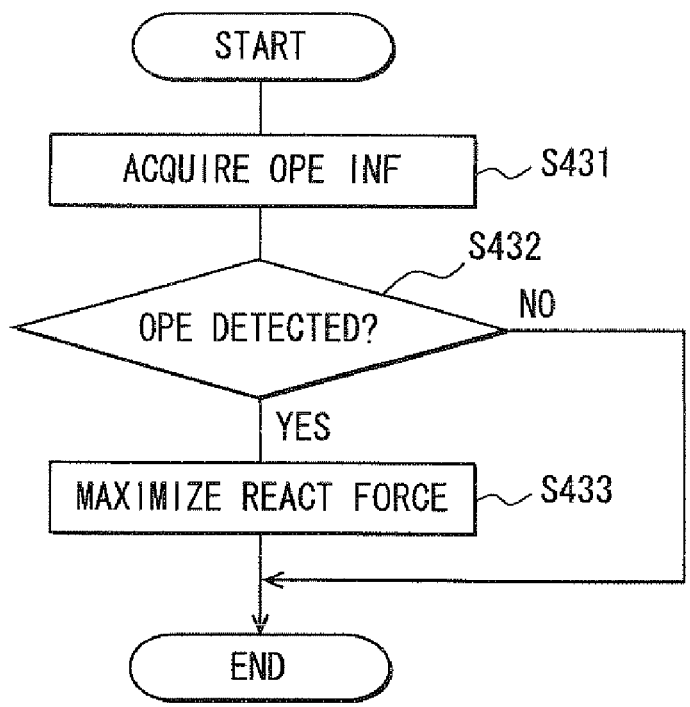
FIG. 32 is a flow chart showing a process in restriction mode.

With reference to FIG. 32, the following describes the operation in the restriction mode corresponding to S418 in FIG. 30 and S501 in FIG. 31. The process acquires information about the operation on the pointer operation part 402 (S431). Based on the acquired pointer operation part information, the process determines whether or not the user operates the operation lever 428. The first and second rotary encoders 423 and 424 feed back a positional variation. The process determines that the user operates the operation lever 428 (Yes at S432) when the positional variation exceeds a predetermined value. The process allows the rotary motors 421 and 422 to rotate and maximize a reactive force so that the user cannot operate the operation lever 428 (S433).

Figure 33:
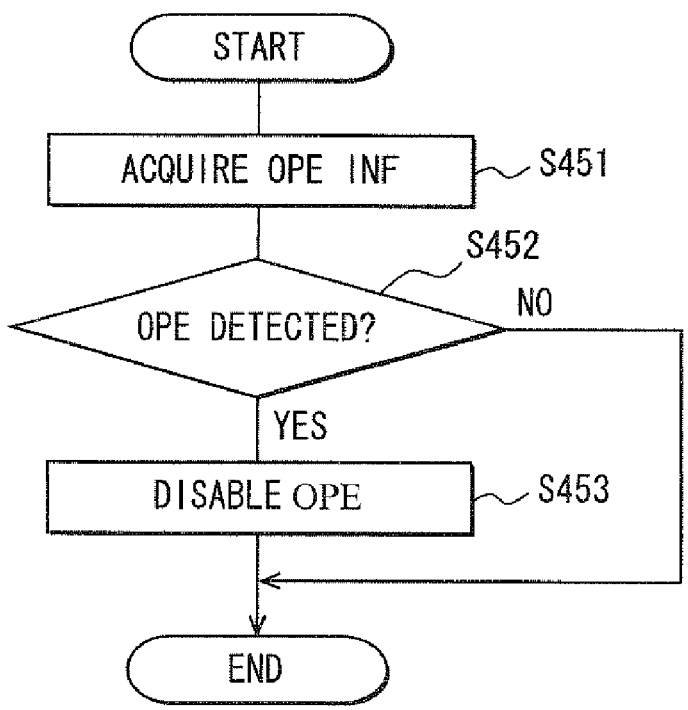
FIG. 33 is a flow chart showing another example process in restriction mode.

With reference to FIG. 33, the following describes another process in the restriction mode. The process acquires information about the operation on the pointer operation part 402 (S451). Based on the acquired pointer operation part information similarly to FIG. 32, the process determines whether or not the user operates the operation lever 428. The process may determine that the user operates the operation lever 428 (Yes at S452). In this case, the process nullifies the user operation and disables the cursor movement or indication on the display screen 460 of the display device 406 from being changed (S453).

Figure 34:
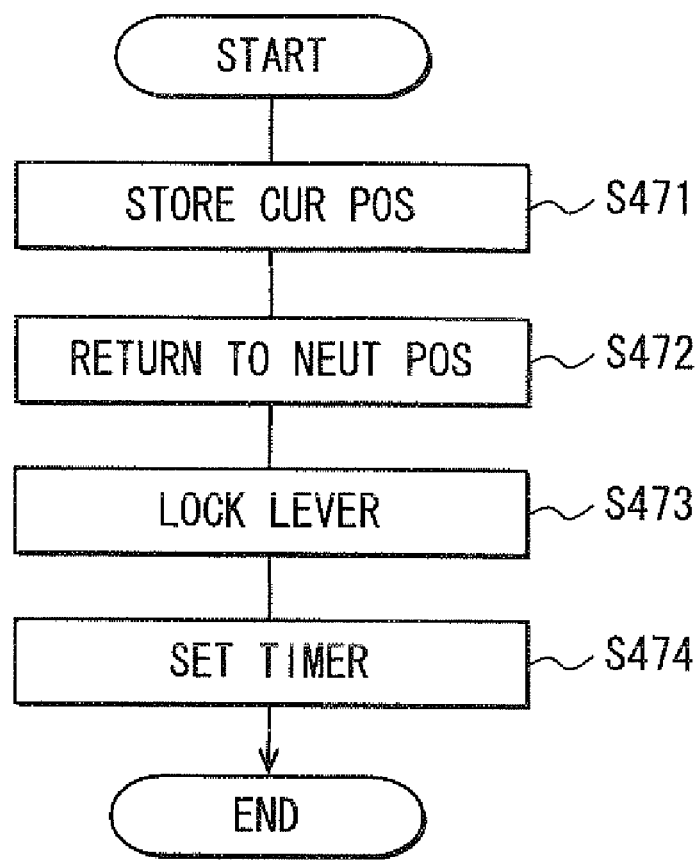
FIG. 34 is a flow chart showing still another example process in restriction mode.

With reference to FIG. 34, the following describes still another process in the restriction mode. The first and second rotary encoders 423 and 424 feed back positional information. Based on the positional information, the process allows the nonvolatile memory 502 to store the current position of the operation lever 428 of the pointer operation part 402 (S471). The position is stored in the pointer position storage area 102d of the nonvolatile memory 502. The current position is equivalent to the return point and represents the position of the operation lever 428 immediately before the restriction mode is enabled. The process allows the rotary motors 421 and 422 to rotate so that the operation lever 428 returns to the neutral position (S472). For example, the current position of the operation lever can be calculated as a variation in the first and second rotary encoders 423 and 424 based on the neutral position of the operation lever 428 as an origin. The rotary motors 421 and 422 just need to be rotated so that the position fed back from the first and second rotary encoders 423 and 424 approximates the origin.

The process then locks the operation lever 428 so as to prevent the user from using it (S473). When the user attempts to move the operation lever 428, for example, the process allows the rotary motors 421 and 422 to rotate and generate a reactive force so that the user cannot move the operation lever 428.

Without proceeding to S472, it may be preferable to hold the position of the operation lever 428 immediately before the restriction mode is enabled. In this case, the process sets the hold flag of the RAM 503 to 1. The process controls the rotary motors 421 and 422 so as not to generate reactive force and to prevent the operation lever 428 from returning to the neutral position.

Finally, the process sets the status timer in the RAM 503 to a timer value such as five minutes. This value specifies a time period for validating information about the position of the operation lever 428 immediately before the restriction mode is enabled (S474).

The above disclosure has the following aspects.

According to a first aspect of the present disclosure, an input apparatus for a vehicle includes: an operation element operable by an occupant of the vehicle; a biological information acquisition element acquiring biological information of the occupant; an unawakened state detection element detecting an unawakened state of the occupant based on the biological information, wherein the unawakened state is defined by a predetermined state different from an awakened state; and an operation disabling element disabling an operation input from the operation element when the unawakened state detection element detects the unawakened state.

According to the above-mentioned configuration, the vehicular input apparatus detects a lowered consciousness level as an unawakened state in which an occupant becomes drowsy. When the unawakened state is detected, the vehicular input apparatus disables any input operation, making it possible to prevent an incorrect operation. The detection of a predetermined unawakened state includes a case of comparing the acquired biological information with a predetermined unawakened state and a case of comparing the same with a predetermined normal awakened state.

Alternatively, the input apparatus may further include: a notification element notifying the occupant of disabling of the operation when the operation disabling element disables the operation. Thus, the operator can recognize that the operation is disabled. Further, the input apparatus may further include a display arranged on a front side of the vehicle and visible by the occupant, who sits down on a seat of the vehicle. The notification element controls the display to change a part of or all of a screen image on the display when the operation disabling element disables the operation. This configuration uses a display output and allows the operator to reliably recognize the disablement of the operation.

Alternatively, the input apparatus may further include: an awakening element awakening a driver of the vehicle. The occupant is the driver, and the awakening element awakens the driver when the operation disabling element disables the operation. The disabled operation can cause the driver to awake. Further, the input apparatus may further include: a notification element notifying the occupant of disabling of the operation when the operation disabling element disables the operation. The notification element functions as an awakening element for awakening a driver of the vehicle. The occupant is the driver, and the awakening element awakens the driver when the operation disabling element disables the operation. In this manner the operator can recognize that the operation is disabled. Even when the operator in an unawakened state makes unintentional operation, the operation can cause the operator to awake. Further, the awakening element may execute at least one of increasing an operation reaction force of the operation element, vibrating the operation element, increasing an operation sound of the operation element, changing the operation sound of the operation element, outputting an alarm sound, increasing a force for tightening a seat belt of the vehicle, vibrating the seat belt, and supplying air from an air conditioner of the vehicle. This configuration can reliably awaken the operator. The above-mentioned display output may function as a driver awakening means depending on output contents.

Alternatively, the occupant may be a driver of the vehicle. The biological information acquisition element acquires the biological information of the driver, and the operation element is arranged at a position where at least the driver sitting on a seat of the vehicle is capable of operating the operation element. The driver may be assumed to be a vehicle occupant who must not be unawakened. It is very effective to prevent incorrect operations, notify the operation disablement, and generate an awakening output for the driver.

Alternatively, the biological information acquisition element may include a pupil detection element for detecting a chronological change of a pupil of the occupant. The pupil detection element includes an eye image capturing element for capturing an eye image of the occupant, and the pupil detection element detects the chronological change of a pupil size of the occupant based on the eye image. It is possible to reliably detect an unawakened state as a mitotic state in which the detected pupil size continues to be under a specified level for a specified time or longer.

Alternatively, the biological information acquisition element may include a blink detection element for detecting a blink of the occupant. The blink detection element includes an eye image capturing element for capturing an eye image of the occupant, and the blink detection element detects the blink based on the eye image. It is possible to count the detected number of blinks and detect an unawakened state when the number of blinks exceeds a specified range within a predetermined time.

Alternatively, the biological information acquisition element may include a biological waveform detection element for acquiring at least one of a pulse waveform, a heartbeat waveform, an electrocardiographic waveform and a brain waveform of the occupant, and the biological waveform detection element contacts the occupant sitting on a seat of the vehicle. Detecting and analyzing the biological waveform makes it possible to reliably specify the unawakened state. The biological information about the occupant can be acquired while the occupant remains sitting on the seat. The occupant feels little inconvenience from the detection of the biological information. When the occupant is a driver, biological information can be acquired while he or she is driving. A biological waveform detection sensor can be provided for the bottom or the headrest of the seat. For driver's convenience, biological waveform detection sensor can be provided for a steering wheel or, more particularly, its ring.

Alternatively, the operation element may include a touch operation panel so that the occupant touches the panel to input operation. Just a contact with the tactile operation element may activate input. The tactile operation element easily causes an incorrect operation due to an unintentional contact. Such operation element is preferred for the invention capable of preventing incorrect operations. An operation element tending to cause incorrect operations is also preferred for the invention because the awakening output is frequently generated for such operation element.

Alternatively, the operation element may be arranged at a position where the occupant can operate the operation element even when the occupant sits down on a seat of the vehicle with leaning the occupant back on a backrest of the seat. When the operation element is positioned so as to be easily accessible to the occupant, such operation element is preferred for the invention capable of preventing incorrect operations. An operation element tending to cause incorrect operations is also preferred for the invention because the awakening output is frequently generated for such operation element.

Alternatively, the occupant may be a driver of the vehicle. The operation element is a remote operation element, which is arranged at a position nearer a driver seat than a main operation device. The remote operation element is separately disposed from the main operation device, and the remote operation element executes remote input into the main operation device. When a remote operation element is provided at a position more accessible and nearer than the main operation element, such remote operation element is preferred for the invention capable of preventing incorrect operations. An operation element tending to cause incorrect operations is also preferred for the invention because the awakening output is frequently generated for such operation element.

Alternatively, the input apparatus may further include: a display arranged on a front side of the vehicle and visible by the occupant, who sits down on a driver seat or a front passenger seat. The main operation device is a touch panel mounted on the display, and the remote operation element is arranged between a bottom of the driver seat and a bottom of the front passenger seat. Further, the input apparatus may further include: a hand image capturing element capturing a hand image of an operator, who operates the remote operation element; a hand image display element specifying an indicating position on the display based on the hand image and superimposing a position indication image at the indicating position on the display; a display mode setup element setting one of a display disabling mode and a display enabling mode of the hand image display element. The display disabling mode is set when the unawakened state detection element detects the unawakened state. The display enabling mode is set when the unawakened state detection element does not detect the unawakened state. The display disabling mode prohibits the hand image display element from superimposing the position indication image on the display, and the display enabling mode allows the hand image display element to superimpose the position indication image on the display. This configuration can eliminate an unnecessary image display process. This is because when the remote operation is based on a displayed position indication image, displaying a position indication image is meaningless while the operation is disabled.

Alternatively, the operation element may be at least one of an air conditioner operation element, an audio operation element, a navigation operation element, a power window operation element and a seat adjusting operation element.

According to a second aspect of the present disclosure, an input apparatus for a vehicle includes: an operation device operable by an operator in the vehicle; a visual line detection element detecting a visual line of the operator who operates the operation device; a releasing visual line determination element determining whether the visual line is disposed in a predetermined operation releasing visual line state; and an input operation mode setup element setting an input operation enable mode and an input operation disable mode. The input operation enable mode allows the operation device to input an operation from the operator. The input operation disable mode prohibits the operation device from inputting an operation from the operator. The input operation mode setup element switches the operation device from the input operation disable mode to the input operation enable mode when the releasing visual line determination element determines that the visual line is disposed in the predetermined operation releasing visual line state.

When the operation device is locked or inhibited against operations, the above-mentioned configuration can unlock the operation device in accordance with the visual line or movement of the user's eye. The operation device remains unlocked unless the user indicates his or her intention to perform an operation by setting his or her visual line to a specified state. It is possible to reliably prevent an incorrect operation on the operation device unlike a conventional mechanism that may unlock the operation element simply because a hand is detected near the operation element. Moving the visual line is more convenient for the user than moving the hand. It is possible to greatly improve the conventional inconvenient unlock operation.

Alternatively, the visual line detection element may include a face image capturing element for capturing a face image of the operator, and detects the visual line of the operator based on the face image. Recently, the driver's face image is captured for various technologies so as to detect inattentive driving or drowsiness. The existing capturing means can also be used and provide a cost-effective solution in total.

Alternatively, the operation releasing visual line state may be defined by a state that the visual line is directed to at least a predetermined operation releasing visual line area. When an operation lock is unlocked in accordance with a visual line (view destination), the user can easily unlock the operation lock simply by turning his or her gaze on that position. The unlock operation can be more reliable by providing the operation releasing visual line area at a position different from such areas viewed during driving as a windshield ahead of the driver, a side mirror, and a screen on the display apparatus.

Further, the operation releasing visual line state may be defined by a state that the visual line is continuously directed to the operation releasing visual line area for a predetermined view time. The unlock operation can be more reliable because the operation lock is unlocked only when the user attentively views the specified operation releasing visual line area. For example, the locked state remains unchanged when the visual line just passes over the operation releasing visual line area. It is possible to decrease the number of times to drive a lock mechanism for unlocking and help save power of the lock mechanism. An upper bound of the viewing time may be defined as 1.5 seconds.

Alternatively, the operation releasing visual line state may be defined by a state that a movement speed of the visual line is equal to or smaller than a predetermined speed when the visual line enters in the operation releasing visual line area. A lower bound can be appropriately defined in accordance with driving and ambient situations of a vehicle so as to ensure safe driving. The operation releasing visual line area may be provided at a position different from such areas viewed during driving as a windshield ahead of the driver, a side mirror, and a screen on the display apparatus. When a visual line detected by the visual line detection means enters the operation releasing visual line area, the operation releasing visual line state decreases a movement speed of the visual line to a predetermined speed level or lower. In this case, an unlock operation can be enabled just by decreasing the speed of moving the visual line over the operation releasing visual line area, making the unlock operation easier.

Alternatively, the operation releasing visual line area may be defined by a layout area of the operation device, to which an input operation mode is set, and the input operation mode includes the input operation enable mode and the input operation disable mode. Generally, the user visually checks an operation position on the operation element and then operates the operation device. The operation lock is unlocked at the instant of the visual check. There is no need for an unlock action as conventionally practiced. The unlock operation becomes less complicated and improves operability.

Further, the operation device may include a plurality of operation elements. The input operation mode setup element sets the input operation mode to each operation element. The plurality of operation elements includes a element of the plurality of operation elements, which is defined as a predetermined operation element group. Each operation element in the operation element group has a corresponding operation releasing visual line area. The releasing visual line determination element specifies the operation releasing visual line state corresponding to each operation element in the operation element group, and defines the operation element group as an operable operation element group when the visual line is disposed in the operation releasing visual line state and is directed to the operation element group. The input operation mode setup element switches each operation element in the operation element group from the input operation disable mode to the input operation enable mode when the releasing visual line determination element determines that the visual line is disposed in the operation releasing visual line state, and the input operation mode setup element maintains a remaining part of the plurality of operation elements to be in the input operation disable mode. In this manner, many operation elements provided for a vehicle component can be integrated into an operation element group. An input operation mode can be assigned to each operation element group. Processing loads can be decreased in comparison with the configuration of assigning input operation modes to individual switches and buttons.

Further, each operation element in the operation element group may have the same operation object or the same operation function. Operation elements associated with a device or a device function may be successively operated. The input operation mode for the operation elements can be changed at a time, making it possible to greatly reduce processing loads. Alternatively, each operation element in the operation element group may be disposed in a predetermined layout area. When two operation elements are positioned adjacently with each other, both may be operated one after another. The input operation mode for both can be changed at a time, making it possible to greatly reduce processing loads.

Alternatively, the input apparatus may further include: an operation disable mode recovery element switching the operation device from the operation enable mode to the operation disable mode after a predetermined operation enable time has elapsed since the operation mode setup element set the operation enable mode. This configuration can reliably return the input operation mode once defined as the input operation enable mode to the input operation disable mode.

Alternatively, the operation device may include a touch operation panel so that the occupant touches the panel to input operation. An unintentional incorrect operation may easily result from a touch panel that allows just a contact to cause input. The operation element is preferable for preventing incorrect operations.

Alternatively, the operation device may be arranged at a position where the occupant can operate the operation element even when the occupant sits down on a seat of the vehicle with leaning the occupant back on a backrest of the seat. The operation device easily accessible from an occupant is preferable for preventing incorrect operations.

Alternatively, the operation element may be a remote operation element, which is arranged at a position nearer a predetermined seat of the vehicle than a main operation device. The remote operation element is separately disposed from the main operation device, and the remote operation element executes remote input into the main operation device. The remote operation element more easily accessible than the main operation element is also preferable for preventing incorrect operations.

Alternatively, the input apparatus may further include: a display arranged on a front side of the vehicle and visible by the occupant, who sits down on a driver seat of the vehicle. The main operation device is a touch panel mounted on the display, and the remote operation element is arranged between a bottom of the driver seat and a bottom of the front passenger seat. Further, the input apparatus may further include: a hand image capturing element capturing a hand image of an operator, who operates the remote operation element; and a hand image display element specifying an indicating position on the display based on the hand image, and superimposing a position indication image at the indicating position on the display. The operability of the remote operation element is improved.

The operation device of an onboard device may be protected against incorrect operations. For example, operation device may include one or more of an air conditioner operation element, an audio operation element, a navigation operation element, a power window operation element, and a seat adjusting operation element.

According to a third aspect of the present disclosure, a remote controller includes: an operation device including an operation element remotely operating an in-vehicle device; a locking element switching the operation element between a lock mode and an unlock mode, wherein the operation element is operable when the locking element switches to the unlock mode, and the operation element is not operable when the locking element switches to the lock mode; a load detection element detecting a load applied to the operation element; and a control element controlling the locking element. The control element controls the locking element to switch to the lock mode when the load is smaller than a predetermined value, and the control element controls the locking element to switch to the unlock mode when the load is equal to or larger than the predetermined value.

The remote controller assumes the absence of a user intention to operate the operation part when a load detected by the load detection element is smaller than a predetermined value. The operation element remains locked under control of the locking element in accordance with the control element. On the other hand, the remote controller assumes the presence of a user intention to operate the operation element when a load detected by the load detection element is greater than or equal to the predetermined value. The operation element is unlocked under control of the locking element in accordance with the control element.

When the user inadvertently operates the operation element of the remote controller, a load detected by the load detection element is smaller than the predetermined value. The locking element keeps the operation element locked and nullifies an input operation on the operation element.

Alternatively, the control element may control the locking element to switch to the lock mode when no operation is input into the operation element for a predetermined time interval after the control element controls the locking element to switch to the unlock mode.

The user can be assumed to have no intention to operate the operation element when the operation element is unlocked and no input operation is performed afterwards on the operation part for a predetermined time period. In this case, locking the locking element makes it possible to effectively prevent the user from inadvertently operating the operation element.

Alternatively, the operation element may include a palm rest for placing a palm of an operator thereon, and a palm detection element for detecting the palm on the palm rest. The control element controls the locking element to maintain the unlock mode when the palm detection element detects the palm after the control element controls the locking element to switch to the unlock mode, and the control element controls the locking element to switch to the lock mode when the palm detection element does not detects the palm after the control element controls the locking element to switch to the unlock mode.

Generally, the user place his or her palm on the palm rest so as to immediately operate the operation element when he or she intends to operate the operation element. When the user releases his or her palm from the palm rest, he or she can be assumed to indicate no intention to operate the operation element. In this case, the locking element is locked even when the load detection element detects a load greater than or equal to the predetermined value. This makes it possible to more reliably prevent the user's inadvertent operation.

According to a fourth aspect of the present disclosure, an operating device for a vehicle includes: an operation element disposed within a reach of an operator; an operation determination element determining whether the operator operates the operation element; a display displaying an image on a screen of the display when the operation determination element determines that the operator operates the operation element, the image corresponding to an input operation of the operator; a visual line direction detection element detecting a direction of a visual line of the operator; and an operation mode control element switching the operation element from a normal mode to a restriction mode when the direction of the visual line is not directed to the screen of the display. The normal mode does not restrict the input operation of the operation element, and the restriction mode restricts the input operation of the operation element.

The above-mentioned configuration can detect a user's visual line direction to determine whether the user intentionally or unintentionally operates a tactilely operated device. It is possible to solve the problem of unintentionally touching the pointing device to cause an unexpected operation or display that may become a hindrance to driving.

Alternatively, the operation element may include a haptic device for specifying a position on a two-dimensional operation plane having a predetermined operation range. The above-mentioned configuration can also provide an effect of the invention when a haptic device is used as the tactilely operated device.

Further, the haptic device may be configured as a pointing device to be operated against a restoring force toward a neutral position. The haptic device has an operation axis, which is maintained at the neutral position when the haptic device is not operated. The operation axis slants from the neutral position toward a direction corresponding to the specified position on the screen when the haptic device is not operated, and the operation mode control applies the restoring force to the operation element in the restriction mode larger than the restoring force in the normal mode. Even when the user unintentionally operates the tactilely operated device (haptic device), the above-mentioned configuration increases or maximizes a restoring force toward the neutral position. It is possible to prevent the user from operating the device and prevent an operation or display the driver does not expect.

Furthermore, the operation mode control element may set the operation element in the restriction mode to be in a lock state so that the operation axis is maintained at a predetermined position. According to the above-mentioned configuration, the restriction mode disables the user from operating the tactilely operated device (haptic device). It is possible to prevent an operation or display the driver does not expect.

Furthermore, the operation mode control element may set the operation element in the restriction mode to maintain the operation axis at a position just before the operation mode control element switches the operation element from the normal mode to the restriction mode. After the restriction mode changes to the normal mode, the above-mentioned allows an operation to restart from an operation axis position immediately before the normal mode changes to the restriction mode. The user can streamline the operation without needing to restart the operation from the beginning.

Further, the operating device may further include: an operation axis position storage element storing an operation axis position of the operation element as a return position just before the operation mode control element switches the operation element from the normal mode to the restriction mode. The operation mode control element returns the operation axis position to the return position when the operation mode control element switches the operation element from the restriction mode to the normal mode. The above-mentioned configuration, the tactilely operated device (haptic device) returns to the operation axis position maintained immediately before the normal mode changes to the restriction mode. The user can streamline the operation because he or she can resume the operation from the operation axis position maintained immediately before the normal mode changes to the restriction mode.

Alternatively, the operating device may further include: wherein the operation mode control element cancels the input operation of the operation element when the operation element is in the restriction mode. The above-mentioned configuration can also prevent an operation or display the driver does not expect even when the user unintentionally operates the tactilely operated device (haptic device).

Alternatively, the operating device may further include: wherein the display is arranged at a position deviated from a usual visual line of a driver who drives the vehicle. On a head up display, for example, the display means is provided in the same direction as the driving direction of a vehicle. The direction of user's visual line may be ineffective in determining whether the user intentionally or unintentionally operates a tactilely operated device. On the other hand, the above-mentioned configuration makes it possible to determine whether or not the user unintentionally operates a tactilely operated device.

While the invention has been described with reference to preferred embodiments thereof, it is to be understood that the invention is not limited to the preferred embodiments and constructions. The invention is intended to cover various modification and equivalent arrangements. In additions while the various combinations and configurations, which are preferred, other combinations and configurations, including more, less or only a single element, are also within the spirit and scope of the invention.

What is claimed is:

1. An input apparatus for a vehicle comprising:
    an operation element operable by an occupant of the vehicle;
    a biological information acquisition element acquiring biological information of the occupant;
    an unawakened state detection element detecting an unawakened state of the occupant based on the biological information, wherein the unawakened state is defined by a predetermined state different from an awakened state; and
    an operation disabling element disabling an operation input from the operation element when the unawakened state detection element detects the unawakened state;
    wherein the occupant is a driver of the vehicle,
    wherein the operation element is a remote operation element, which is arranged at a position nearer a driver seat than a main operation device, and
    wherein the remote operation element is separately disposed from the main operation device, and
    wherein the remote operation element executes remote input into the main operation device.

2. The input apparatus according to claim 1, further comprising:
    a notification element notifying the occupant of disabling of the operation when the operation disabling element disables the operation.

3. The input apparatus according to claim 2, further comprising:
    a display arranged on a front side of the vehicle and visible by the occupant, who sits down on a seat of the vehicle,
    wherein the notification element controls the display to change a part of or all of a screen image on the display when the operation disabling element disables the operation.

4. The input apparatus according to claim 1, further comprising:
    an awakening element awakening a driver of the vehicle,
    wherein the occupant is the driver, and
    wherein the awakening element awakens the driver when the operation disabling element disables the operation.

5. The input apparatus according to claim 3, further comprising:
    a notification element notifying the occupant of disabling of the operation when the operation disabling element disables the operation,
    wherein the notification element functions as an awakening element for awakening a driver of the vehicle,
    wherein the occupant is the driver, and
    wherein the awakening element awakens the driver when the operation disabling element disables the operation.

6. The input apparatus according to claim 5,
    wherein the awakening element executes at least one of increasing an operation reaction force of the operation element, vibrating the operation element, increasing an operation sound of the operation element, changing the operation sound of the operation element, outputting an alarm sound, increasing a force for tightening a seat belt of the vehicle, vibrating the seat belt, and supplying air from an air conditioner of the vehicle.

7. The input apparatus according to claim 1, wherein the occupant is a driver of the vehicle,
    wherein the biological information acquisition element acquires the biological information of the driver, and
    wherein the operation element is arranged at a position where at least the driver sitting on a seat of the vehicle is configured to operating the operation element.

8. The input apparatus according to claim 1,
    wherein the biological information acquisition element includes a pupil detection element for detecting a chronological change of a pupil of the occupant,
    wherein the pupil detection element includes an eye image capturing element for capturing an eye image of the occupant, and
    wherein the pupil detection element detects the chronological change of a pupil size of the occupant based on the eye image.

9. The input apparatus according to claim 1,
    wherein the biological information acquisition element includes a blink detection element for detecting a blink of the occupant,
    wherein the blink detection element includes an eye image capturing element for capturing an eye image of the occupant, and
    wherein the blink detection element detects the blink based on the eye image.

10. The input apparatus according to claim 1,
    wherein the biological information acquisition element includes a biological waveform detection element for acquiring at least one of a pulse waveform, a heartbeat waveform, an electrocardiographic waveform and a brain waveform of the occupant, and
    wherein the biological waveform detection element contacts the occupant sitting on a seat of the vehicle.

11. The input apparatus according to claim 1,
    wherein the operation element includes a touch operation panel so that the occupant touches the panel to input operation.

12. The input apparatus according to claim 1,
    wherein the operation element is arranged at a position where the occupant is permitted to operate the operation element even when the occupant sits down on a seat of the vehicle with leaning the occupant back on a backrest of the seat.

13. The input apparatus according to claim 1, further comprising:
    a display arranged on a front side of the vehicle and visible by the occupant, who sits down on a driver seat or a front passenger seat,
    wherein the main operation device is a touch panel mounted on the display, and
    wherein the remote operation element is arranged between a bottom of the driver seat and a bottom of the front passenger seat.

14. The input apparatus according to claim 13, further comprising:
    a hand image capturing element capturing a hand image of an operator, who operates the remote operation element;
    a hand image display element specifying an indicating position on the display based on the hand image and superimposing a position indication image at the indicating position on the display;
    a display mode setup element setting one of a display disabling mode and a display enabling mode of the hand image display element, wherein the display disabling mode is set when the unawakened state detection element detects the unawakened state, wherein the display enabling mode is set when the unawakened state detection element does not detect the unawakened state, wherein the display disabling mode prohibits the hand image display element from superimposing the position indication image on the display, and wherein the display enabling mode allows the hand image display element to superimpose the position indication image on the display.

15. An input apparatus for a vehicle comprising:

an operation element operable by an occupant of the vehicle;

a biological information acquisition element acquiring biological information of the occupant;

an unawakened state detection element detecting an unawakened state of the occupant based on the biological information wherein the unawakened state is defined by a redetermined state different from an awakened state; and an operation disabling element disabling an operation input from the operation element when the unawakened state detection element detects the unawakened state;

wherein the operation element is at least one of an air conditioner operation part, an audio operation part, a navigation operation part, a power window operation part and a seat adjusting operation part.

* * * * *

UNITED STATES PATENT AND TRADEMARK OFFICE
CERTIFICATE OF CORRECTION

| | | |
|---|---|---|
| PATENT NO. | : 8,106,783 B2 | Page 1 of 1 |
| APPLICATION NO. | : 12/401881 | |
| DATED | : January 31, 2012 | |
| INVENTOR(S) | : Aoki et al. | |

It is certified that error appears in the above-identified patent and that said Letters Patent is hereby corrected as shown below:

Title Page, Item (12) "Wada et al." should read -- Aoki et al. --

Title Page, Item (75) Inventors should read -- Takashi Aoki, Gifu-city (JP); Fumio Nakamura, Okazaki-city (JP) --

Signed and Sealed this
Twenty-seventh Day of March, 2012

David J. Kappos
*Director of the United States Patent and Trademark Office*